(12) United States Patent
Vanslyke et al.

(10) Patent No.: US 10,231,659 B2
(45) Date of Patent: *Mar. 19, 2019

(54) FAULT DISCRIMINATION AND RESPONSIVE PROCESSING BASED ON DATA AND CONTEXT

(71) Applicant: DexCom, Inc., San Diego, CA (US)

(72) Inventors: Stephen J. Vanslyke, Carlsbad, CA (US); Naresh C. Bhavaraju, San Diego, CA (US); Sebastian Böhm, San Diego, CA (US); Leif N. Bowman, San Diego, CA (US); Michael J. Estes, Poway, CA (US); Arturo Garcia, Chula Vista, CA (US); Apurv Ullas Kamath, San Diego, CA (US); Andrew Attila Pal, San Diego, CA (US); Thomas A. Peyser, Menlo Park, CA (US); Anna Leigh Rack-Gomer, Cardiff by the Sea, CA (US); Daiting Rong, San Diego, CA (US); Disha B. Sheth, San Marcos, CA (US); Peter C. Simpson, Cardiff, CA (US); Dmytro Sokolovsky, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 492 days.

This patent is subject to a terminal disclaimer.

(21) Appl. No.: 14/717,965

(22) Filed: May 20, 2015

(65) Prior Publication Data

US 2015/0351672 A1     Dec. 10, 2015

Related U.S. Application Data

(63) Continuation of application No. 14/717,643, filed on May 20, 2015.

(Continued)

(51) Int. Cl.
*A61B 5/00* (2006.01)
*A61B 5/1495* (2006.01)
(Continued)

(52) U.S. Cl.
CPC .............. *A61B 5/1495* (2013.01); *A61B 5/01* (2013.01); *A61B 5/053* (2013.01); *A61B 5/1118* (2013.01);
(Continued)

(58) Field of Classification Search
CPC ........................... A61B 5/1495; A61B 5/14532
See application file for complete search history.

(56) References Cited

U.S. PATENT DOCUMENTS 8,260,393 B2   9/2012   Kamath et al.
8,423,113 B2   4/2013   Shariati et al.
(Continued)

OTHER PUBLICATIONS

Facchinetti et al. 2011. IEEE Trans Biomed Eng (BME) 58(9):2664-2671. Online denoising method to handle intra-individual variability of signal-to-noise ration in continuous g.

(Continued)

*Primary Examiner* — Christian Jang
(74) *Attorney, Agent, or Firm* — Knobbe Martens Olson & Bear, LLP

(57) ABSTRACT

Systems and methods disclosed here provide ways to discriminate fault types encountered in analyte sensors and systems and further provide ways to process such discriminated faults responsively based on sensor data, clinical context information, and other data about the patient or patient's environment. The systems and methods thus employ clinical context in detecting and/or responding to errors or faults associated with an analyte sensor system, and discriminating the type of fault, and its root cause, particularly as fault dynamics can appear similar to the dynamics of (Continued)

physiological systems, emphasizing the importance of discriminating the fault and providing appropriate responsive processing. Thus, the disclosed systems and methods consider the context of the patient's health condition or state in determining how to respond to the fault.

20 Claims, 56 Drawing Sheets

Related U.S. Application Data

(60) Provisional application No. 62/009,065, filed on Jun. 6, 2014.

(51) Int. Cl.

| | |
|---|---|
| A61B 5/01 | (2006.01) |
| A61B 5/11 | (2006.01) |
| A61B 5/053 | (2006.01) |
| A61B 5/145 | (2006.01) |
| A61B 5/1486 | (2006.01) |
| A61B 5/1473 | (2006.01) |
| A61M 5/172 | (2006.01) |
| G06F 19/00 | (2018.01) |

(52) U.S. Cl.
CPC ........ *A61B 5/1473* (2013.01); *A61B 5/14532* (2013.01); *A61B 5/14542* (2013.01); *A61B 5/14546* (2013.01); *A61B 5/14865* (2013.01); *A61B 5/4833* (2013.01); *A61B 5/4839* (2013.01); *A61B 5/4848* (2013.01); *A61B 5/4866* (2013.01); *A61B 5/6898* (2013.01); *A61B 5/7203* (2013.01); *A61B 5/7221* (2013.01); *A61B 5/7275* (2013.01); *A61B 5/7278* (2013.01); *A61B 5/7282* (2013.01); *A61B 5/742* (2013.01); *A61B 5/746* (2013.01); *A61M 5/1723* (2013.01); *G06F 19/00* (2013.01); *A61B 2560/0247* (2013.01); *A61B 2560/0252* (2013.01); *A61B 2560/0276* (2013.01); *A61B 2560/0475* (2013.01); *A61B 2562/0247* (2013.01); *A61M 2205/3584* (2013.01); *A61M 2205/3592* (2013.01); *A61M 2205/50* (2013.01); *A61M 2205/52* (2013.01); *A61M 2230/201* (2013.01)

(56) References Cited

U.S. PATENT DOCUMENTS

| | | |
|---|---|---|
| 9,211,092 B2 | 12/2015 | Bhavaraju et al. |
| 2003/0035575 A1 | 2/2003 | Mayou et al. |
| 2009/0192366 A1 | 7/2009 | Mensinger et al. |
| 2011/0184267 A1* | 7/2011 | Duke ................ A61B 5/14532 600/365 |
| 2012/0078071 A1* | 3/2012 | Bohm ................... G06F 1/3203 600/345 |
| 2012/0265035 A1 | 10/2012 | Bohm et al. |
| 2013/0231543 A1 | 9/2013 | Facchinetti et al. |
| 2013/0245401 A1 | 9/2013 | Estes et al. |
| 2014/0005505 A1* | 1/2014 | Peyser ................ A61B 5/7221 600/316 |
| 2014/0005508 A1 | 1/2014 | Estes et al. |
| 2014/0005509 A1 | 1/2014 | Bhavaraju et al. |
| 2014/0129151 A1 | 5/2014 | Bhavaraju et al. |
| 2014/0278189 A1 | 9/2014 | Vanslyke et al. |

OTHER PUBLICATIONS

Facchinetti et al. 2013. IEEE Trans Biomed Eng (BME) 60(2):406-416. An online failure detection method of the glucose sensor-insulin pump system: improved overnight safety.

* cited by examiner

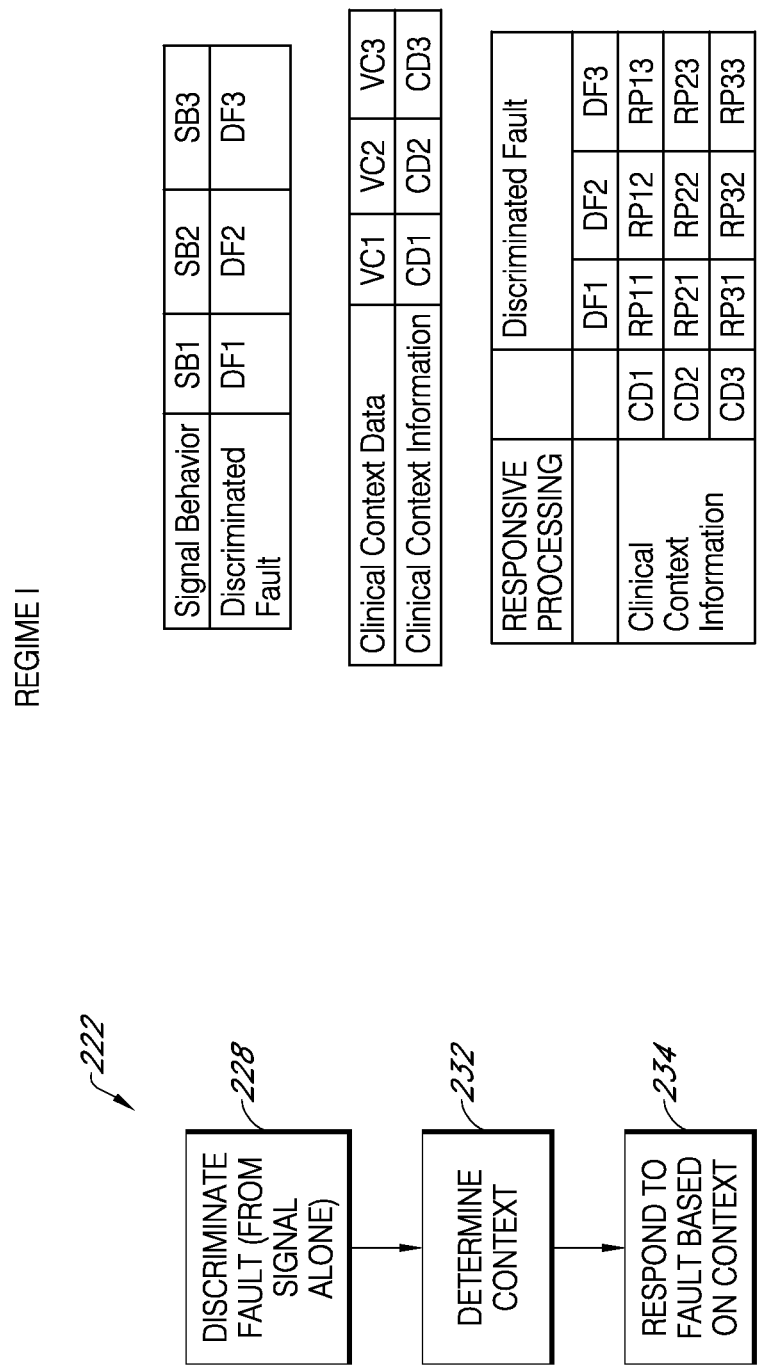

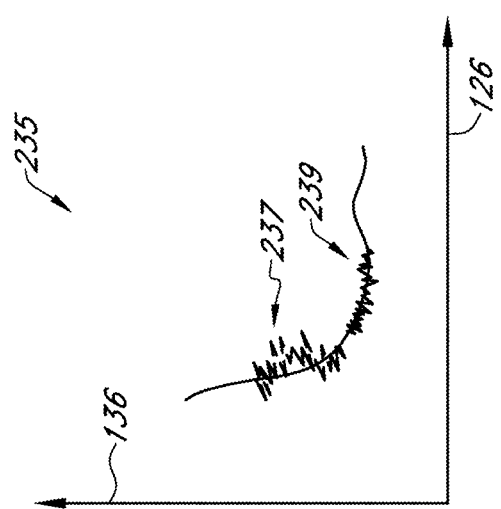

FIG. 20

| Signal Behavior 1 | Signal Behavior 2 | Clinical Context Information 1 | Clinical Context Information 2 | Fault Category | Responsive Processing |
|---|---|---|---|---|---|
| RAPID RISE / RAPID DECLINE (WILL HAVE DIFFERENT FAULTS DISCRIMINATED) | NOISY | HYPO-GLYCEMIC | EXERCISING | | |
| | | | SEDENTARY | | |
| | | | SHOWERING | | |
| | | | SLEEPING | | |
| | | | EATING | | |
| | | HYPER-GLYCEMIC | EXERCISING | | |
| | | | SEDENTARY | | |
| | | | SHOWERING | | |
| | | | SLEEPING | | |
| | | | EATING | | |
| | | EU-GLYCEMIC | EXERCISING | | |
| | | | SEDENTARY | | |
| | | | SHOWERING | | |
| | | | SLEEPING | | |
| | | | EATING | WILL VARY BASED ON SB1, SB2, CD1, CD2 | WILL VARY BASED ON DISCRIMINATED FAULT AND OPTIONALLY ON CD1, CD2 |
| | STABLE | HYPO-GLYCEMIC | EXERCISING | | |
| | | | SEDENTARY | | |
| | | | SHOWERING | | |
| | | | SLEEPING | | |
| | | | EATING | | |
| | | HYPER-GLYCEMIC | EXERCISING | | |
| | | | SEDENTARY | | |
| | | | SHOWERING | | |
| | | | SLEEPING | | |
| | | | EATING | | |
| | | EU-GLYCEMIC | EXERCISING | | |
| | | | SEDENTARY | | |
| | | | SHOWERING | | |
| | | | SLEEPING | | |
| | | | EATING | | |

| FAULT DISCRIMINATION OR CATEGORIZATION IN ORDER OF LIKELIHOOD OF OCCURRENCE | Signal Analysis Criteria | Current Signal Analysis Data | Clinical Context Criteria | Current Clinical Context Data |
|---|---|---|---|---|
| Fault Type 1 | SAC1 | e.g., SAi | CCI1 | e.g., CCj |
| Fault Type 2 | SAC2 | | CCI2 | |
| Fault Type 3 | SAC3 | | CCI3 | |

FIG. 21

FAULT DISCRIMINATION AND RESPONSIVE PROCESSING BASED ON DATA AND CONTEXT

CROSS-REFERENCE TO RELATED APPLICATION

Any and all priority claims identified in the Application Data Sheet, or any correction thereto, are hereby incorporated by reference under 37 CFR 1.57. This application is a continuation of U.S. application Ser. No. 14/717,643, filed May 20, 2015, which claims the benefit of U.S. Provisional Application No. 62/009,065, filed Jun. 6, 2014. The aforementioned applications are incorporated by reference herein in their entirety, and are hereby expressly made a part of this specification.

TECHNICAL FIELD

The present embodiments relate to continuous analyte monitoring, and, in particular, to fault discrimination and responsive processing within a continuous analyte monitoring system.

BACKGROUND

Diabetes mellitus is a disorder in which the pancreas cannot create sufficient insulin (Type I or insulin-dependent) and/or in which insulin is not effective (Type II or non-insulin-dependent). In the diabetic state, the patient or user suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. It is not only unlikely that a person with diabetes will become aware of a dangerous condition in time to counteract it, but it is also likely that he or she will not know whether his or her blood glucose value is going up (higher) or down (lower) based on conventional method. Diabetics thus may be inhibited from making educated insulin therapy decisions.

Another device that some diabetics used to monitor their blood glucose is a continuous analyte sensor, e.g., a continuous glucose monitor (CGM). A CGM typically includes a sensor that is placed invasively, minimally invasively or non-invasively. The sensor measures the concentration of a given analyte within the body, e.g., glucose, and generates a raw signal that is generated by electronics associated with the sensor. The raw signal is converted into an output value that is rendered on a display. The output value that results from the conversion of the raw signal is typically expressed in a form that provides the user with meaningful information, and in which form users become familiar with analyzing, such as blood glucose expressed in mg/dL.

The above discussion assumes a reliable and true raw signal is received by the electronics. In some cases, faults or errors are encountered and the signal is no longer reliable and true. Prior art approaches to detecting such are generally of a "one-size-fits-all" approach, as is systems' response to the same.

Faults or errors may be caused in a number of ways. For example, they may be associated with a physiological activity in the host, e.g., metabolic responses, or may also be associated with an in vivo portion of the sensor as the same settles into the host environment. They may also be associated with transient events within the control of a patient, or associated with the external environment surrounding the device. Other such are also seen.

Additionally, in the case of glucose monitoring, as glucose levels and patterns vary from patient-to-patient and even within a patient from day-to-day, noise may be difficult to differentiate from large glucose swings. Similarly, a solution that is best for a patient with stable glucose at one particular time may not be the best solution for the same or different patient at or near hypoglycemia or hyperglycemia, for example.

SUMMARY

The present embodiments have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

Systems and methods according to present principles appreciate that clinical context matters in detecting and/or responding to errors or faults associated with an analyte sensor system. The same further understand that the clinical context bears on discriminating the type of fault, and its root cause, particularly as fault dynamics can appear similar to glycemic dynamics, emphasizing the importance of discriminating the fault and providing appropriate responsive processing. Thus, the disclosed systems and methods further consider the context of the patient's health condition or state in determining how to respond to the fault. In this way, clinical context adds an element of knowledge of clinical risk (e.g., acuity of disease state) in the interpretation of the sensor data, and thus in the processing and display of sensor data.

In a first aspect, a method is provided for discriminating a fault type in a continuous in vivo analyte monitoring system, including: receiving a signal from an analyte monitor; receiving clinical context data; evaluating the clinical context data against clinical context criteria to determine clinical context information; discriminating the fault type based on both the received signal from the analyte monitor and the clinical context information; and performing responsive processing based on at least the discriminated fault type.

In a second aspect, a method is provided for discriminating a fault type in a continuous in vivo analyte monitoring system, including: receiving a signal from an analyte monitor; receiving clinical context data; evaluating the clinical context data against clinical context criteria to determine clinical context information; discriminating the fault type based on only the received signal; performing responsive processing based on the discriminated fault type and the determined clinical context information.

In a third aspect, a method is provided for performing responsive processing in response to a fault in a continuous in vivo analyte monitoring system, including: receiving a signal from an analyte monitor; receiving clinical context data; evaluating the received clinical context data against clinical context criteria to determine clinical context information; performing responsive processing based on at least the received signal and the determined clinical context information.

In a fourth aspect, a method is provided for discriminating a fault type in a continuous in vivo analyte monitoring system, including: receiving a signal from an analyte monitor; receiving clinical context data; transforming the clinical context data into clinical context information; discriminating the fault type based on both the received signal from the analyte monitor and the clinical context information; and performing responsive processing based on at least the discriminated fault type.

In a fifth aspect, a method is provided for discriminating a fault type in a continuous in vivo analyte monitoring system, including: receiving a signal from an analyte monitor; evaluating the received signal against fault discrimination criteria to determine fault information; determining clinical context information; discriminating the fault type based on both the fault information and the clinical context information; and performing responsive processing based on at least the discriminated fault type.

Implementations of the above-noted aspects may include one or more of the following. The discriminating may include categorizing the fault based on the received signal, the clinical context information, or both. The discriminating may include categorizing the fault based on the received signal, the clinical context information, or both, and where the categorizing the fault includes categorizing the fault as a sensor environment fault or as a system error/artifact fault. The discriminating may include categorizing the fault as a sensor environment fault, and further including subcategorizing the fault as a compression fault or an early wound response fault. The discriminating may include determining if the received signal or the received data matches or meets a predetermined criterion. The discriminating may include analyzing the signal using a time-based technique, a frequency-based technique, or a wavelet-based technique. The discriminating may include raw signal analysis, residualized signal analysis, pattern analysis, and/or slow versus fast sampling. The discriminating may include projecting the received signal onto a plurality of templates, each template corresponding to a fault mode. The discriminating may include variability analysis or fuzzy logic analysis. The received clinical context data may be selected from the group consisting of: age, anthropometric data, drugs currently operating on the patient, temperature as compared to a criteria, a fault history of the patient, activity level of the patient, exercise level of the patient, a patient level of interaction with a glucose monitor, patterns of glucose signal values, clinical glucose value and its derivatives, a range of patient glucose levels over a time period, a duration over which patient glucose levels are maintained in a range, a patient glucose state, a glycemic urgency index, time of day, or pressure. The method may further include processing the signal, e.g., where the processing removes or filters noise from the signal. The method may further include receiving an additional signal, such as a sensor temperature signal, an impedance signal, an oxygen signal, a pressure signal, or a background signal. The clinical context information may correspond to data about the patient excluding a signal value measured at a sensor associated with the analyte monitor.

The clinical context criteria may include predefined values or ranges of parameters selected from the group consisting of: drugs currently operating on the patient, temperature, a fault history of the patient, activity level of the patient, exercise level of the patient, a patient level of interaction with a glucose monitor, patterns of glucose signal values, clinical glucose value and its derivatives, a range of patient glucose levels over a time period, a duration over which patient glucose levels are maintained in a range, a patient glucose state, a glycemic urgency index, time of day, or pressure. The clinical context data may include temperature, the clinical context criteria may include a pattern of temperatures, the evaluating may determine the clinical context information to be that the user is in contact with water at the sensor site, and the discriminating the fault type may include discriminating the fault type as water ingress. The clinical context data may include patient activity level or time of day, the clinical context criteria may include a pattern of patient activity levels, the evaluating may determine the clinical context information to be that the user is compressing the sensor site, and the discriminating the fault type may include discriminating the fault type as compression. The clinical context data may include time since implant, the clinical context criteria may include a range of times since implant in which dip and recover faults are likely, the evaluating may determine the clinical context information to be that the sensor is recently implanted, and the discriminating the fault type may include discriminating the fault type as a dip and recover fault. The clinical context data may include a clinical glucose value and a datum selected from the group consisting of: age, anthropometric data, activity, exercise, clinical use of data, or patient interaction with monitor.

The responsive processing may include providing a display to a user, the display including a warning, an alert, an alarm, a confidence indicator, a range of values, a predicted value, or a blank screen. The performing responsive processing may include adjusting a level of filtering of the received signal. The performing responsive processing may include performing a prediction of a future signal value based on the received signal. The performing responsive processing may include performing a self diagnostics routine. The performing responsive processing may include performing a step of compensation. The performing responsive processing may include switching from a first therapeutic mode to a second therapeutic mode.

In a sixth aspect, a system is provided for performing any of the above methods.

In a seventh aspect, a device is provided substantially as shown and/or described the specifications and/or drawings.

In an eighth aspect, a method is provided substantially as shown and/or described the specifications and/or drawings.

In a ninth aspect, an electronic device is provided for monitoring data associated with a physiological condition, including: a continuous analyte sensor, where the continuous analyte sensor is configured to substantially continuously measure the concentration of analyte in the host, and to provide continuous sensor data associated with the analyte concentration in the host; and a processor module configured to perform a method substantially as shown and/or described the specifications and/or drawings. The analyte may be glucose.

In a tenth aspect, electronic device is provided for delivering a medicament to a host, the device including: a medicament delivery device configured to deliver medicament to the host, where the medicament delivery device is operably connected to a continuous analyte sensor, where the continuous analyte sensor is configured to substantially continuously measure the concentration of analyte in the host, and to provide continuous sensor data associated with the analyte concentration in the host; and a processor module configured to perform a method substantially as shown and/or described the specifications and/or drawings. The analyte may be glucose and the medicament may be insulin.

To ease the understanding of the described features, continuous glucose monitoring is used as part of the explanations that follow. It will be appreciated that the systems and methods described are applicable to other continuous monitoring systems, e.g., of analytes. For example, the features discussed may be used for continuous monitoring of lactate, free fatty acids, heart rate during exercise, IgG-anti gliadin, insulin, glucagon, movement tracking, fertility, caloric intake, hydration, salinity, sweat/perspiration (stress), ketones, adipanectin, troponin, perspiration, and/or body temperature. Where glucose monitoring is used as an example, one or more of these alternate examples of monitoring conditions may be substituted.

Any of the features of embodiments of the various aspects disclosed is applicable to all aspects and embodiments identified. Moreover, any of the features of an embodiment is independently combinable, partly or wholly with other embodiments described herein, in any way, e.g., one, two, or three or more embodiments may be combinable in whole or in part. Further, any of the features of an embodiment of the various aspects may be made optional to other aspects or embodiments. Any aspect or embodiment of a method can be performed by a system or apparatus of another aspect or embodiment, and any aspect or embodiment of the system can be configured to perform a method of another aspect or embodiment.

BRIEF DESCRIPTION OF THE DRAWINGS

The present embodiments now will be discussed in detail with an emphasis on highlighting the advantageous features. These embodiments depict the novel and nonobvious fault discrimination and responsive processing systems and methods shown in the accompanying drawings, which are for illustrative purposes only. These drawings include the following figures, in which like numerals indicate like parts:

FIGS. 12A-12C illustrates aspects of a first regime of fault discrimination and responsive processing;

FIG. 20 is a look-up table for use in responsive processing;

FIG. 21 is another table for use in responsive processing;

DETAILED DESCRIPTION

Definitions

Figure 1A:
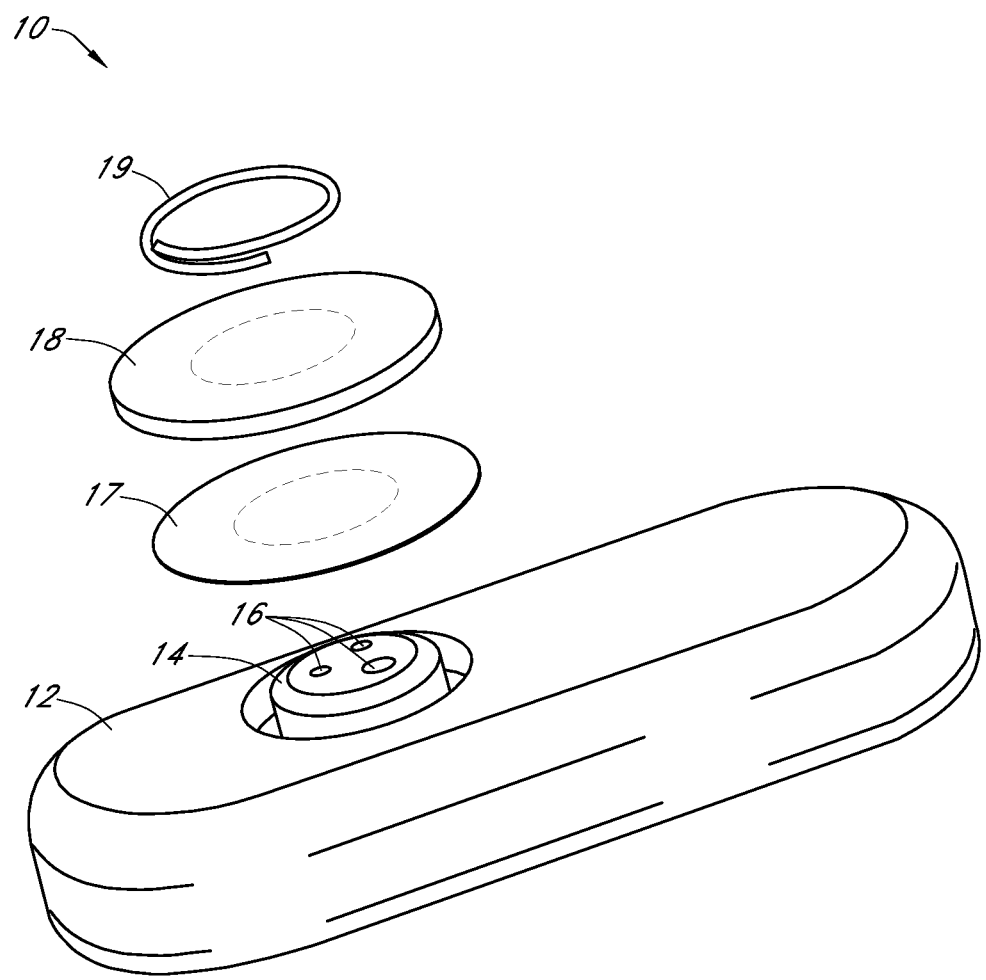
FIG. 1A is an exploded perspective view of a glucose sensor in one embodiment.

In order to facilitate an understanding of the preferred embodiments, a number of terms are defined below.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "ROM" as used herein is a broad term and is to be given its ordinary and customary meaning to a person of ordinary skill in the art (and is not to be limited to a special or customized meaning), and furthermore refers without limitation to read-only memory, which is a type of data storage device manufactured with fixed contents. ROM is broad enough to include EEPROM, for example, which is electrically erasable programmable read-only memory (ROM).

The term "RAM" as used herein is a broad term and is to be given its ordinary and customary meaning to a person of ordinary skill in the art (and is not to be limited to a special or customized meaning), and furthermore refers without limitation to a data storage device for which the order of access to different locations does not affect the speed of access. RAM is broad enough to include SRAM, for example, which is static random access memory that retains data bits in its memory as long as power is being supplied.

The term "A/D Converter" as used herein is a broad term and is to be given its ordinary and customary meaning to a person of ordinary skill in the art (and is not to be limited to a special or customized meaning), and furthermore refers without limitation to hardware and/or software that converts analog electrical signals into corresponding digital signals.

The terms "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The term "RF transceiver" as used herein is a broad term and is to be given its ordinary and customary meaning to a person of ordinary skill in the art (and is not to be limited to a special or customized meaning), and furthermore refers without limitation to a radio frequency transmitter and/or receiver for transmitting and/or receiving signals.

The term "jitter" as used herein is a broad term and is to be given its ordinary and customary meaning to a person of ordinary skill in the art (and is not to be limited to a special or customized meaning), and furthermore refers without limitation to noise above and below the mean caused by ubiquitous noise caused by a circuit and/or environmental effects; jitter can be seen in amplitude, phase timing, or the width of the signal pulse.

The terms "raw data stream" and "data stream" as used herein are broad terms and are to be given their ordinary and customary meaning to a person of ordinary skill in the art (and are not to be limited to a special or customized meaning), and furthermore refer without limitation to an analog or digital signal directly related to the measured glucose from the glucose sensor. In one example, the raw data stream is digital data in "counts" converted by an A/D converter from an analog signal (e.g., voltage or amps) and includes one or more data points representative of a glucose concentration. The terms broadly encompass a plurality of time spaced data points from a substantially continuous glucose sensor, which comprises individual measurements taken at time intervals ranging from fractions of a second up to, e.g., 1, 2, or 5 minutes or longer. In another example, the raw data stream includes an integrated digital value, wherein the data includes one or more data points representative of the glucose sensor signal averaged over a time period.

The term "calibration" as used herein is a broad term and is to be given its ordinary and customary meaning to a person of ordinary skill in the art (and is not to be limited to a special or customized meaning), and furthermore refers without limitation to the process of determining the relationship between the sensor data and the corresponding reference data, which can be used to convert sensor data into meaningful values substantially equivalent to the reference data, with or without utilizing reference data in real time. In some embodiments, namely, in continuous analyte sensors, calibration can be updated or recalibrated (at the factory, in real time and/or retrospectively) over time as changes in the relationship between the sensor data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, to provide a meaningful value to a user.

The terms "smoothed data" and "filtered data" as used herein are broad terms and are to be given their ordinary and customary meaning to a person of ordinary skill in the art (and are not to be limited to a special or customized meaning), and furthermore refer without limitation to data that has been modified to make it smoother and more continuous and/or to remove or diminish outlying points, for example, by performing a moving average of the raw data stream. Examples of data filters include FIR (finite impulse response), IIR (infinite impulse response), moving average filters, and the like.

The terms "smoothing" and "filtering" as used herein are broad terms and are to be given their ordinary and customary meaning to a person of ordinary skill in the art (and are not to be limited to a special or customized meaning), and furthermore refer without limitation to modification of a set of data to make it smoother and more continuous or to remove or diminish outlying points, for example, by performing a moving average of the raw data stream.

The term "algorithm" as used herein is a broad term and is to be given its ordinary and customary meaning to a person of ordinary skill in the art (and is not to be limited to a special or customized meaning), and furthermore refers without limitation to a computational process (for example, programs) involved in transforming information from one state to another, for example, by using computer processing.

The term "matched data pairs" as used herein is a broad term and is to be given its ordinary and customary meaning to a person of ordinary skill in the art (and is not to be limited to a special or customized meaning), and furthermore refers without limitation to reference data (for example, one or more reference analyte data points) matched with substantially time corresponding sensor data (for example, one or more sensor data points).

The term "counts" as used herein is a broad term and is to be given its ordinary and customary meaning to a person of ordinary skill in the art (and is not to be limited to a special or customized meaning), and furthermore refers without limitation to a unit of measurement of a digital signal. In one example, a raw data stream measured in counts is directly related to a voltage (e.g., converted by an A/D converter), which is directly related to current from the working electrode. In another example, counter electrode voltage measured in counts is directly related to a voltage.

The term "sensor" as used herein is a broad term and is to be given its ordinary and customary meaning to a person of ordinary skill in the art (and is not to be limited to a special or customized meaning), and furthermore refers without limitation to the component or region of a device by which an analyte can be quantified.

The term "needle" as used herein is a broad term and is to be given its ordinary and customary meaning to a person of ordinary skill in the art (and is not to be limited to a special or customized meaning), and furthermore refers without limitation to a slender instrument for introducing material into or removing material from the body.

The terms "glucose sensor" and "member for determining the amount of glucose in a biological sample" as used herein are broad terms and are to be given their ordinary and customary meaning to a person of ordinary skill in the art (and are not to be limited to a special or customized meaning), and furthermore refer without limitation to any mechanism (e.g., enzymatic or non-enzymatic) by which glucose can be quantified. For example, some embodiments utilize a membrane that contains glucose oxidase that catalyzes the conversion of oxygen and glucose to hydrogen peroxide and gluconate, as illustrated by the following chemical reaction:

$$Glucose + O_2 \rightarrow Gluconate + H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The terms "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s) in a manner that allows transmission of signals between the components. For example, one or more electrodes can be used to detect the amount of glucose in a sample and convert that information into a signal, e.g., an electrical or electromagnetic signal; the signal can then be transmitted to an electronic circuit. In this case, the electrode is "operably linked" to the electronic circuitry. These terms are broad enough to include wireless connectivity.

The term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, calculating, deriving, establishing and/or the like.

The term "message" encompasses a wide variety of formats for transmitting information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed/transmitted/stored/received/etc. in multiple parts.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "proximal" as used herein is a broad term and is to be given its ordinary and customary meaning to a person of ordinary skill in the art (and is not to be limited to a special or customized meaning), and furthermore refers without limitation to near to a point of reference such as an origin, a point of attachment, or the midline of the body. For example, in some embodiments of a glucose sensor, wherein the glucose sensor is the point of reference, an oxygen sensor located proximal to the glucose sensor will be in contact with or nearby the glucose sensor such that their respective local environments are shared (e.g., levels of glucose, oxygen, pH, temperature, etc. are similar).

The term "distal" as used herein is a broad term and is to be given its ordinary and customary meaning to a person of ordinary skill in the art (and is not to be limited to a special or customized meaning), and furthermore refers without limitation to spaced relatively far from a point of reference, such as an origin or a point of attachment, or midline of the body. For example, in some embodiments of a glucose sensor, wherein the glucose sensor is the point of reference, an oxygen sensor located distal to the glucose sensor will be sufficiently far from the glucose sensor such their respective local environments are not shared (e.g., levels of glucose, oxygen, pH, temperature, etc. may not be similar).

The term "domain" as used herein is a broad term and is to be given its ordinary and customary meaning to a person of ordinary skill in the art (and is not to be limited to a special or customized meaning), and furthermore refers without limitation to a region of the membrane system that can be a layer, a uniform or non-uniform gradient (for example, an anisotropic region of a membrane), or a portion of a membrane.

The terms "in vivo portion" and "distal portion" as used herein are broad terms and are to be given their ordinary and customary meaning to a person of ordinary skill in the art (and are not to be limited to a special or customized meaning), and furthermore refer without limitation to the portion of the device (for example, a sensor) adapted for insertion into and/or existence within a living body of a host.

The terms "ex vivo portion" and "proximal portion" as used herein are broad terms and are to be given their ordinary and customary meaning to a person of ordinary skill in the art (and are not to be limited to a special or customized meaning), and furthermore refer without limitation to the portion of the device (for example, a sensor) adapted to remain and/or exist outside of a living body of a host.

The term "electrochemical cell" as used herein is a broad term and is to be given its ordinary and customary meaning to a person of ordinary skill in the art (and is not to be limited to a special or customized meaning), and furthermore refers without limitation to a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The term "electrical potential" as used herein is a broad term and is to be given its ordinary and customary meaning to a person of ordinary skill in the art (and is not to be limited to a special or customized meaning), and furthermore refers without limitation to the electrical potential difference between two points in a circuit which is the cause of the flow of a current.

The term "host" as used herein is a broad term and is to be given its ordinary and customary meaning to a person of ordinary skill in the art (and is not to be limited to a special or customized meaning), and furthermore refers without limitation to mammals, particularly humans.

The term "continuous analyte (or glucose) sensor" as used herein is a broad term and is to be given its ordinary and customary meaning to a person of ordinary skill in the art (and is not to be limited to a special or customized meaning), and furthermore refers without limitation to a device that continuously or continually measures a concentration of an analyte, for example, at time intervals ranging from fractions of a second up to, for example, 1, 2, or 5 minutes, or longer. In one exemplary embodiment, the continuous analyte sensor is a glucose sensor such as described in U.S. Pat. No. 6,001,067, which is incorporated herein by reference in its entirety.

The term "continuous analyte (or glucose) sensing" as used herein is a broad term and is to be given its ordinary and customary meaning to a person of ordinary skill in the art (and is not to be limited to a special or customized meaning), and furthermore refers without limitation to the period in which monitoring of an analyte is continuously or continually performed, for example, at time intervals ranging from fractions of a second up to, for example, 1, 2, or 5 minutes, or longer.

The terms "reference analyte monitor," "reference analyte meter," and "reference analyte sensor" as used herein are broad terms and are to be given their ordinary and customary meaning to a person of ordinary skill in the art (and are not to be limited to a special or customized meaning), and furthermore refer without limitation to a device that measures a concentration of an analyte and can be used as a reference for the continuous analyte sensor, for example a self-monitoring blood glucose meter (SMBG) can be used as a reference for a continuous glucose sensor for comparison, calibration, and the like.

The term "sensing membrane" as used herein is a broad term and is to be given its ordinary and customary meaning to a person of ordinary skill in the art (and is not to be limited to a special or customized meaning), and furthermore refers without limitation to a permeable or semi-permeable membrane that can be comprised of two or more domains and is typically constructed of materials of a few microns thickness or more, which are permeable to oxygen and may or may not be permeable to glucose. In one example, the sensing membrane comprises an immobilized glucose oxidase enzyme, which enables an electrochemical reaction to occur to measure a concentration of glucose.

The term "physiologically feasible" as used herein is a broad term and is to be given its ordinary and customary meaning to a person of ordinary skill in the art (and is not to be limited to a special or customized meaning), and furthermore refers without limitation to the physiological parameters obtained from continuous studies of glucose data in humans and/or animals. For example, a maximal sustained rate of change of glucose in humans of about 4 to 5 mg/dL/min and a maximum acceleration of the rate of change of about 0.1 to 0.2 mg/dL/min/min are deemed physiologically feasible limits. Values outside of these limits would be considered non-physiological and likely a result of signal error, for example. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data. As a further example, it has been observed that the best solution for the shape of the curve at any point along glucose signal data stream over a certain time period (e.g., about 20 to 30 minutes) is a straight line, which can be used to set physiological limits.

The term "ischemia" as used herein is a broad term and is to be given its ordinary and customary meaning to a person of ordinary skill in the art (and is not to be limited to a special or customized meaning), and furthermore refers without limitation to local and temporary deficiency of blood supply due to obstruction of circulation to a part (e.g., sensor). Ischemia can be caused by mechanical obstruction (e.g., arterial narrowing or disruption) of the blood supply, for example.

The term "system noise" as used herein is a broad term and is to be given its ordinary and customary meaning to a person of ordinary skill in the art (and is not to be limited to a special or customized meaning), and furthermore refers without limitation to unwanted electronic or diffusion-related noise which can include Gaussian, motion-related, flicker, kinetic, or other white noise, for example.

The terms "noise," "noise event(s)," "noise episode(s)," "signal artifact(s)," "signal artifact event(s)," and "signal artifact episode(s)" as used herein are broad terms and are to be given their ordinary and customary meaning to a person of ordinary skill in the art (and are not to be limited to a special or customized meaning), and furthermore refer without limitation to signal noise that is caused by substantially non-glucose related, such as interfering species, macro- or micro-motion, ischemia, pH changes, temperature changes, pressure, stress, or even unknown sources of mechanical, electrical and/or biochemical noise for example. In some embodiments, signal artifacts are transient and characterized by a higher amplitude than system noise, and described as "transient non-glucose related signal artifact(s) that have a higher amplitude than system noise." In some embodiments, noise is caused by rate-limiting (or rate-increasing) phenomena. In some circumstances, the source of the noise is unknown.

The terms "constant noise" and "constant background" as used herein are broad terms, and are to be given their ordinary and customary meaning to a person of ordinary skill in the art (and are not to be limited to a special or customized meaning), and refer without limitation to the component of the noise signal that remains relatively constant over time. In some embodiments, constant noise may be referred to as "background" or "baseline." For example, certain electroactive compounds found in the human body are relatively constant factors (e.g., baseline of the host's physiology). In some circumstances, constant background noise can slowly drift over time (e.g., increase or decrease), however this drift need not adversely affect the accuracy of a sensor, for example, because a sensor can be calibrated and re-calibrated and/or the drift measured and compensated for.

The terms "non-constant noise," "non-constant background," "noise event(s)," "noise episode(s)," "signal artifact(s)," "signal artifact event(s)," and "signal artifact episode(s)" as used herein are broad terms, and are to be given their ordinary and customary meaning to a person of ordinary skill in the art (and are not to be limited to a special or customized meaning), and refer without limitation to a component of the background signal that is relatively non-constant, for example, transient and/or intermittent. For example, certain electroactive compounds, are relatively non-constant due to the host's ingestion, metabolism, wound healing, and other mechanical, chemical and/or biochemical factors), which create intermittent (e.g., non-constant) "noise" on the sensor signal that can be difficult to "calibrate out" using a standard calibration equations (e.g., because the background of the signal does not remain constant).

The terms "low noise" as used herein is a broad term and is to be given its ordinary and customary meaning to a person of ordinary skill in the art (and is not to be limited to a special or customized meaning), and furthermore refers without limitation to noise that substantially decreases signal amplitude.

The terms "high noise" and "high spikes" as used herein are broad terms and are to be given their ordinary and customary meaning to a person of ordinary skill in the art (and are not to be limited to a special or customized meaning), and furthermore refer without limitation to noise that substantially increases signal amplitude.

The term "frequency content" as used herein is a broad term and is to be given its ordinary and customary meaning to a person of ordinary skill in the art (and is not to be limited to a special or customized meaning), and furthermore refers without limitation to the spectral density, including the frequencies contained within a signal and their power.

The term "spectral density" as used herein is a broad term and is to be given its ordinary and customary meaning to a person of ordinary skill in the art (and is not to be limited to a special or customized meaning), and furthermore refers without limitation to power spectral density of a given bandwidth of electromagnetic radiation is the total power in this bandwidth divided by the specified bandwidth. Spectral density is usually expressed in Watts per Hertz (W/Hz).

The term "chronoamperometry" as used herein is a broad term and is to be given its ordinary and customary meaning to a person of ordinary skill in the art (and is not to be limited to a special or customized meaning), and furthermore refers without limitation to an electrochemical measuring technique used for electrochemical analysis or for the determination of the kinetics and mechanism of electrode reactions. A fast-rising potential pulse is enforced on the working (or reference) electrode of an electrochemical cell and the current flowing through this electrode is measured as a function of time.

The term "pulsed amperometric detection" as used herein is a broad term and is to be given its ordinary and customary meaning to a person of ordinary skill in the art (and is not to be limited to a special or customized meaning), and furthermore refers without limitation to an electrochemical flow cell and a controller, which applies the potentials and monitors current generated by the electrochemical reactions. The cell can include one or multiple working electrodes at different applied potentials. Multiple electrodes can be arranged so that they face the chromatographic flow independently (parallel configuration), or sequentially (series configuration).

The term "linear regression" as used herein is a broad term and is to be given its ordinary and customary meaning to a person of ordinary skill in the art (and is not to be limited to a special or customized meaning), and furthermore refers without limitation to finding a line in which a set of data has a minimal measurement from that line. Byproducts of this algorithm include a slope, a y-intercept, and an R-Squared value that determine how well the measurement data fits the line.

The term "non-linear regression" as used herein is a broad term and is to be given its ordinary and customary meaning to a person of ordinary skill in the art (and is not to be limited to a special or customized meaning), and furthermore refers without limitation to fitting a set of data to describe the relationship between a response variable and one or more explanatory variables in a non-linear fashion.

The term "mean" as used herein is a broad term and is to be given its ordinary and customary meaning to a person of ordinary skill in the art (and is not to be limited to a special or customized meaning), and furthermore refers without limitation to the sum of the observations divided by the number of observations.

The term "trimmed mean" as used herein is a broad term and is to be given its ordinary and customary meaning to a person of ordinary skill in the art (and is not to be limited to a special or customized meaning), and furthermore refers without limitation to a mean taken after extreme values in the tails of a variable (e.g., highs and lows) are eliminated or reduced (e.g., "trimmed"). The trimmed mean compensates for sensitivities to extreme values by dropping a certain percentage of values on the tails. For example, the 50% trimmed mean is the mean of the values between the upper and lower quartiles. The 90% trimmed mean is the mean of the values after truncating the lowest and highest 5% of the values. In one example, two highest and two lowest measurements are removed from a data set and then the remaining measurements are averaged.

The term "non-recursive filter" as used herein is a broad term and is to be given its ordinary and customary meaning to a person of ordinary skill in the art (and is not to be limited to a special or customized meaning), and furthermore refers without limitation to an equation that uses moving averages as inputs and outputs.

The terms "recursive filter" and "auto-regressive algorithm" as used herein are broad terms and are to be given their ordinary and customary meaning to a person of ordinary skill in the art (and are not to be limited to a special or customized meaning), and furthermore refer without limitation to an equation in which includes previous averages are part of the next filtered output. More particularly, the generation of a series of observations whereby the value of each observation is partly dependent on the values of those that have immediately preceded it. One example is a regression structure in which lagged response values assume the role of the independent variables.

The term "signal estimation algorithm factors" as used herein is a broad term and is to be given its ordinary and customary meaning to a person of ordinary skill in the art (and is not to be limited to a special or customized meaning), and furthermore refers without limitation to one or more algorithms that use historical and/or present signal data stream values to estimate unknown signal data stream values. For example, signal estimation algorithm factors can include one or more algorithms, such as linear or non-linear regression. As another example, signal estimation algorithm factors can include one or more sets of coefficients that can be applied to one algorithm.

The term "variation" as used herein is a broad term and is to be given its ordinary and customary meaning to a person of ordinary skill in the art (and is not to be limited to a special or customized meaning), and furthermore refers without limitation to a divergence or amount of change from a point, line, or set of data. In one embodiment, estimated analyte values can have a variation including a range of values outside of the estimated analyte values that represent a range of possibilities based on known physiological patterns, for example.

The terms "physiological parameters" and "physiological boundaries" as used herein are broad terms and are to be given their ordinary and customary meaning to a person of ordinary skill in the art (and are not to be limited to a special or customized meaning), and furthermore refer without limitation to the parameters obtained from continuous studies of physiological data in humans and/or animals. For example, a maximal sustained rate of change of glucose in humans of about 4 to 5 mg/dL/min and a maximum acceleration of the rate of change of about 0.1 to 0.2 mg/dL/min$^2$ are deemed physiologically feasible limits; values outside of these limits would be considered non-physiological. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data. As a further example, it has been observed that the best solution for the shape of the curve at any point along glucose signal data stream over a certain time period (for example, about 20 to 30 minutes) is a straight line, which can be used to set physiological limits. These terms are broad enough to include physiological parameters for any analyte.

The term "measured analyte values" as used herein is a broad term and is to be given its ordinary and customary meaning to a person of ordinary skill in the art (and is not to be limited to a special or customized meaning), and furthermore refers without limitation to an analyte value or set of analyte values for a time period for which analyte data has been measured by an analyte sensor. The term is broad enough to include data from the analyte sensor before or after data processing in the sensor and/or receiver (for example, data smoothing, calibration, and the like).

The term "estimated analyte values" as used herein is a broad term and is to be given its ordinary and customary meaning to a person of ordinary skill in the art (and is not to be limited to a special or customized meaning), and furthermore refers without limitation to an analyte value or set of analyte values, which have been algorithmically extrapolated from measured analyte values.

The terms "interferants" and "interfering species" as used herein are broad terms and are to be given their ordinary and customary meaning to a person of ordinary skill in the art (and are not to be limited to a special or customized meaning), and furthermore refer without limitation to effects and/or species that interfere with the measurement of an analyte of interest in a sensor to produce a signal that does not accurately represent the analyte concentration. In one example of an electrochemical sensor, interfering species are compounds with an oxidation potential that overlap that of the analyte to be measured, thereby producing a false positive signal.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Overview/General Description of System

The glucose sensor can use any system or method to provide a data stream indicative of the concentration of glucose in a host. The data stream is typically a raw data signal that is transformed to provide a useful value of glucose to a user, such as a patient or doctor, who may be using the sensor. Faults may occur, however, which may be detectable by analysis of the signal, analysis of the clinical context, or both. Such faults require discrimination to distinguish the same from actual measured signal behavior, as well as for responsive signal processing, which can vary according to the fault. Accordingly, appropriate fault discrimination and responsive processing techniques are employed.

Glucose Sensor

The glucose sensor can be any device capable of measuring the concentration of glucose. One exemplary embodiment is described below, which utilizes an implantable glucose sensor. However, it should be understood that the devices and methods described herein can be applied to any device capable of detecting a concentration of glucose and providing an output signal that represents the concentration of glucose.

Exemplary embodiments disclosed herein relate to the use of a glucose sensor that measures a concentration of glucose or a substance indicative of the concentration or presence of another analyte. In some embodiments, the glucose sensor is a continuous device, for example a subcutaneous, transdermal, transcutaneous, non-invasive, intraocular and/or intravascular (e.g., intravenous) device. In some embodiments, the device can analyze a plurality of intermittent blood samples. The glucose sensor can use any method of glucose measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The glucose sensor can use any known detection method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

Although much of the description and examples are drawn to a glucose sensor capable of measuring the concentration of glucose in a host, the systems and methods of embodiments can be applied to any measurable analyte, a list of appropriate analytes noted above. Some exemplary embodiments described below utilize an implantable glucose sensor. However, it should be understood that the devices and methods described herein can be applied to any device capable of detecting a concentration of analyte and providing an output signal that represents the concentration of the analyte.

In one preferred embodiment, the analyte sensor is an implantable glucose sensor, such as described with reference to U.S. Pat. No. 6,001,067 and U.S. Patent Publication No. US-2005-0027463-A1. In another preferred embodiment, the analyte sensor is a transcutaneous glucose sensor, such as described with reference to U.S. Patent Publication No. US-2006-0020187-A1. In still other embodiments, the sensor is configured to be implanted in a host vessel or extracorporeally, such as is described in U.S. Patent Publication No. US-2007-0027385-A1, U.S. Patent Publication No. US-2008-0119703-A1, U.S. Patent Publication No. US-2008-0108942-A1, and U.S. Patent Publication No. US-2007-0197890-A1. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al.

The following description and examples described the present embodiments with reference to the drawings. In the drawings, reference numbers label elements of the present embodiments. These reference numbers are reproduced below in connection with the discussion of the corresponding drawing features.

Specific Description of System

FIG. 1A is an exploded perspective view of one exemplary embodiment comprising an implantable glucose sensor 10 that utilizes amperometric electrochemical sensor technology to measure glucose concentration. In this exemplary embodiment, a body 12 and head 14 house the electrodes 16 and sensor electronics, which are described in more detail below with reference to FIG. 2. Three electrodes 16 are operably connected to the sensor electronics (FIG. 2) and are covered by a sensing membrane 17 and a biointerface membrane 18, which are attached by a clip 19.

In one embodiment, the three electrodes 16, which protrude through the head 14, include a platinum working electrode, a platinum counter electrode, and a silver/silver chloride reference electrode. The top ends of the electrodes are in contact with an electrolyte phase (not shown), which is a free-flowing fluid phase disposed between the sensing membrane 17 and the electrodes 16. The sensing membrane 17 includes an enzyme, e.g., glucose oxidase, which covers the electrolyte phase. The biointerface membrane 18 covers the sensing membrane 17 and serves, at least in part, to protect the sensor 10 from external forces that can result in environmental stress cracking of the sensing membrane 17.

In the illustrated embodiment, the counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

$$Glucose + O_2 \rightarrow Gluconate + H_2O_2$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule ($O_2$).

Figure 1C:
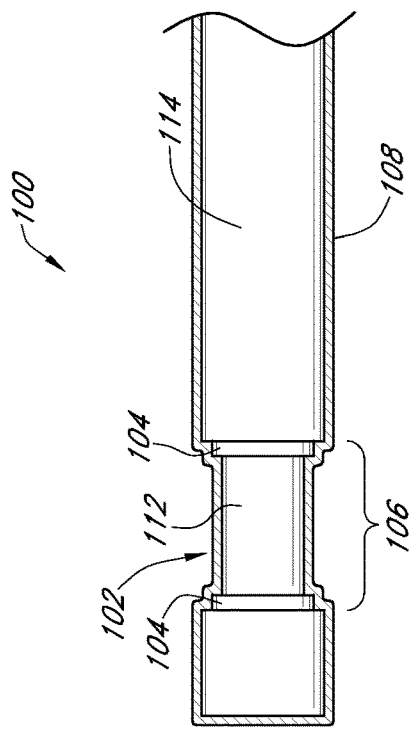
FIG. 1C is a side-view schematic illustrating a formed in vivo portion of an analyte sensor.
Figure 1B:
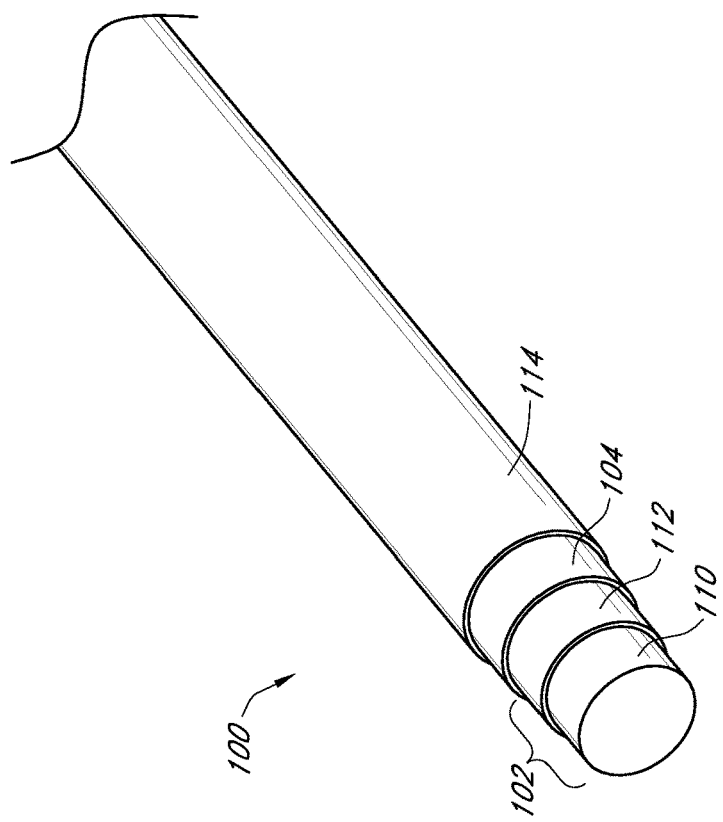
FIG. 1B is a perspective view schematic illustrating layers that form an in vivo portion of an analyte sensor, in one embodiment.

FIGS. 1B-1C illustrate one exemplary embodiment of an in vivo portion of a continuous analyte sensor 100, which includes an elongated conductive body 102. The elongated conductive body 102 includes a core 110 (see FIG. 1B) and a first layer 112 at least partially surrounding the core. The first layer includes a working electrode (e.g., located in window 106) and a membrane 108 located over the working electrode configured and arranged for multi-axis bending. In some embodiments, the core and first layer can be of a single material (e.g., platinum). In some embodiments, the elongated conductive body is a composite of at least two materials, such as a composite of two conductive materials, or a composite of at least one conductive material and at least one non-conductive material. In some embodiments, the elongated conductive body comprises a plurality of layers. In certain embodiments, there are at least two concentric (e.g., annular) layers, such as a core formed of a first material and a first layer formed of a second material. However, additional layers can be included in some embodiments. In some embodiments, the layers are coaxial.

The elongated conductive body may be long and thin, yet flexible and strong. For example, in some embodiments, the smallest dimension of the elongated conductive body is less than about 0.1 inches, 0.075 inches, 0.05 inches, 0.025 inches, 0.01 inches, 0.004 inches, or 0.002 inches. While the elongated conductive body is illustrated in FIGS. 1B-1C as having a circular cross-section, in other embodiments the cross-section of the elongated conductive body can be ovoid, rectangular, triangular, polyhedral, star-shaped, C-shaped, T-shaped, X-shaped, Y-Shaped, irregular, or the like. In one embodiment, a conductive wire electrode is employed as a core. To such a clad electrode, two additional conducting layers may be added (e.g., with intervening insulating layers provided for electrical isolation). The conductive layers can be comprised of any suitable material. In certain embodiments, it can be desirable to employ a conductive layer comprising conductive particles (i.e., particles of a conductive material) in a polymer or other binder.

In certain embodiments, the materials used to form the elongated conductive body (e.g., stainless steel, titanium, tantalum, platinum, platinum-iridium, iridium, certain polymers, and/or the like) can be strong and hard, and therefore are resistant to breakage. For example, in some embodiments, the ultimate tensile strength of the elongated conductive body is from about 80 kPsi to about 500 kPsi. In another example, in some embodiments, the Young's modulus of the elongated conductive body is from about 160 GPa to about 220 GPa. In still another example, in some embodiments, the yield strength of the elongated conductive body is from about 60 kPsi to about 2200 MPa. In some embodiments, the sensor's small diameter provides (e.g., imparts, enables) flexibility to these materials, and therefore to the sensor as a whole. Thus, the sensor can withstand repeated forces applied to it by surrounding tissue. In some embodiments, the fatigue life of the sensor is at least 1,000 cycles of flexing of from about 28° to about 110° at a bend radius of about 0.125-inches.

In addition to providing structural support, resiliency and flexibility, in some embodiments, the core 110 (or a component thereof) provides electrical conduction for an electrical signal from the working electrode to sensor electronics (FIG. 2), which are described elsewhere herein. In some embodiments, the core 110 comprises a conductive material, such as stainless steel, titanium, tantalum, a conductive polymer, and/or the like. However, in other embodiments, the core is formed from a non-conductive material, such as a non-conductive polymer. In yet other embodiments, the core comprises a plurality of layers of materials. For example, in one embodiment the core includes an inner core and an outer core. In a further embodiment, the inner core is formed of a first conductive material and the outer core is formed of a second conductive material. For example, in some embodiments, the first conductive material is stainless steel, titanium, tantalum, a conductive polymer, an alloy, and/or the like, and the second conductive material is conductive material selected to provide electrical conduction between the core and the first layer, and/or to attach the first layer to the core (e.g., if the first layer is formed of a material that does not attach well to the core material). In another embodiment, the core is formed of a non-conductive material (e.g., a non-conductive metal and/or a non-conductive polymer) and the first layer is a conductive material, such as stainless steel, titanium, tantalum, a conductive polymer, and/or the like. The core and the first layer can be of a single (or same) material, e.g., platinum. One skilled in the art appreciates that additional configurations are possible.

Referring again to FIGS. 1B-1C, in some embodiments, the first layer 112 is formed of a conductive material. The working electrode is an exposed portion of the surface of the first layer. Accordingly, the first layer is formed of a material configured to provide a suitable electroactive surface for the working electrode, a material such as but not limited to platinum, platinum-iridium, gold, palladium, iridium, graphite, carbon, a conductive polymer, an alloy and/or the like.

As illustrated in FIGS. 1B-1C, a second layer 104 surrounds a least a portion of the first layer 112, thereby defining the boundaries of the working electrode. In some embodiments, the second layer 104 serves as an insulator and is formed of an insulating material, such as polyimide, polyurethane, parylene, or any other known insulating materials. For example, in one embodiment the second layer is disposed on the first layer and configured such that the working electrode is exposed via window 106. In another embodiment, an elongated conductive body, including the core, the first layer and the second layer, is provided, and the working electrode is exposed (i.e., formed) by removing a portion of the second layer, thereby forming the window 106 through which the electroactive surface of the working electrode (e.g., the exposed surface of the first layer) is exposed. In some embodiments, the working electrode is exposed by (e.g., window 106 is formed by) removing a portion of the second and (optionally) third layers. Removal of coating materials from one or more layers of elongated conductive body (e.g., to expose the electroactive surface of the working electrode) can be performed by hand, excimer lasing, chemical etching, laser ablation, grit-blasting, or the like.

In some embodiments, the sensor further comprises a third layer 114 comprising a conductive material. In further embodiments, the third layer may comprise a reference electrode, which may be formed of a silver-containing material that is applied onto the second layer (e.g., an insulator). The silver-containing material may include any of a variety of materials and be in various forms, such as, Ag/AgCl-polymer pastes, paints, polymer-based conducting mixture, and/or inks that are commercially available, for example. The third layer can be processed using a pasting/dipping/coating step, for example, using a die-metered dip coating process. In one exemplary embodiment, an Ag/AgCl polymer paste is applied to an elongated body by dip-coating the body (e.g., using a meniscus coating technique) and then drawing the body through a die to meter the coating to a precise thickness. In some embodiments, multiple coating steps are used to build up the coating to a predetermined thickness. Such a drawing method can be utilized for forming one or more of the electrodes in the device depicted in FIG. 1B.

In some embodiments, the silver grain in the Ag/AgCl solution or paste can have an average particle size corresponding to a maximum particle dimension that is less than about 100 microns, or less than about 50 microns, or less than about 30 microns, or less than about 20 microns, or less than about 10 microns, or less than about 5 microns. The silver chloride grain in the Ag/AgCl solution or paste can have an average particle size corresponding to a maximum particle dimension that is less than about 100 microns, or less than about 80 microns, or less than about 60 microns, or less than about 50 microns, or less than about 20 microns, or less than about 10 microns. The silver grain and the silver chloride grain may be incorporated at a ratio of the silver chloride grain:silver grain of from about 0.01:1 to 2:1 by weight, or from about 0.1:1 to 1:1. The silver grains and the silver chloride grains are then mixed with a carrier (e.g., a polyurethane) to form a solution or paste. In certain embodiments, the Ag/AgCl component form from about 10% to about 65% by weight of the total Ag/AgCl solution or paste, or from about 20% to about 50%, or from about 23% to about 37%. In some embodiments, the Ag/AgCl solution or paste has a viscosity (under ambient conditions) that is from about 1 to about 500 centipoise, or from about 10 to about 300 centipoise, of from about 50 to about 150 centipoise.

In some embodiments, Ag/AgCl particles are mixed into a polymer, such as polyurethane, polyimide, or the like, to form the silver-containing material for the reference electrode. In some embodiments, the third layer is cured, for example, by using an oven or other curing process. In some embodiments, a covering of fluid-permeable polymer with conductive particles (e.g., carbon particles) therein is applied over the reference electrode and/or third layer. A layer of insulating material is located over a portion of the silver-containing material, in some embodiments.

In some embodiments, the elongated conductive body further comprises one or more intermediate layers located between the core and the first layer. For example, in some embodiments, the intermediate layer is an insulator, a conductor, a polymer, and/or an adhesive.

It is contemplated that the ratio between the thickness of the Ag/AgCl layer and the thickness of an insulator (e.g., polyurethane or polyimide) layer can be controlled, so as to allow for a certain error margin (e.g., an error margin resulting from the etching process) that would not result in a defective sensor (e.g., due to a defect resulting from an etching process that cuts into a depth more than intended, thereby unintentionally exposing an electroactive surface). This ratio may be different depending on the type of etching process used, whether it is laser ablation, grit blasting, chemical etching, or some other etching method. In one embodiment in which laser ablation is performed to remove a Ag/AgCl layer and a polyurethane layer, the ratio of the thickness of the Ag/AgCl layer and the thickness of the polyurethane layer can be from about 1:5 to about 1:1, or from about 1:3 to about 1:2.

In certain embodiment, the core comprises a non-conductive polymer and the first layer comprises a conductive material. Such a sensor configuration can sometimes provide reduced material costs, in that it replaces a typically expensive material with an inexpensive material. For example, in some embodiments, the core is formed of a non-conductive polymer, such as, a nylon or polyester filament, string or cord, which can be coated and/or plated with a conductive material, such as platinum, platinum-iridium, gold, palladium, iridium, graphite, carbon, a conductive polymer, and allows or combinations thereof.

As illustrated in FIG. 1C, the sensor also includes a membrane 108 covering at least a portion of the working electrode.

In embodiments wherein an outer insulator is disposed, a portion of the coated assembly structure can be stripped or otherwise removed, for example, by hand, excimer lasing, chemical etching, laser ablation, grit-blasting, or the like, to expose the electroactive surfaces. Alternatively, a portion of the electrode can be masked prior to depositing the insulator in order to maintain an exposed electroactive surface area.

In some embodiments, a radial window is formed through the insulating material to expose a circumferential electroactive surface of the working electrode. Additionally, sections of electroactive surface of the reference electrode are exposed. For example, the sections of electroactive surface can be masked during deposition of an outer insulating layer or etched after deposition of an outer insulating layer. In some applications, cellular attack or migration of cells to the sensor can cause reduced sensitivity or function of the device, particularly after the first day of implantation. However, when the exposed electroactive surface is distributed circumferentially about the sensor (e.g. as in a radial window), the available surface area for reaction can be sufficiently distributed so as to minimize the effect of local cellular invasion of the sensor on the sensor signal. Alternatively, a tangential exposed electroactive window can be formed, for example, by stripping only one side of the coated assembly structure. In other alternative embodiments, the window can be provided at the tip of the coated assembly structure such that the electroactive surfaces are exposed at the tip of the sensor. Other methods and configurations for exposing electroactive surfaces can also be employed.

In some alternative embodiments, additional electrodes can be included within the assembly, for example, a three-electrode system (working, reference, and counter electrodes) and an additional working electrode (e.g. an electrode which can be used to generate oxygen, which is configured as a baseline subtracting electrode, or which is configured for measuring additional analytes). U.S. Pat. No. 7,081,195, U.S. Patent Publication No. US-2005-0143635-

A1 and U.S. Patent Publication No. US-2007-0027385-A1, each of which are incorporated herein by reference, describe some systems and methods for implementing and using additional working, counter, and reference electrodes. In one implementation wherein the sensor comprises two working electrodes, the two working electrodes are juxtapositioned, around which the reference electrode is disposed (e.g. helically wound). In some embodiments wherein two or more working electrodes are provided, the working electrodes can be formed in a double-, triple-, quad-, etc. helix configuration along the length of the sensor (for example, surrounding a reference electrode, insulated rod, or other support structure). The resulting electrode system can be configured with an appropriate membrane system, wherein the first working electrode is configured to measure a first signal comprising glucose and baseline signals, and the additional working electrode is configured to measure a baseline signal consisting of the baseline signal only. In these embodiments, the second working electrode may be configured to be substantially similar to the first working electrode, but without an enzyme disposed thereon. In this way, the baseline signal can be determined and subtracted from the first signal to generate a difference signal, i.e., a glucose-only signal that is substantially not subject to fluctuations in the baseline or interfering species on the signal, such as described in U.S. Patent Publication No. US-2005-0143635-A1, U.S. Patent Publication No. US-2007-0027385-A1, and U.S. Patent Publication No. US-2007-0213611-A1, and U.S. Patent Publication No. US-2008-0083617-A1, which are incorporated herein by reference in their entirety.

It has been found that in some electrode systems involving two working electrodes, i.e., in some dual-electrode systems, the working electrodes may sometimes be slightly different from each other. For instance, two working electrodes, even when manufactured from a single facility may slightly differ in thickness or permeability because of the electrodes' high sensitivity to environmental conditions (e.g. temperature, humidity) during fabrication. Accordingly, the working electrodes of a dual-electrode system may sometimes have varying diffusion, membrane thickness, and diffusion characteristics. As a result, the above-described difference signal (i.e., a glucose-only signal, generated from subtracting the baseline signal from the first signal) may not be completely accurate. To mitigate this, it is contemplated that in some dual-electrode systems, both working electrodes may be fabricated with one or more membranes that each includes a bioprotective layer, which is described in more detail elsewhere herein.

It is contemplated that the sensing region may include any of a variety of electrode configurations. For example, in some embodiments, in addition to one or more glucose-measuring working electrodes, the sensing region may also include a reference electrode or other electrodes associated with the working electrode. In these particular embodiments, the sensing region may also include a separate reference or counter electrode associated with one or more optional auxiliary working electrodes. In other embodiments, the sensing region may include a glucose-measuring working electrode, an auxiliary working electrode, two counter electrodes (one for each working electrode), and one shared reference electrode. In yet other embodiments, the sensing region may include a glucose-measuring working electrode, an auxiliary working electrode, two reference electrodes, and one shared counter electrode.

U.S. Patent Publication No. US-2008-0119703-A1 and U.S. Patent Publication No. US-2005-0245799-A1 describe additional configurations for using the continuous sensor in different body locations. In some embodiments, the sensor is configured for transcutaneous implantation in the host. In alternative embodiments, the sensor is configured for insertion into the circulatory system, such as a peripheral vein or artery. However, in other embodiments, the sensor is configured for insertion into the central circulatory system, such as but not limited to the vena cava. In still other embodiments, the sensor can be placed in an extracorporeal circulation system, such as but not limited to an intravascular access device providing extracorporeal access to a blood vessel, an intravenous fluid infusion system, an extracorporeal blood chemistry analysis device, a dialysis machine, a heart-lung machine (i.e., a device used to provide blood circulation and oxygenation while the heart is stopped during heart surgery), etc. In still other embodiments, the sensor can be configured to be wholly implantable, as described in U.S. Pat. No. 6,001,067.

Figure 2:
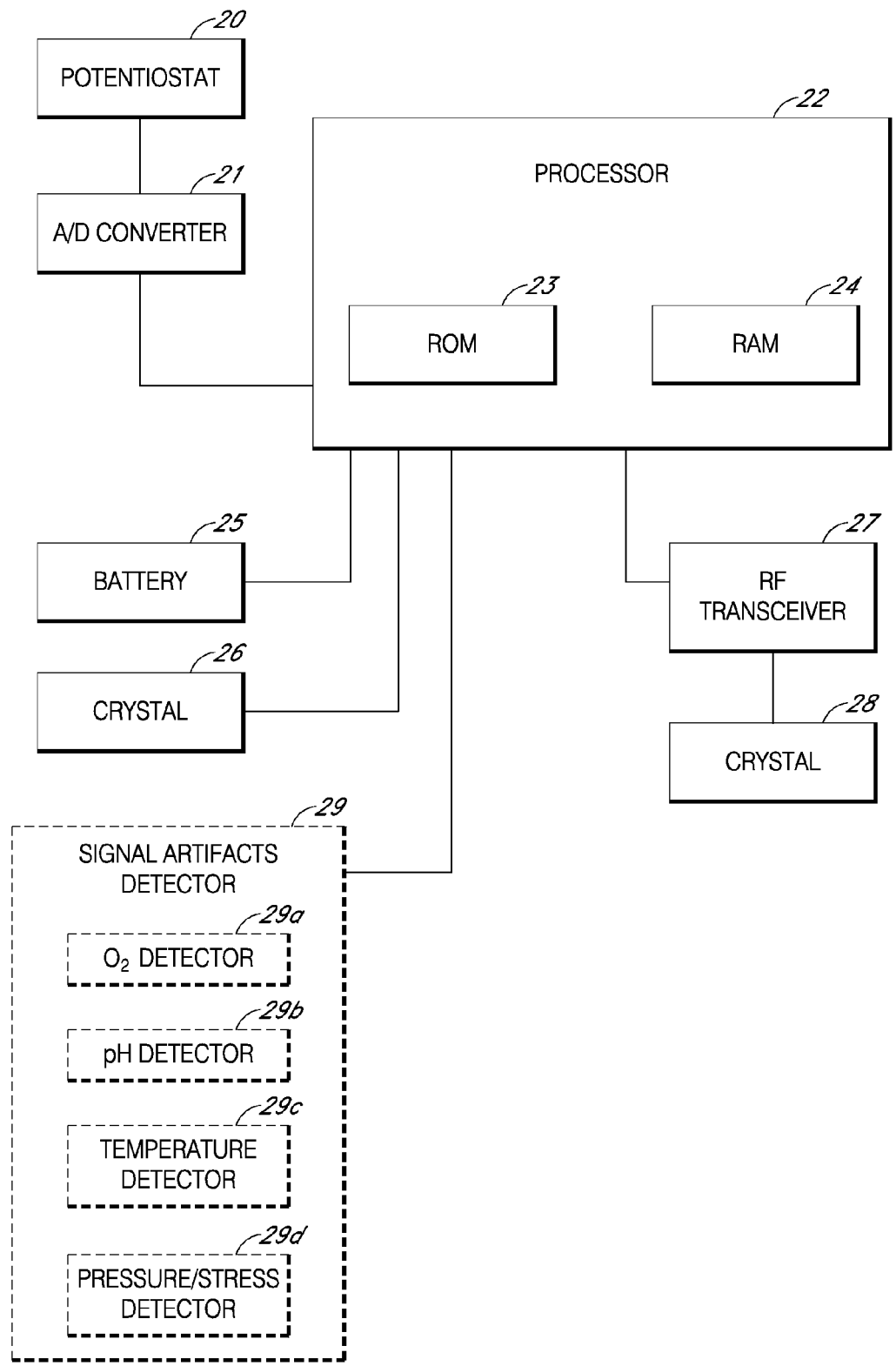
FIG. 2 is a block diagram that illustrates sensor electronics in one embodiment.

FIG. 2 is a block diagram that illustrates one possible configuration of the sensor electronics in one embodiment. In this embodiment, a potentiostat 20 is shown, which is operatively connected to an electrode system and provides a voltage to the electrodes, which biases the sensor to enable measurement of a current value indicative of the analyte concentration in the host (also referred to as the analog portion). In some embodiments, the potentiostat includes a resistor (not shown) that translates the current into voltage. In some alternative embodiments, a current to frequency converter is provided that is configured to continuously integrate the measured current, for example, using a charge counting device. In the illustrated embodiment, an A/D converter 21 digitizes the analog signal into "counts" for processing. Accordingly, the resulting raw data stream in counts is directly related to the current measured by the potentiostat 20.

A processor module 22 is the central control unit that controls the processing of the sensor electronics. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in more detail elsewhere herein). The processor additionally can be used for the system's cache memory, for example for temporarily storing recent sensor data. In some embodiments, the processor module comprises memory storage components such as various types of ROM, RAM, flash memory, and the like. In one exemplary embodiment, ROM 23 provides semi-permanent storage of data, for example, storing data such as sensor identifier (ID) and programming to process data streams (e.g., programming for signal artifacts detection and/or replacement such as described elsewhere herein). In one exemplary embodiment, RAM 24 can be used for the system's cache memory, for example for temporarily storing recent sensor data.

In some embodiments, the processor module comprises a digital filter, for example, an IIR or FIR filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in optimizing noise filtration, time lag, and processing/battery power.

Preferably, the processor module is configured to build the data packet for transmission to an outside source, for example, an RF transmission to a receiver as described in more detail below. Generally, the data packet comprises a plurality of bits that can include a sensor ID code, raw data, filtered data, and/or error detection or correction. The processor module can be configured to transmit any combination of raw and/or filtered data.

A battery 25 is operatively connected to the processor 22 and provides the necessary power for the sensor (e.g., 100). In one embodiment, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some embodiments the battery is rechargeable. In some embodiments, a plurality of batteries can be used to power the system. In yet other embodiments, the receiver can be transcutaneously powered via an inductive coupling, for example. A Quartz Crystal 26 is operatively connected to the processor 22 and maintains system time for the computer system as a whole.

Figure 3A:
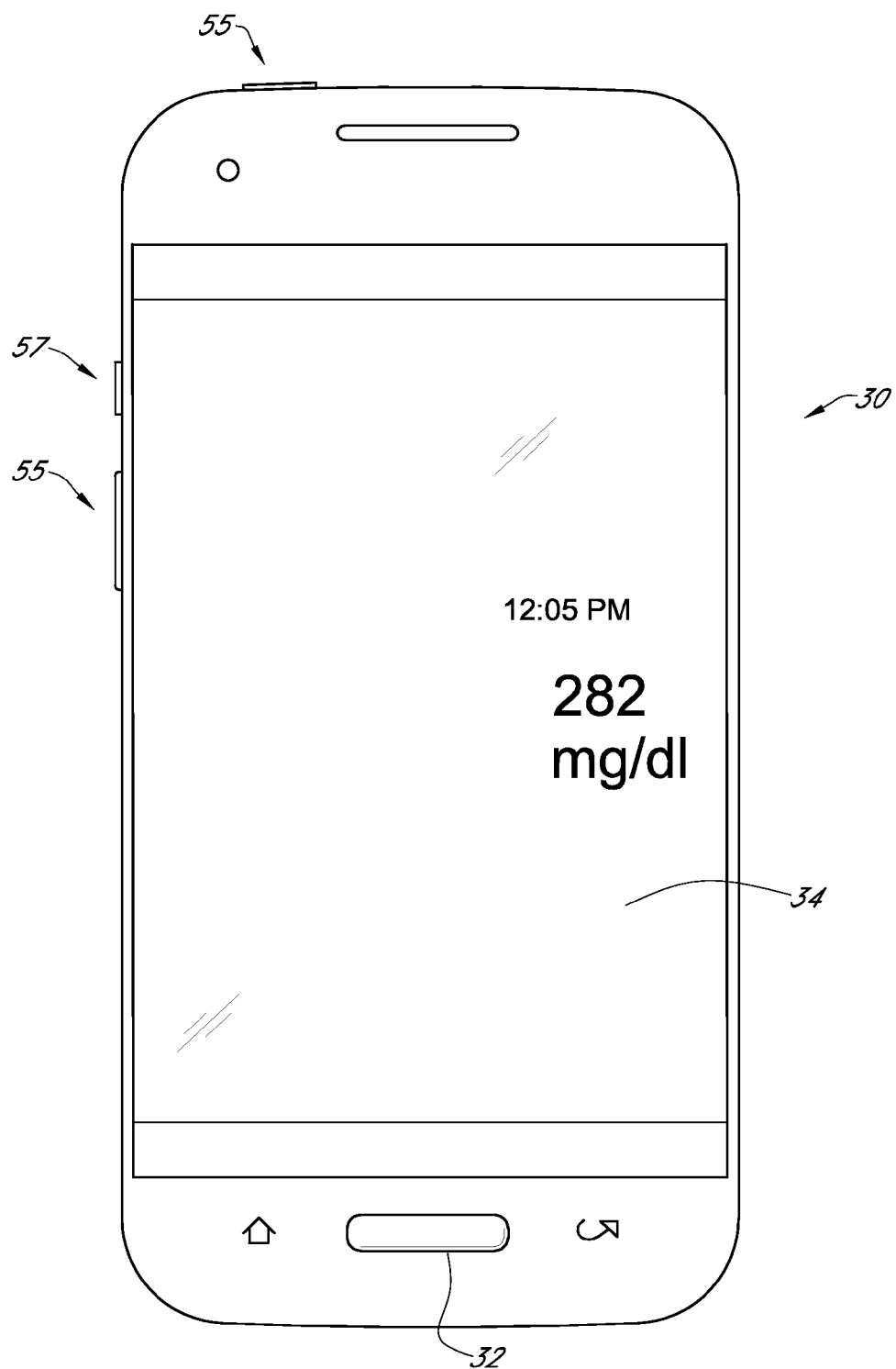
FIGS. 3A-3D are schematic views of a receiver in first, second, third, and fourth embodiments, respectively.
Figure 3B:
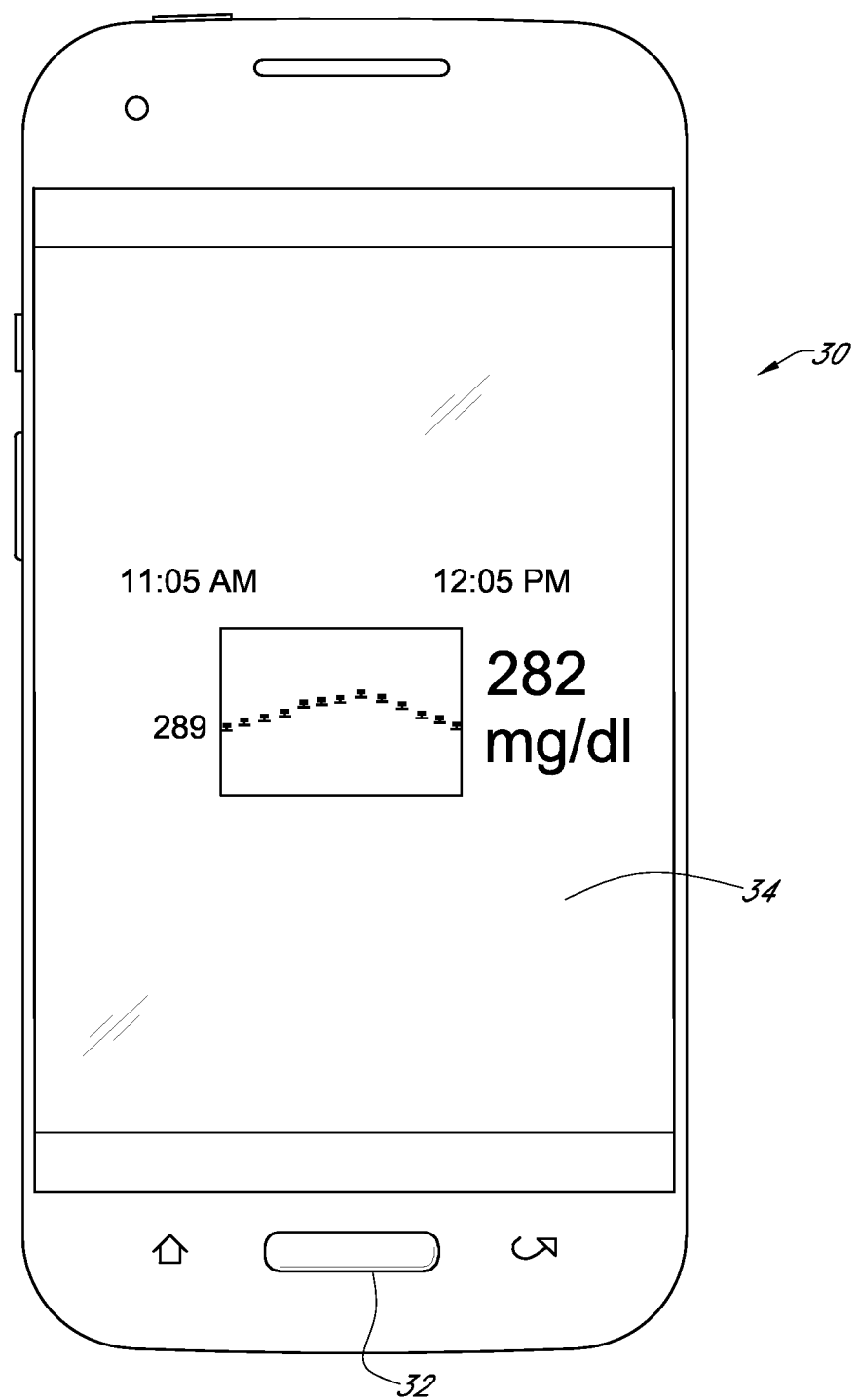
Figure 3C:
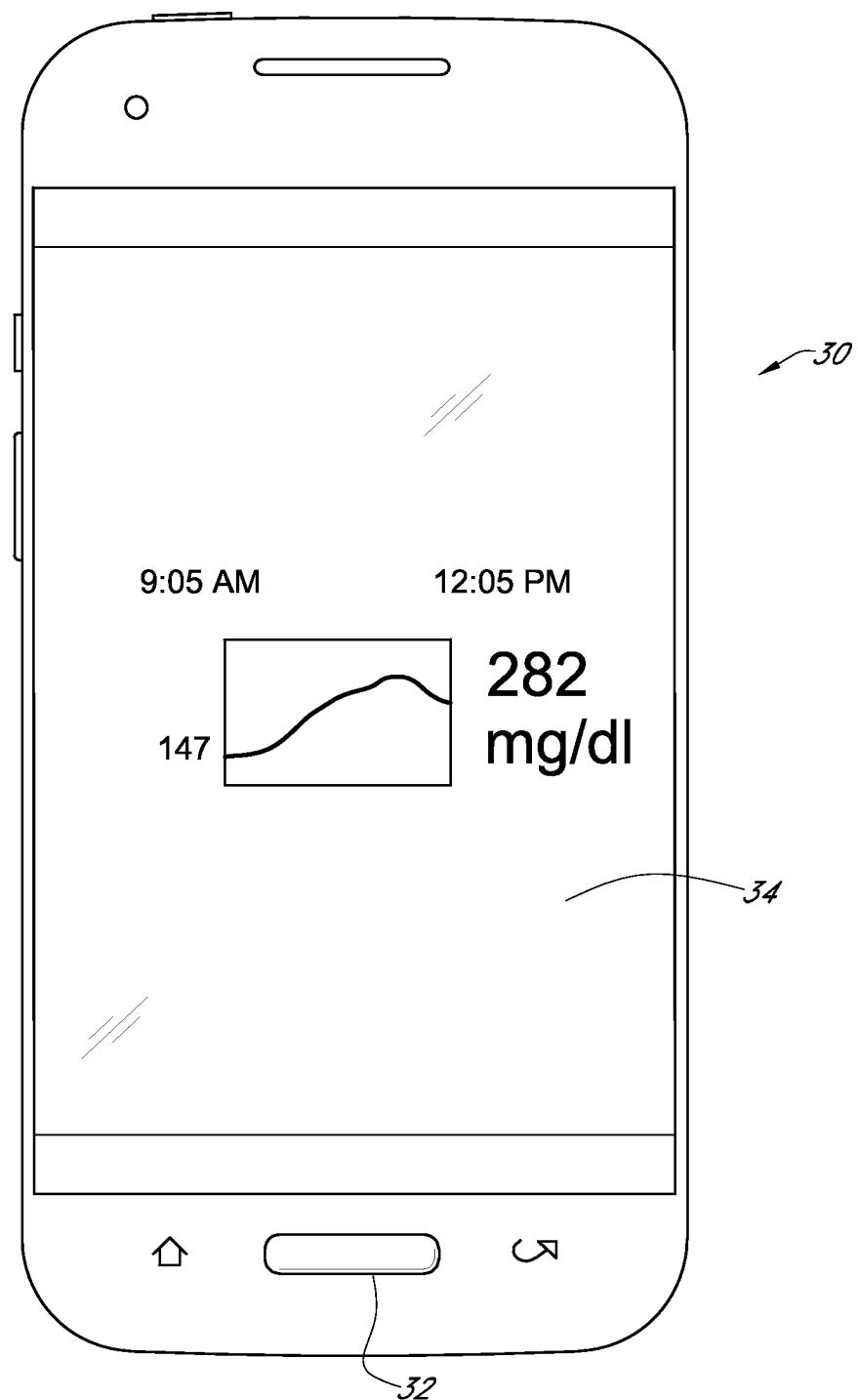
Figure 3D:
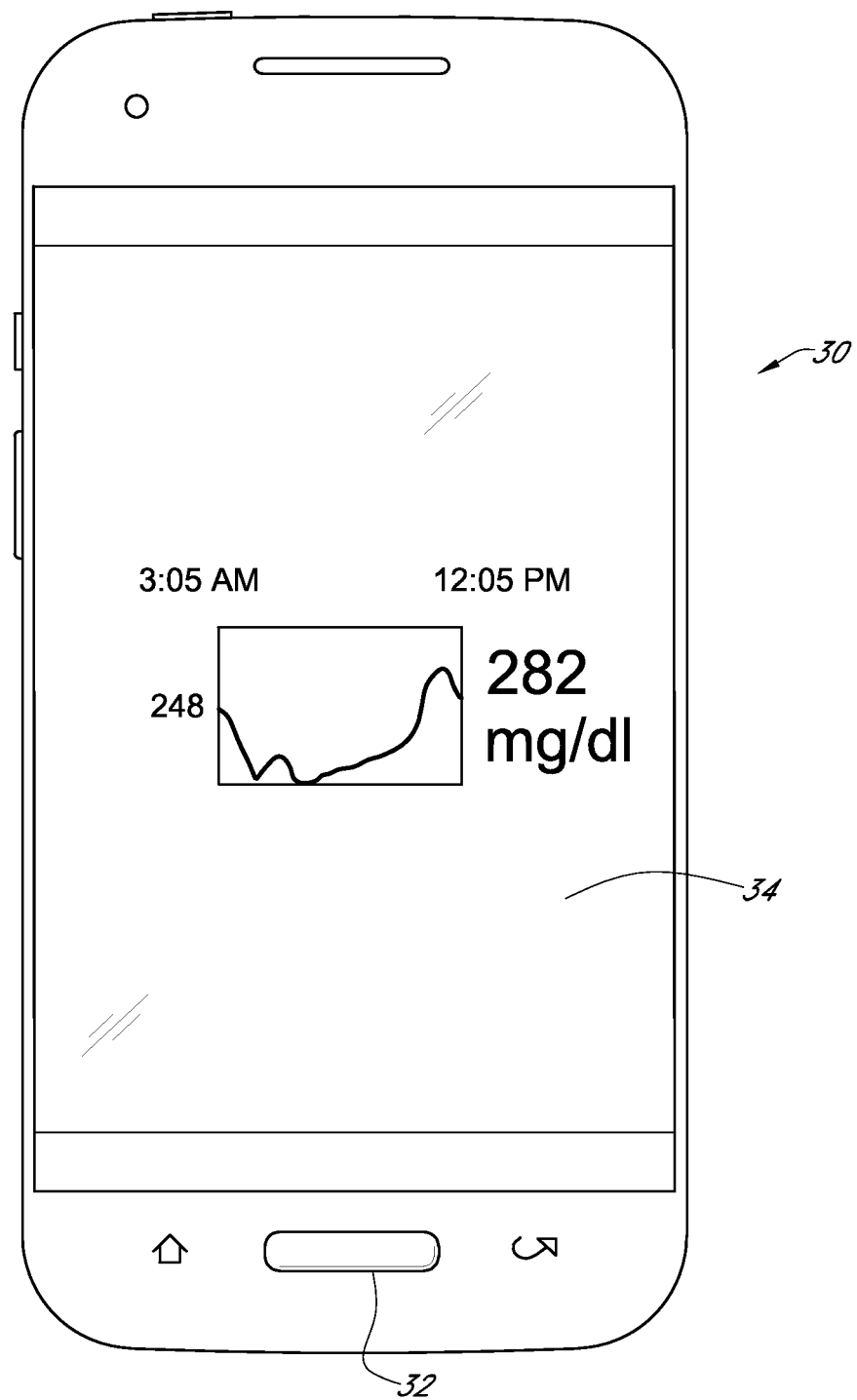
Figure 4:
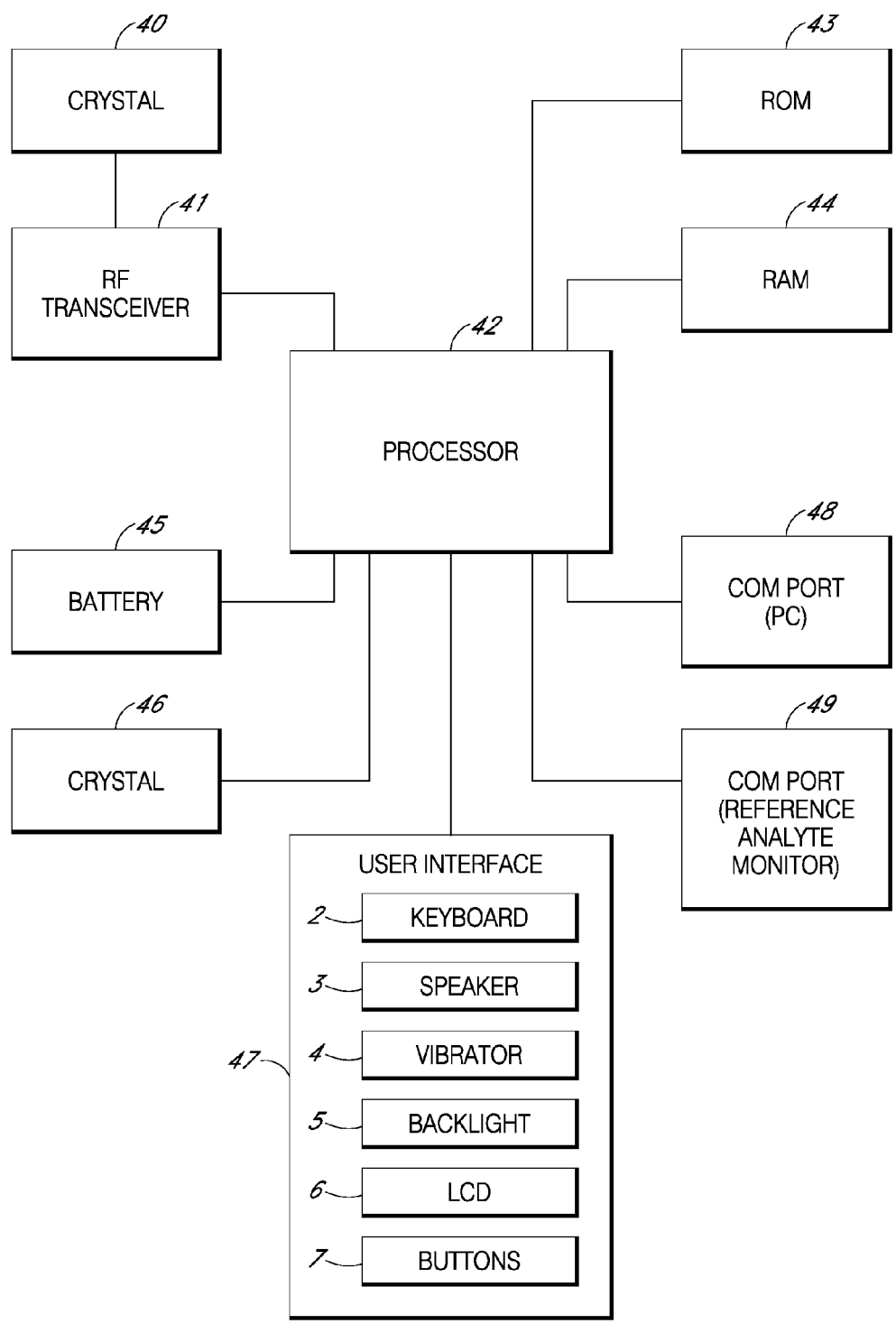
FIG. 4 is a block diagram of receiver electronics in one embodiment.

An RF module, (e.g., an RF Transceiver) 27 is operably connected to the processor 22 and transmits the sensor data from the sensor (e.g., 100) to a receiver (see FIGS. 3 and 4). Although an RF transceiver is shown here, some other embodiments can include a wired rather than wireless connection to the receiver. A second quartz crystal 28 provides the system time for synchronizing the data transmissions from the RF transceiver. It is noted that the transceiver 27 can be substituted with a transmitter in other embodiments. In some alternative embodiments, however, other mechanisms, such as optical, infrared radiation (IR), ultrasonic, and the like, can be used to transmit and/or receive data.

In some embodiments, a Signal Artifacts Detector 29 is provided that includes one or more of the following: an oxygen detector 29a, a pH detector 29b, a temperature detector 29c, and a pressure/stress detector 29d, which is described in more detail with reference to signal artifacts and faults/errors detection and discrimination. It is noted that in some embodiments the signal artifacts detector 29 is a separate entity (e.g., temperature detector) operatively connected to the processor, while in other embodiments, the signal artifacts detector is a part of the processor and utilizes readings from the electrodes, for example, to detect signal faults and artifacts. Although the above description includes some embodiments in which all discrimination occurs within the sensor, other embodiments provide for systems and methods for detecting signal faults in the sensor and/or receiver electronics (e.g., processor module) as described in more detail elsewhere herein.

Receiver

FIGS. 3A to 3D are schematic views of a receiver 30 including representations of estimated glucose values on its user interface in first, second, third, and fourth embodiments, respectively. The receiver 30 comprises systems to receive, process, and display sensor data from the glucose sensor (e.g., 100), such as described herein. Particularly, the receiver 30 can be a mobile phone type device, for example, and comprise a user interface that has a physical button 32 and a display screen 34, as well as one or more input/output (I/O) devices, such as one or more buttons 55 and/or switches 57, which when activated or clicked perform one or more functions. In the illustrated embodiment, the electronic device is a smartphone, and the display 34 comprises a touchscreen, which also functions as an I/O device. In some embodiments, the user interface can also include a keyboard, a speaker, and a vibrator. The functions of the receiver or smart phone can also be implemented as functions within an application running on a tablet computer, or like device. In other embodiments, the receiver may comprise a device or devices other than a smartphone, such as a smartwatch, a tablet computer, a mini-tablet computer, a handheld personal digital assistant (PDA), a game console, a multimedia player, a wearable device, such as those described above, a screen in an automobile or other vehicle, a dedicated receiver device, etc.

FIG. 3A illustrates a first embodiment where the receiver 30 shows a numeric representation of the estimated glucose value on its user interface. FIG. 3B illustrates a second embodiment where the receiver 30 shows an estimated glucose value and approximately one hour of historical trend data on its user interface. FIG. 3C illustrates a third embodiment where the receiver 30 shows an estimated glucose value and approximately three hours of historical trend data on its user interface. FIG. 3D illustrates a fourth embodiment where the receiver 30 shows an estimated glucose value and approximately nine hours of historical trend data on its user interface. In some embodiments, a user can toggle through some or all of the screens shown in FIGS. 3A to 3D using a physical button or a button implemented on a touch screen interface. In some embodiments, the user will be able to interactively select the type of output displayed on their user interface. In other embodiments, the sensor output can have alternative configurations.

FIG. 4 is a block diagram that illustrates one possible configuration of the receiver, e.g., a smart phone, electronics. It is noted that the receiver can comprise a configuration such as described with reference to FIGS. 3A to 3D, above. Alternatively, the receiver can comprise other configurations, including a desktop computer, laptop computer, a personal digital assistant (PDA), a server (local or remote to the receiver), and the like. In some embodiments, the receiver can be adapted to connect (via wired or wireless connection) to a desktop computer, laptop computer, PDA, server (local or remote to the receiver), and the like, in order to download data from the receiver. In some alternative embodiments, the receiver and/or receiver electronics can be housed within or directly connected to the sensor (e.g., 100) in a manner that allows sensor and receiver electronics to work directly together and/or share data processing resources. Accordingly, the receiver's electronics (or any combination of sensor and/or receiver electronics) can be generally referred to as a "computer system."

A quartz crystal 40 is operatively connected to an RF transceiver 41 that together function to receive and synchronize data streams (e.g., raw data streams transmitted from the RF transceiver). Once received, a processor 42 processes the signals, such as described below.

The processor 42, also referred to as the processor module, is the central control unit that performs the processing, such as storing data, analyzing data streams, calibrating analyte sensor data, predicting analyte values, comparing predicted analyte values with corresponding measured analyte values, analyzing a variation of predicted analyte values, downloading data, and controlling the user interface by providing analyte values, prompts, messages, warnings, alarms, and the like. The processor includes hardware and software that performs the processing described herein, for example flash memory provides permanent or semi-permanent storage of data, storing data such as sensor ID, receiver ID, and programming to process data streams (for example, programming for performing prediction and other algorithms described elsewhere herein) and random access memory (RAM) stores the system's cache memory and is helpful in data processing.

In one exemplary embodiment, the processor is a microprocessor that provides the processing, such as calibration algorithms stored within a ROM 43. The ROM 43 is operatively connected to the processor 42 and provides semi-permanent storage of data, storing data such as receiver ID and programming to process data streams (e.g., programming for performing calibration and other algorithms described elsewhere herein). In this exemplary embodiment, a RAM 44 is used for the system's cache memory and is helpful in data processing.

A battery 45 is operatively connected to the processor 42 and provides power for the receiver. In one embodiment, the battery is a standard AAA alkaline battery, however any appropriately sized and powered battery can be used. In some embodiments, a plurality of batteries can be used to power the system. A quartz crystal 46 is operatively connected to the processor 42 and maintains system time for the computer system as a whole.

A user interface 47 comprises a keyboard 2, speaker 3, vibrator 4, backlight 5, liquid crystal display (LCD 6), and one or more buttons 7, which may be implemented as physical buttons or buttons on a touchscreen interface. The components that comprise the user interface 47 provide controls to interact with the user. The keyboard 2 can allow, for example, input of user information about himself/herself, such as mealtime, exercise, insulin administration, and reference glucose values. The speaker 3 can provide, for example, audible signals or alerts for conditions such as present and/or predicted hyper- and hypoglycemic conditions. The vibrator 4 can provide, for example, tactile signals or alerts for reasons such as described with reference to the speaker, above. The backlight 5 can be provided, for example, to aid the user in reading the LCD in low light conditions. The LCD 6 can be provided, for example, to provide the user with visual data output such as is illustrated in FIGS. 3A to 3D. The buttons 7 can provide for toggle, menu selection, option selection, mode selection, and reset, for example.

In some embodiments, prompts or messages can be displayed on the user interface to convey information to the user, such as requests for reference analyte values, therapy recommendations, deviation of the measured analyte values from the predicted analyte values, and the like. Additionally, prompts can be displayed to guide the user through calibration or trouble-shooting of the calibration.

In some implementations, the continuous analyte sensor system includes a Dexcom G4® Platinum glucose sensor and transmitter commercially available from Dexcom, Inc., for continuously monitoring a host's glucose levels.

In some embodiments, the system may execute various applications, for example, a CGM application, which may be downloaded to the receiver or other electronic device over the Internet and/or a cellular network, and the like. Data for various applications may be shared between the device and one or more other devices/systems, and stored by cloud or network storage and/or on one or more other devices/systems. This CGM application may include a fault discrimination and responsive processing module and/or may include processing sufficient to operate fault discrimination and remediation functions and methods as described below.
Introduction to Fault Discrimination and Responsive Processing Based on Data and Context Referring to FIG. 5, a flowchart 50 illustrates a general method according to present principles. The method generally involves reception of a signal from a monitoring device, such as from an analyte concentration monitor, e.g., a CGM (step 52). This signal may be "raw", in the sense that the same represents a number of counts and on which little or no significant processing has occurred. The method also involves reception of clinical context information (step 54), which is generally information about the patient environment and clinical setting. For example, for diabetes management, appropriate clinical context information may include meals ingested, insulin delivered, patient exercise, patient temperature, clinical glucose value (as distinguished from the raw signal value), and the like. Faults are then detected based on the signal, the clinical context, or both, and one or both may further play a role in responsive processing.

Appropriate fault discrimination is important in the prevention of inaccurate clinical glucose values, especially as displayed to a user. Inaccurate values may cause the user to take inappropriate actions, they may deteriorate the performance of predictive algorithms or closed loop algorithms, and they deteriorate the user's trust of their CGM sensor.

In a method according to present principles, a fault is then detected, determined or discriminated (step 56), collectively "discriminated". The fault may be discriminated solely on the basis of the received signal, or on the basis of both the received signal and the received clinical context. Responsive processing may then occur (step 58), and the same may be based on the discriminated fault and on the clinical context as separate variables or parameters, or on just the discriminated fault (in which the clinical context played a role in the discrimination). In a special case of the method, the received signal, or the received signal and clinical context data, may be employed to discriminate a category of fault, and responsive processing may occur based on the category of fault. Other special cases will also be understood. These general principles are now described in greater detail, along with examples.

Received Signal and Clinical Context

As noted above, systems and methods according to present principles generally base fault discrimination and responsive processing methods on one or more received signals, one of which is generally related to a raw sensor signal such as an analyte concentration, e.g., glucose concentration, as well as on data about a clinical context, e.g., other physiological data about the patient, data about the patient environment (activity level, patterns, time of day, and the like). Each of these aspects is described in greater detail below.

Sensor Signal Analysis/Other Signals

FIG. 6 illustrates aspects of a received signal 62, as well as ways of discriminating the signal. First, the fault discrimination and responsive processing methods may be based on a raw signal 64, which is measured by the sensor electrode and is in the form of an uncalibrated number of counts with respect to time.

Second, the methods may be based on a processed raw signal 66, but where the processing is unrelated or preliminary to determining the analyte concentration value as used in a clinical value determination. In other words, the processing is unrelated or only preliminary to translating the raw signal counts into meaningful units for patient management, e.g., diabetes management, e.g., as a value expressed in mg/dL or mmol/L. Put yet another way, the processed raw signal is uncalibrated and by itself is not useful for clinical value determination.

The processing performed on the signal 66 is performed because aberrations can occur in the signal due to non-glucose related artifacts. Simple averaging or other processes cannot always grid the signal of such artifacts without losing important glucose concentration data in the signal itself.

One example of signal processing unrelated to transformation of the raw signal into a clinical value includes processing related to noise filtering. Such processing results in a signal 68 in which noise has been filtered out to a greater or lesser degree. Various aspects of noise filtering are described in greater detail below. Details of particular processing steps for noise filtering are provided in U.S. Pat. No. 8,260,393, issued Sep. 4, 2012, owned by the assignee of the present application and herein incorporated by reference in its entirety.

Figure 6A:
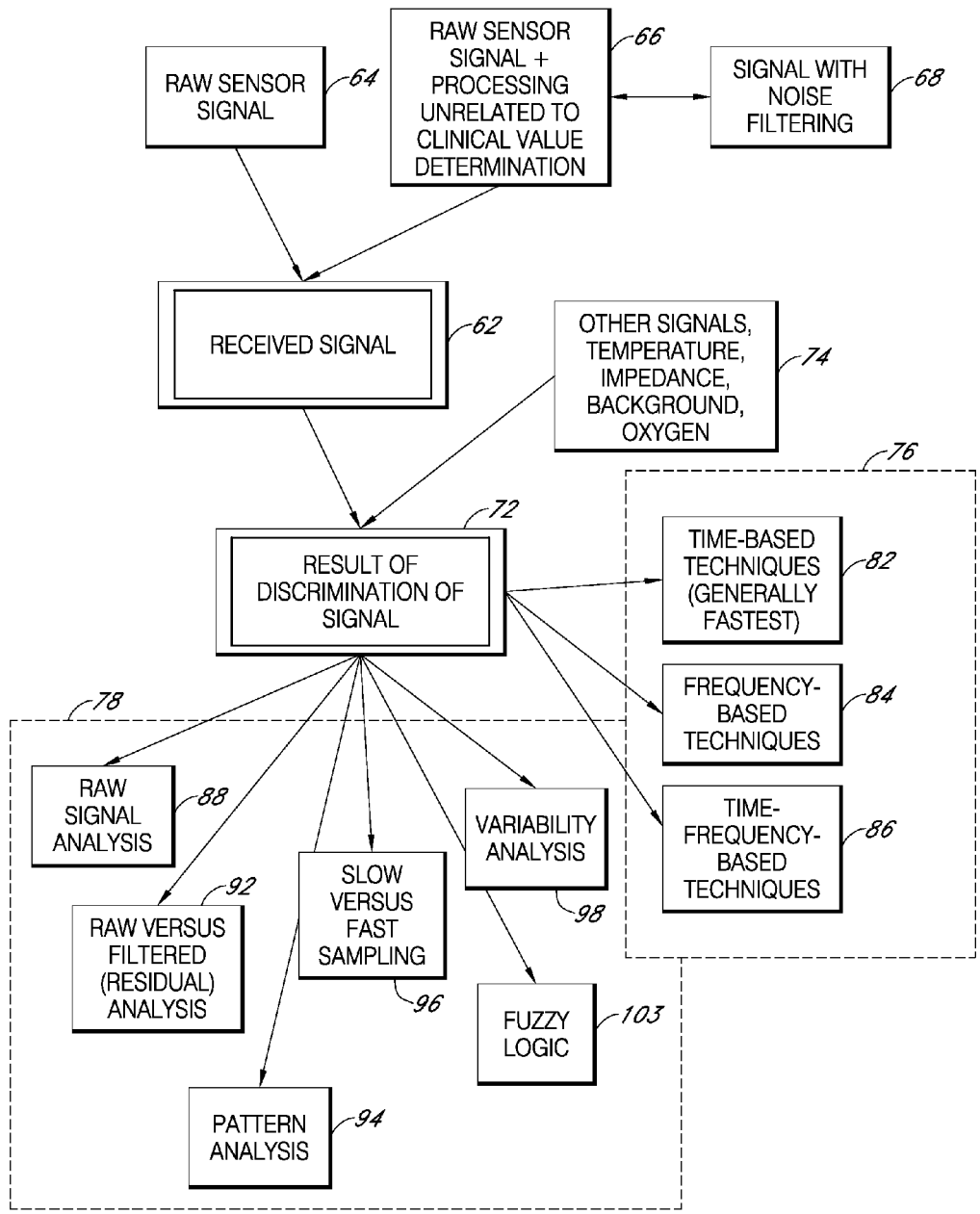
FIG. 6A is a more detailed flowchart of a method according to present principles, showing in particular types of signals and methods of performing responsive signal processing.
Figure 6C:
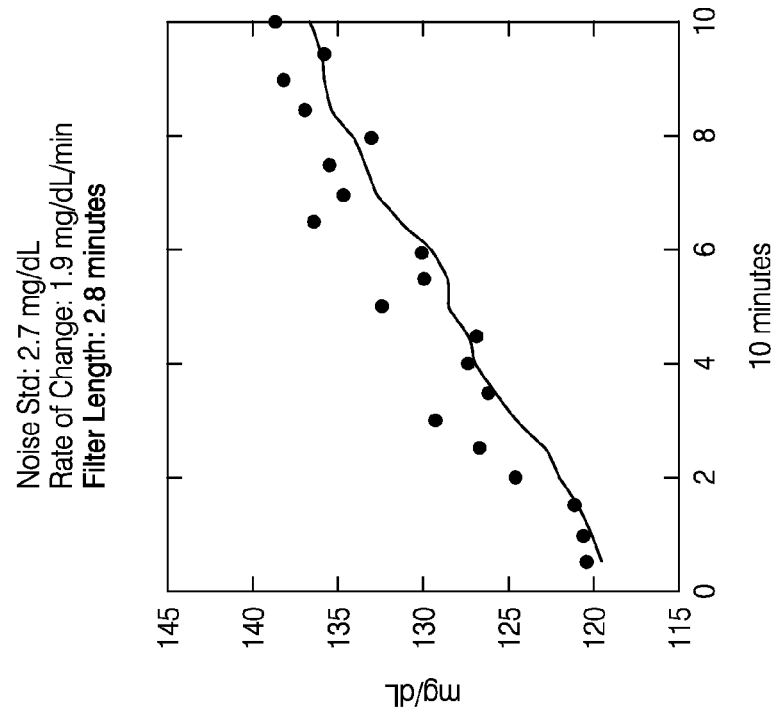
FIGS. 6B-6D are plots indicating types of noise filtering.
Figure 6B:
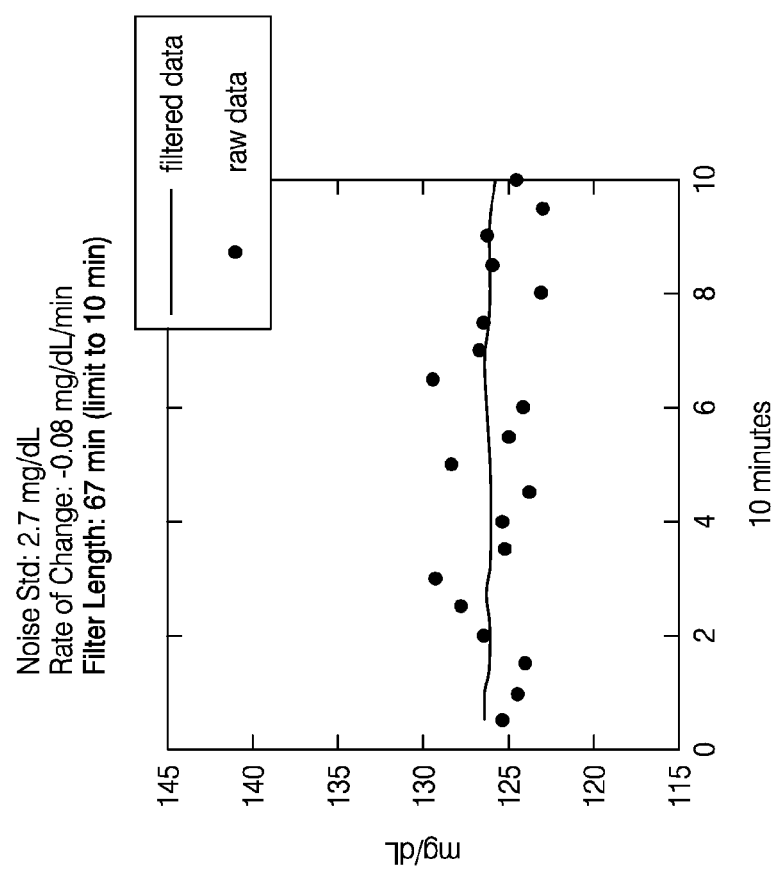
Figure 6D:
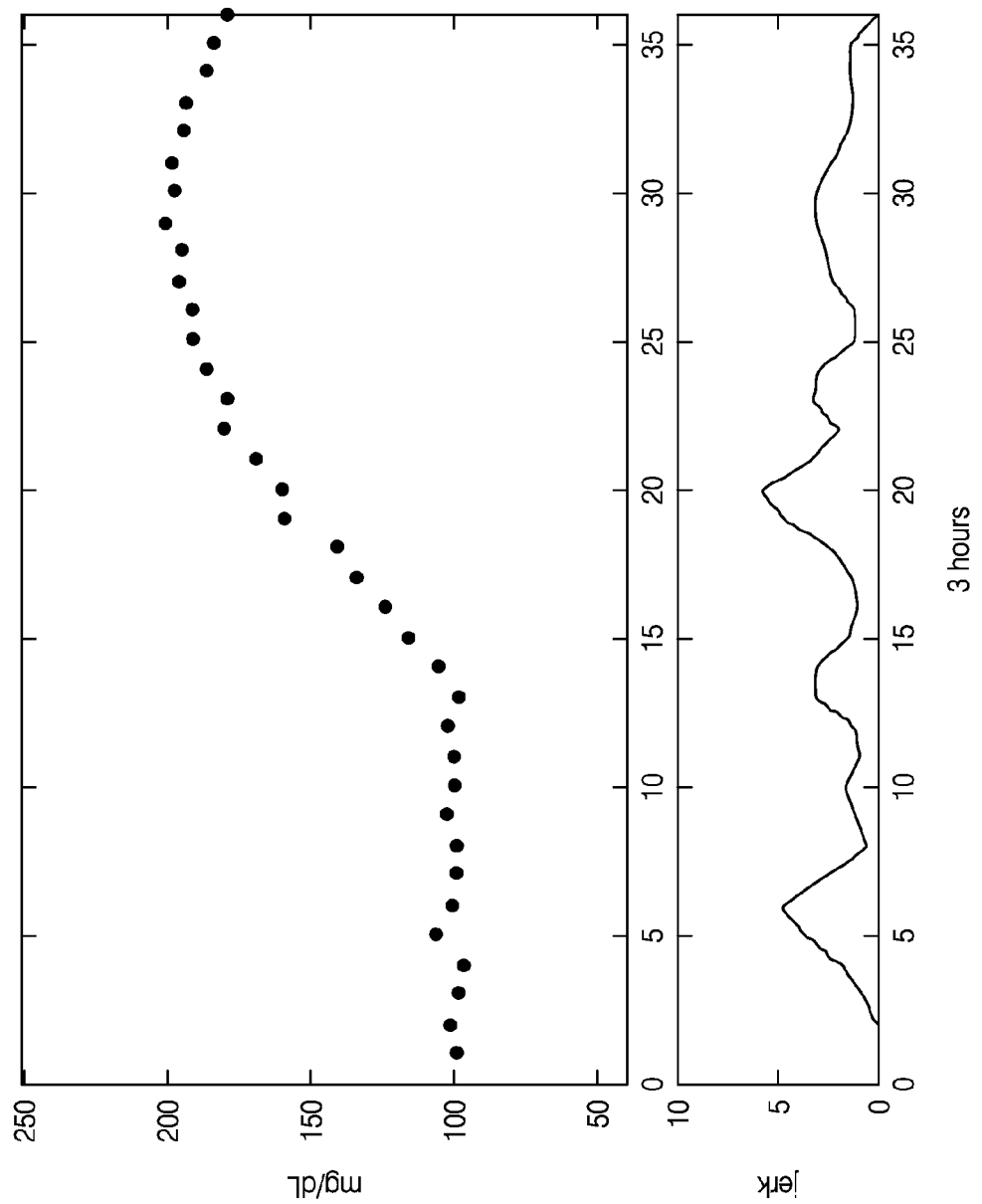

For example, in a particular implementation of noise filtering, illustrated in FIGS. 6B-6D, filtering is performed differently at different rates of change to achieve different levels of smoothness. In more detail, for a given received signal, a magnitude of noise within the signal is measured over a window of time, and then the rate of change for the signal is measured over a similar window of time. While it is possible to completely remove the noise error by filtering, an error is created in doing so, the error being equal to the rate of change multiplied by the filtered delay. As it is preferable to present smooth data to users, a longest delay possible may be chosen for maximum smoothness. In other words, the filter delay is chosen to be equal to the noise magnitude divided by the rate of change. In this way, minimum error is achieved with maximal smoothness. FIGS. 6B and 6C illustrate two examples, having different rates of change but the same noise magnitude. The resulting filter lengths are also illustrated. Thus, in one type of responsive processing, a filter delay is altered based on at least one signal characteristic, such as a magnitude of noise, as well as in some cases a rate of change of the signal.

In another implementation, and referring to FIG. 6D, thresholds may be set for a level of smoothing not based on accuracy of the signal but rather based on user perception of data quality. A characteristic of the signal may be measured. In one case, a third derivative characteristic (i.e., "jerk") has been shown to indicate signal quality as perceived by users, and is a useful characteristic since it is easily measurable in real time, particularly when sampling occurs frequently, e.g., every 30 seconds. A set of signals with varying jerk levels may be displayed to users, and users may select which signal they wish to see, e.g., which delivers the most informative data to that user. By monitoring selections, a determination may be made as to jerk levels that are acceptable or unacceptable to users. Even in such systems, some level of minimum filtering may be performed to meet user expectations of signal smoothness.

Besides filtering, other types of signal processing unrelated to transformation of the raw signal into a clinical value will also be understood.

The received signal 62, raw signal 64 or processed signal 66, is then analyzed to discriminate a fault therein, with or without the use of clinical context information and/or other signals, and a result 72 is obtained which includes data about a fault on which responsive processing may be based. Details of the analysis and discrimination are now described. In general, an exemplary implementation may be to receive the signal data and compare the same against fault discrimination criteria, in order to determine or discriminate fault information.

Figure 7:
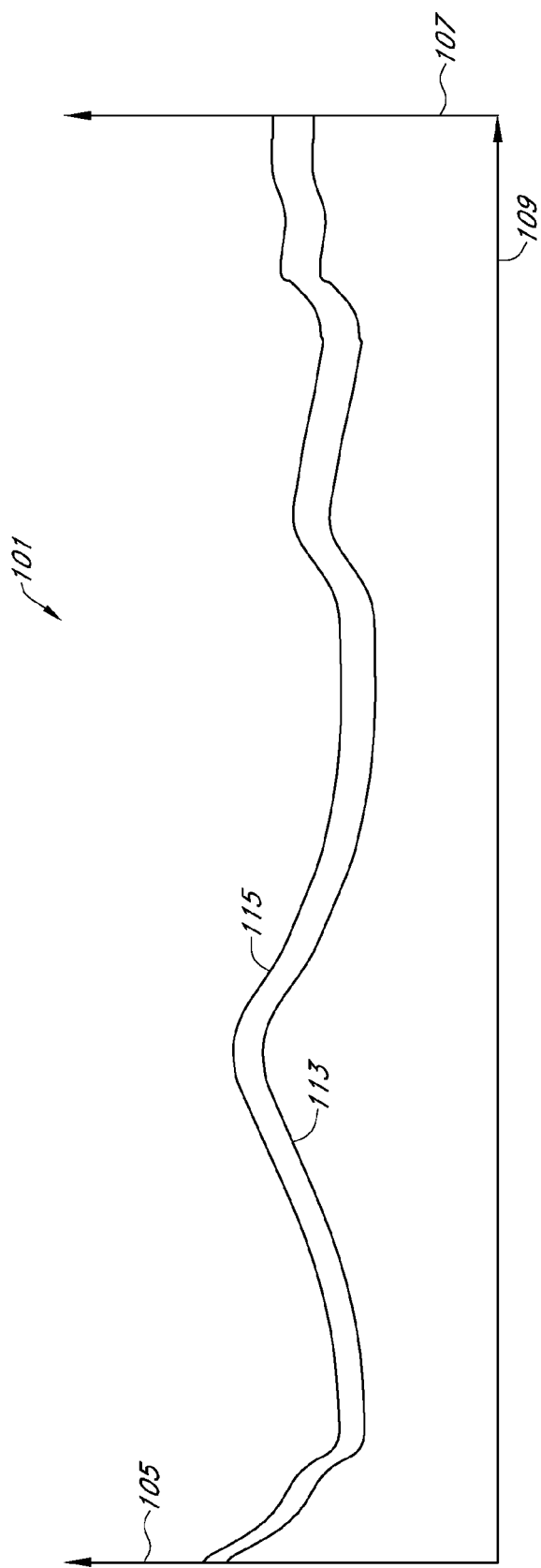
FIG. 7 is a plot indicating the effect of temperature on noise.

Other signals 74 may be employed in the discrimination analysis, besides that of the received raw analyte (e.g., glucose) electrode signal. Such other signals include those relating to temperature of the sensor and associated electronics, impedance of the sensor and constituent components, background noise encountered by the sensor, and the like. For example, and referring to FIG. 7, a graph 101 is illustrated having a raw signal axis 105 and a temperature axis 107, plotted against time 109. As temperature rises, one potential effect of the same is to cause a gradual increase or decrease in the signal, this increase or decrease unrelated to actual glucose levels. A raw data trace 113 is illustrated representing an actual glucose value, e.g., in mg/dL, without temperature effects. A trace 115 is also illustrated, this trace representing the raw data in the case of an elevated internal sensor temperature, the elevated temperature causing a gradual increase in the signal (thus causing a separation in the traces). By establishing a correlation between an elevated sensor temperature and an increased signal, the former can be used as an input in the discrimination analysis.

Figure 8A:
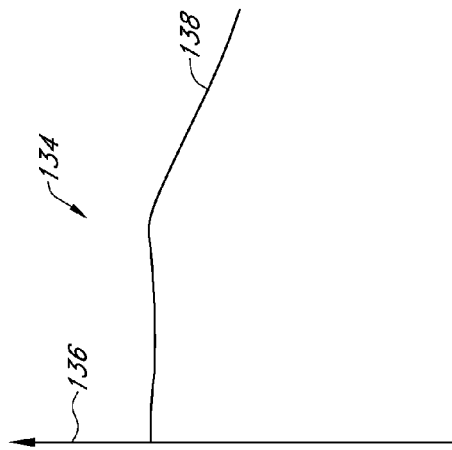
FIGS. 8A-8D are plots indicating various types of faults, e.g., compression (A), reference electrode depletion (B), the presence of noise (C), and a sensor fault discriminated by un-physiological behavior (D)

As another example, the signal from other constituent sensors such as oxygen sensors may be employed in fault discrimination. For example, if because of a compression fault (described in greater detail below), a glucose sensor signal is blocked, the compression fault should also block the oxygen sensor. An example is shown by the graph 122 of FIG. 8A, in which raw signal values are plotted on axis 124 versus time on axis 126. A raw signal value 132 is illustrated, along with an oxygen sensor value 128. The raw signal value 132 suffers a drop at or near the same time as the oxygen sensor value 128, indicating a compression fault. Thus, detecting a blocked signal on both sensors leads to a greater likelihood the fault is caused by compression.

Figure 8B:
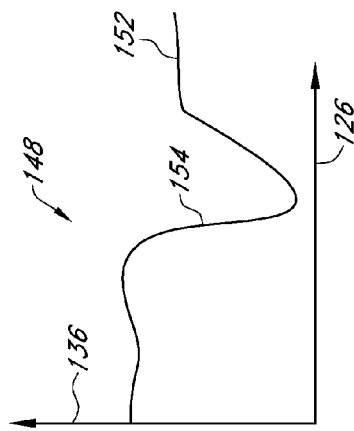

Referring back to FIG. 6, as another example of the use of other signals 74, the signal from a reference electrode may be employed in the fault discrimination method. For example, if the reference electrode signal drifts or shifts, such may be an indication that the reference analyte is depleted. In these cases, the value measured by the reference electrode becomes particularly oxygen sensitive. Thus, when the reference electrode value drifts and/or becomes highly oxygen sensitive, a fault of depletion of the reference analyte may be discriminated. An example is shown by the graph 134 of FIG. 8B, in which the ordinate represents the reference electrode signal, the abscissa is time, and the curve 138 illustrates a gradual drift downward of the reference signal electrode potential. In such cases, responsive processing may include the running of a potential sweep in order to detect the shift in the reference bias. Such potential sweeps may be part of a self diagnostics suite of routines, and are described in greater detail below.

As yet another example of the use of other signals 74, where an implantable pump for a medicament is employed, data may be obtained from the pump insertion set, including data about pressure. Such may be advantageously employed in fault discrimination. In this regard it is noted that where pumps are employed, scar tissue may grow and such impedes delivery of a medicament. Using fast sampling or other such quantification of the pressure required to move, or initiate the movement, of the stepper motor inside of a pump, a profile may be built up of the required pressure versus the amount of scar tissue, and the profile may be personalized to the user. In this way, a fault profile may be developed of scar tissue buildup, and the same used as a signal criterion for fault discrimination, as an additional signal, like that of temperature. In other words, a signal characteristic or template may be determined of scar buildup, and when the same is seen in an evaluated signal, the fault of scar tissue is discriminated. Once the fault is discriminated, the same may be used to adjust delivery and/or bolus delivery and applied to future deliveries. Moreover, the same may be used to anticipate blockage.

As yet another example of the use of other signals 74, a signal pertaining to an impedance measurement may be employed between the signal or working electrode (e.g., in a host) and an external electrode (e.g., on the skin), which may or may not be the same as a reference electrode. In this way, electrochemical impedance may be measured between the physiological environment and the signal electrode. Even more importantly, changes such as increases or decreases of such electrochemical impedance may be employed in fault discrimination. Additional details of such impedance measurements are described below.

Next, various categories 76 of techniques will be seen, as well as a set 78 of various techniques themselves. According to implementation, a particular technique or a group of techniques may be employed from the categories 76 or from the set 78. In most of these techniques, a step is generally included of detecting if the signal (or signal transform) deviates from what is expected or predicted, taking account of the normal variance in the signal, by more than a predetermined amount, and more particularly where such deviation is determined with a predetermined confidence level. Aspects of the normal variance in the signal, and confidence levels thereof, and their calculation are described in U.S. Patent Publication No. US-2009-0192366-A1 and U.S. Patent Publication No. US-2014-0278189-A1, both of which are assigned to the assignee of the present application and herein incorporated by reference in their entireties.

The categories 76 include time-based techniques 82, frequency-based techniques 84, and time-frequency ("wavelet") based techniques 86. Time-based techniques 82 are in many cases considered to be fastest. It will be understood that analyses may be performed using more than one technique category. Various types of techniques are now described.

Figure 8C:
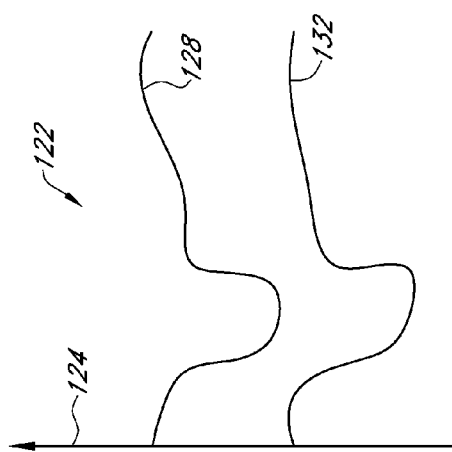

For example, a step of raw signal analysis 88 may be performed, and the same may be performed in the time domain or in the frequency domain. This step may be considered generally a precursor to or is generic to other steps performed. For example, such raw signal analysis 88 may include an analysis of the frequency of noise, as certain faults lead to certain respective prevalent noise frequency values, which can then be used in their discrimination. In the same way, noise may be divided into binary states, such as high amplitude/low amplitude, high frequency/low-frequency, and such binary states may be employed in fault discrimination. The smoothness of the data, or lack thereof, may be employed in fault discrimination using raw signal analysis. For example, lack of smoothness may indicate the presence of a fault, and vice versa. Referring to the graph 142 of FIG. 8C, a raw signal value 144 is illustrated with a noise section 146. All other factors being equal, it is more likely that a fault has occurred in the noise section 146 than in the remainder of the curve. This same determination would arise from frequency analysis.

Changes in the signal that are not related to physiology may be detected by raw signal analysis. For example, maxima and minima exist for physiological rates of change of glucose, and if rates of change are measured that are greater than the maxima, or less than the minima, such may indicate a fault. For example, referring to the graph 148 of FIG. 8D, a raw signal value 152 is illustrated with a sudden decrease 154. The sudden decrease 154 may be of greater magnitude than would possibly or ordinarily be encountered in a physiological system, e.g., a raw signal value in a user would not be expected to exhibit such a drop (or conversely, a rise above normal physiological thresholds). Physiological criteria may be determined based on a priori date from a particular patient or sets or patients, and may be further individualized to a person's normal glucose profile, for example. Accordingly, non-physiological apparent glucose changes may be discriminated as a fault.

Figure 8D:
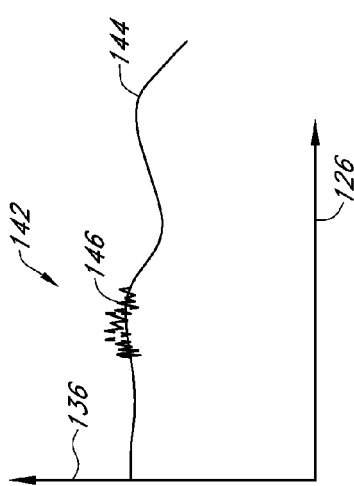

The direction of a signal artifact may also be taken into account as part of the raw signal analysis. For example, and as described in greater detail below, if an analyte concentration has a steep downward trend with noise, such may be associated with the faults of compression or "dip-and-recover". An example is shown in FIG. 8D at the portion of the curve indicated by section 154. Similarly, if the raw signal has a steep upward trend with noise, such may be associated with the fault of an electrical short-circuit, e.g., from water ingress into the transmitter contact area.

Referring back to FIG. 6, other signal processing related to raw signal analysis 88 will also be understood, including those involving complex frequency-based analysis, e.g., high pass filters, low pass filters, and match filters.

Similarly, a step of residual signal analysis 92 may be performed, in which raw signal data is analyzed vis-à-vis filtered signal data. In more detail, in yet another method for fault discrimination involving examination or evaluation of the signal information content, filtered (e.g., smoothed) data is compared to raw data (e.g., in sensor electronics or in receiver electronics). In one such embodiment, a signal "residual" is calculated as the difference between the filtered data and the raw data. For example, at one time point (or one time period that is represented by a single raw value and single filtered value), the filtered data can be measured at 50,000 counts and the raw data can be measured at 55,500 counts, which would result in a signal residual of 5,500 counts. In some embodiments, a threshold can be set (e.g., 5000 counts) that represents a first level of noise (e.g., signal artifact) in the data signal when the residual exceeds that level. Similarly, a second threshold can be set (e.g., 8,000 counts) that represents a second level of noise in the data signal. Additional thresholds and/or noise classifications can be defined as is appreciated by one skilled in the art. Consequently, signal filtering, processing, and/or displaying decisions can be executed based on these conditions (e.g., the predetermined levels of noise).

Although the above-described example illustrates one method of determining a level of noise, or signal artifact(s), based on a comparison of raw vs. filtered data for a time point (or single values representative of a time period), a variety of alternative methods are contemplated. In an alternative exemplary embodiment for determining noise, signal artifacts are evaluated for noise episodes lasting a certain period of time. For example, the processor (in the sensor or receiver) can be configured to look for a certain number of signal residuals above a predetermined threshold (representing noise time points or noisy time periods) for a predetermined period of time (e.g., a few minutes to a few hours or more).

In one exemplary embodiment, a processor is configured to determine a signal residual by subtracting the filtered signal from the raw signal for a predetermined time period. The filtered signal can be filtered by any known smoothing algorithm such as those described herein, e.g., a 3-point moving average-type filter. The raw signal can include an average value, e.g., where the value is integrated over a predetermined time period (such as over 5 minutes). Furthermore, it is noted that the predetermined time period can be a time point or representative data for a time period (e.g., 5 minutes). In some embodiments, where a noise episode for a predetermined time period is being evaluated, a differential can be obtained by comparing a signal residual with a previous signal residual (e.g., a residual at time (t)=0 as compared to a residual at (t)=5 minutes.) Similar to the thresholds described above with regard to the signal residual, one or more thresholds can be set for the differentials, whereby one or more differentials above one of the predetermined differential thresholds define a particular noise level. It has been shown in certain circumstances that a differential measurement, as compared to a residual measurement as described herein, amplifies noise and therefore may be more sensitive to noise episodes, without increasing false positives due to fast, but physiological, rates of change. Accordingly, a noise episode, or noise episode level, can be defined by one or more points (e.g., residuals or differentials) above a predetermined threshold, and in some embodiments, for a predetermined period of time. Similarly, a noise level determination can be reduced or altered when a different (e.g., reduced) number of points above the predetermined threshold are calculated in a predetermined period of time.

In some embodiments, one or more signal residuals are obtained by comparing received data with filtered data, whereby a signal artifact can be determined. In some embodiments, a signal artifact event is determined to have occurred if the residual is greater than a threshold. In some exemplary embodiments, another signal artifact event is determined to have occurred if the residual is greater than a second threshold. In some exemplary embodiments, a signal artifact event is determined to have occurred if the residual is greater than a threshold for a period of time or amount of data. In some exemplary embodiments, a signal artifact event is determined to have occurred if a predetermined number of signal residuals above a predetermined threshold occur within a predetermined time period (or amount of data). In some exemplary embodiments, an average of a plurality of residuals is evaluated over a period of time or amount of data to determine whether a signal artifact has occurred. The use of residuals for noise detection can be preferred in circumstances where data gaps (non-continuous) data exists.

In some exemplary embodiments, a differential, also referred to as a derivative of the residual, is determined by comparing a first residual (e.g., at a first time point) and a second residual (e.g., at a second time point), where a signal artifact event is determined to have occurred when the differential is above a predetermined threshold. In some exemplary embodiments, a signal artifact event is determined to have occurred if the differential is greater than a threshold for a period of time (or amount of data). In some exemplary embodiments, an average of a plurality of differentials is calculated over a period of time or amount of data to determine whether a signal artifact has occurred. Other details of residual analysis are described in U.S. Pat. No. 8,260,393, incorporated by reference above.

Returning again to FIG. 6, pattern analysis 94 may also be performed which may lead to certain expected or predicted changes in signal values, measured in an absence of faults, and thus if a signal change is measured that fits the pattern, a fault need not be discriminated. Without pattern analysis, a similar change in signal value may well lead to a fault being erroneously discriminated. Conversely, if a signal is received that does not fit the pattern, a fault may be detected and, depending on the signal characteristics and/or clinical context, a fault may be discriminated. Thus, pattern analysis can assist in the discrimination of faults.

In more detail, certain signal characteristics or patterns may indicate or be signatures for various faults, and when such signal characteristics or patterns are seen in subsequent signals, such may provide evidence that the respective fault is recurring. An example is provided below of the use of signal templates. A template is determined for a given fault, and a signal is projected onto the template to determine how much of the signal can be attributed to the template waveform, and thus to the fault associated with the template waveform. Such is described in greater detail below.

Additional details of such pattern analysis techniques are provided in U.S. Patent Publication No. US-2013-0035575-A1 and U.S. Patent Publication No. US-2014-0129151-A1, both of which are assigned to the assignee of the present application and herein incorporated by reference in their entireties.

Another step which may be performed for signal discrimination is that of "slow versus fast" sampling (step 96). In these techniques, data is sampled at two or more different sampling rates, simultaneously or sequentially. Such techniques may be performed constantly or only at certain times, e.g., during a "self-diagnostic" mode. For example, data may be sampled both at 30 second intervals and at five-minute intervals. Data sampled at 30 second intervals is more granular and can show features related to noise components and faults which are not apparent from the data sampled at five-minute intervals, especially high-frequency noise components.

Figure 9A:
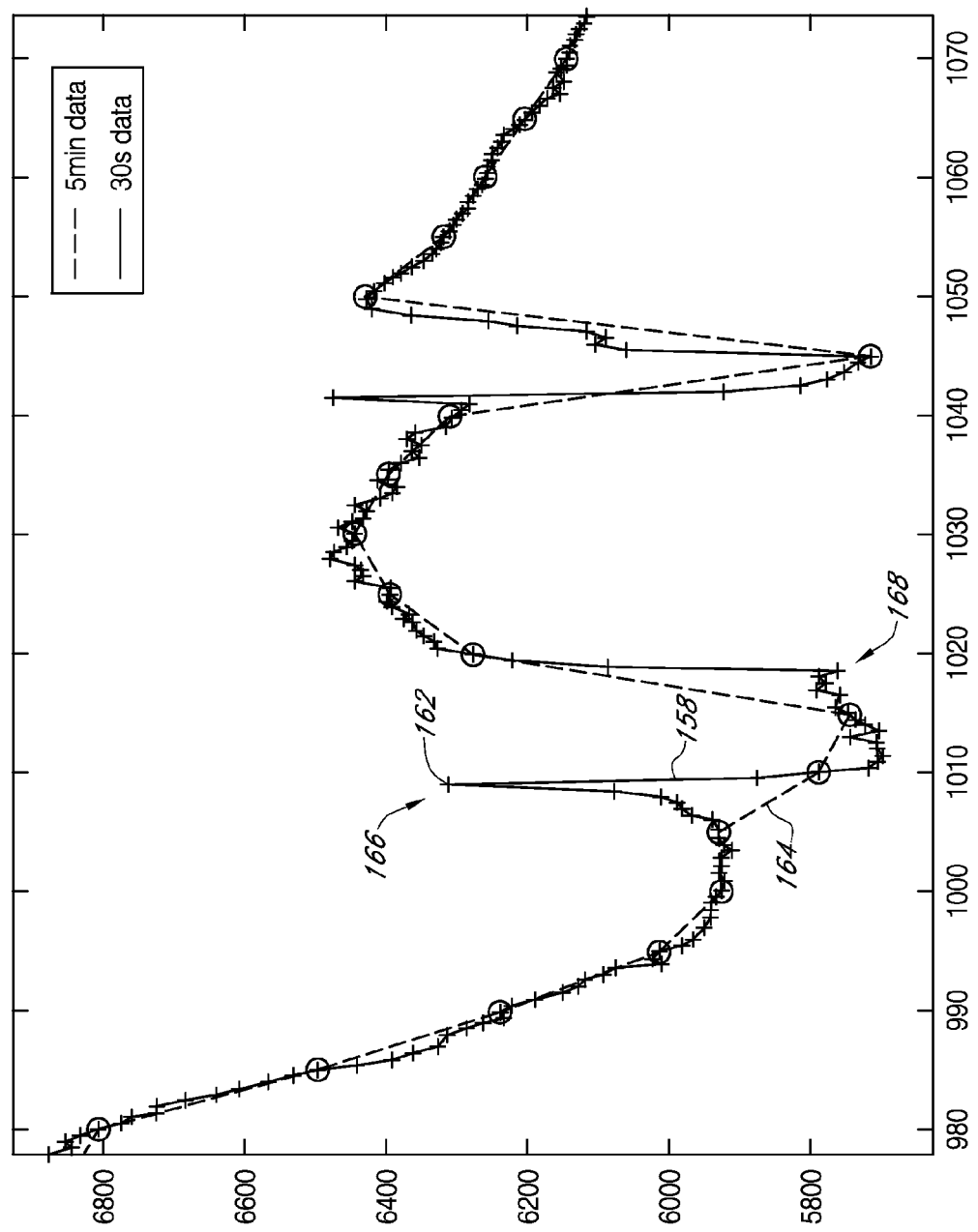
FIGS. 9A and 9B illustrate slow versus fast sampling.
Figure 9B:
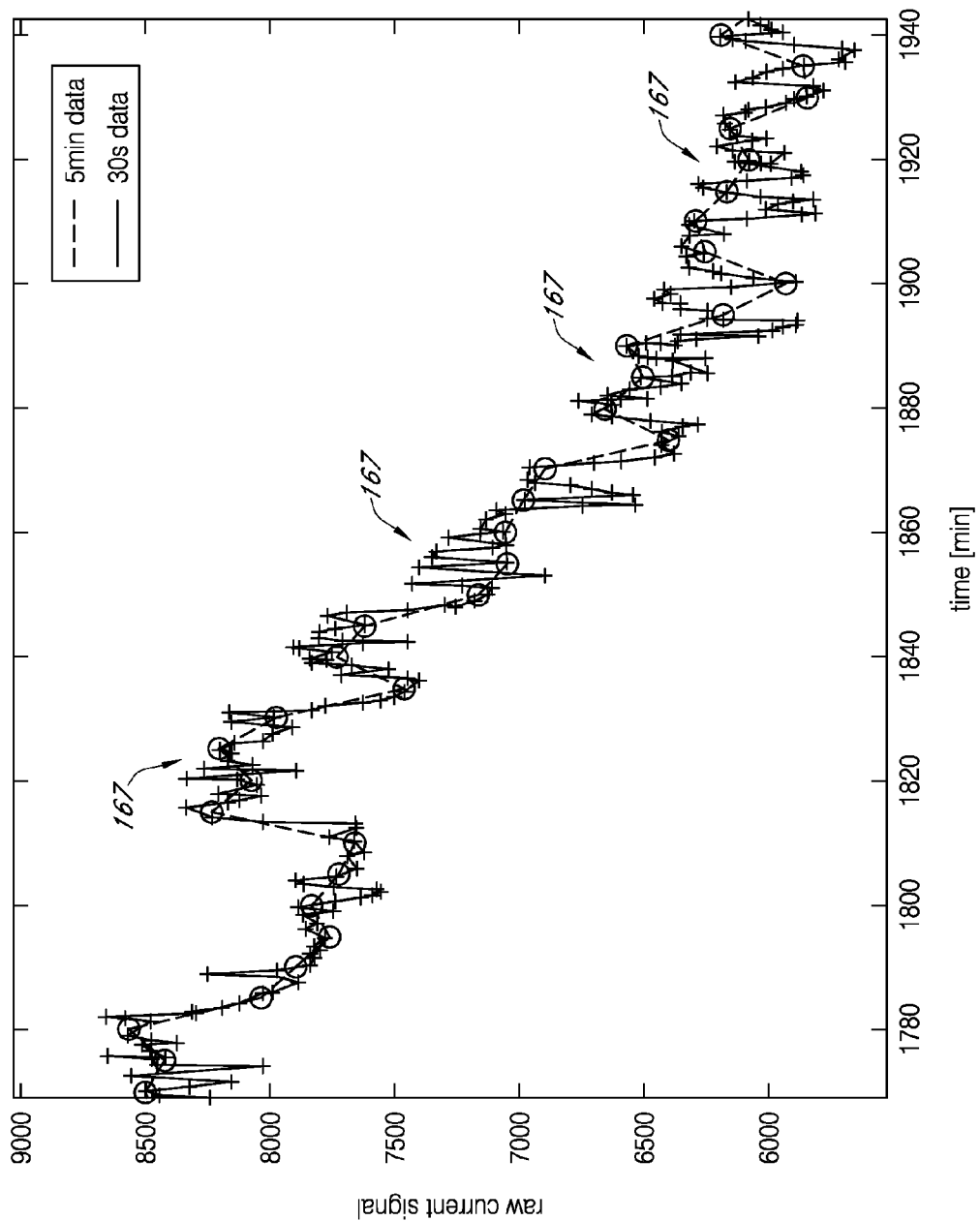

For example, referring to FIG. 9A, data sampled at 30 second intervals is illustrated by the solid line 162, and data sampled at five-minute intervals is illustrated by the dotted line 164. Along the line 162, that time point 166 a sudden drop is seen, with a corresponding sudden rise at time point 168. This drop and rise is characteristic of the fault of "compression", e.g., where a user's weight, or a portion thereof, has impinged on their sensor and associated electronics (the drop), and then subsequently removed the impingement (the rise). FIG. 9B illustrates another example of the use of slow versus fast sampling, where not only can fast sampling provide better curve definition for fault discrimination, but additional features can also be gleaned from the data. For example, the data sampled every 5 minutes is sufficient to know the glucose concentration, and to indicate certain spikes likely due to noise. However, examination of the same data sampled every 30 seconds clearly indicates the presence of high-frequency noise portions 167. Thus, using both slow and fast sampling provides for better noise discrimination as well as a reduction in the time lag before noise is noticed and responsive processing occurs. The analysis of such high-frequency noise components using fast sampling further allows for an accurate end-of-life detection method, extending wear duration and making more efficient replacement claim procedures. Another example of end-of-life detection is given below.

As another example of signal processing, a step of employing fuzzy logic 103 may be used. Such can conceptually be applied to any noise detection scheme, where the noise detection measures the level of noise, rather than a binary or broadly categorized noise level scheme. In particular, using fuzzy filtering, filtering may be applied more incrementally or smoothly, by adaptively weighting the raw versus filtered signal to achieve an incrementally more or less aggressively filtered signal. Fuzzy filtering may also be applied to the slow versus fast sampling signals techniques, or indeed with any techniques employing two different resolutions of signal. The fuzziness of the filter may be applied based on the level of noise and/or clinical context.

In more detail, and as noted above, residual analysis can be employed in noise management algorithms, including residuals (differences) between raw and unfiltered values or delta residuals, i.e., the change from one residual to another. These algorithms are useful in estimating noise levels. In one implementation, the residual may be passed through three different filters, e.g., one slow-moving, one medium moving, and one fast-moving, and based on the ratio of the outputs of the three different filters to a very slow moving average, the algorithm can determine whether the noise state is clean, light, medium, or severe.

One problem with such techniques is that they are binary. In one case the signal is "clean" and the delay or time lag in the signal is just related to the sampling periodicity, e.g., e.g., 5 minutes. In another case, filtering is applied, and the time lag is related to the sampling window of the filter, e.g., 10 minutes For noisy signals, this long time lag can be problematic, particularly if the user's glucose level is dropping fast, e.g., −5 mg/dL/min. Use of fuzzy logic and in particular a fuzzy filter can reduce this delay as follows.

In particular, an estimated glucose value can be determined by the equation:

EGV=(Count−Baseline)/Slope where count=2*α*Filter(N)+(1−α)*Raw(N)
where Filter(N) represents the filtered signal and Raw(N) represents the raw signal. α is a weighting factor that is close to zero when the residual or delta residual is small, and close to one when the residual/delta residual is large. α may be described by any of a variety of continuous functions, but in many cases is linear and monotonically increasing.

The calculation of α may vary based on the underlying model used. At every point, the absolute residual/delta residual may be calculated, so a new weight may be calculated at every point. Besides absolute residuals, other metrics may be utilized, e.g., lightly filtered residuals, medium filtered residuals, severe filtered residuals, ratio of lightly-filtered residual to slow-moving filtered residual, ratio of medium-filtered residual to slow-moving filtered residual, ratio of severe-filtered residual to slow-moving filtered residual, and so on. Signed residuals (negative/positive) may be utilized to manipulate the time lag, e.g., sensor lags on glucose rises, and sensor leads on glucose drops. For example, if the underlying trend is a drop, and the sensor is leading, then additional filtering can be afforded. On the other hand, if the trend is a rise, then the raw signal may be averaged, provided the current residual is small, and a projected value could be calculated for 5 minutes from the current time, and additional weight given to the projected value over the raw value. In this way, the fuzzy filter may be applied incrementally. In this way, if there is very little noise, filtering may occur but only lightly and not aggressively. If significant noise is present, filtering may be applied more aggressively.

In an even more sophisticated implementation, the concept of a fuzzy unit (FU) may be defined as shown below:

$$\text{Fuzzy Unit } (FU) = 100 * \frac{\text{Medium Filtered Residual (or } DeltaRresidual \text{ if one be calculated)}}{\text{Slow-Moving Average}}$$

When the first fuzzy unit is calculated, the filter may be initialized as follows:
CurrentNoisePercent=FU;
PreviousNoisePercent=previous prediction of the FU;
RawError[n]=the error between the CurrentNoisePercent and the PreviousNoisePercent;
SmoothedError[n]=the filtered error between the CurrentNoisePercent and the PreviousNoisePercent, e.g., 0;
α=a smoothing factor between PreviousNoisePercent and the CurrentNoisePercent, e.g., 0.65;
β=a smoothing factor between the smoothed error and the raw error, e.g., 0.65; and $$NoiseWeight = \frac{1}{2}\left[1 + \text{erf}\left(\frac{CurrentNoisePercent - \mu}{\sqrt{2\sigma^2}}\right)\right].$$

NoiseWeight is employed to create a new filtered count as shown below:

$$FilterCount'[n] = NoiseWeight * FilterCount[n] + \frac{(1 - NoiseWeight) * RawCount[n]}{2}$$

Figure 10A:
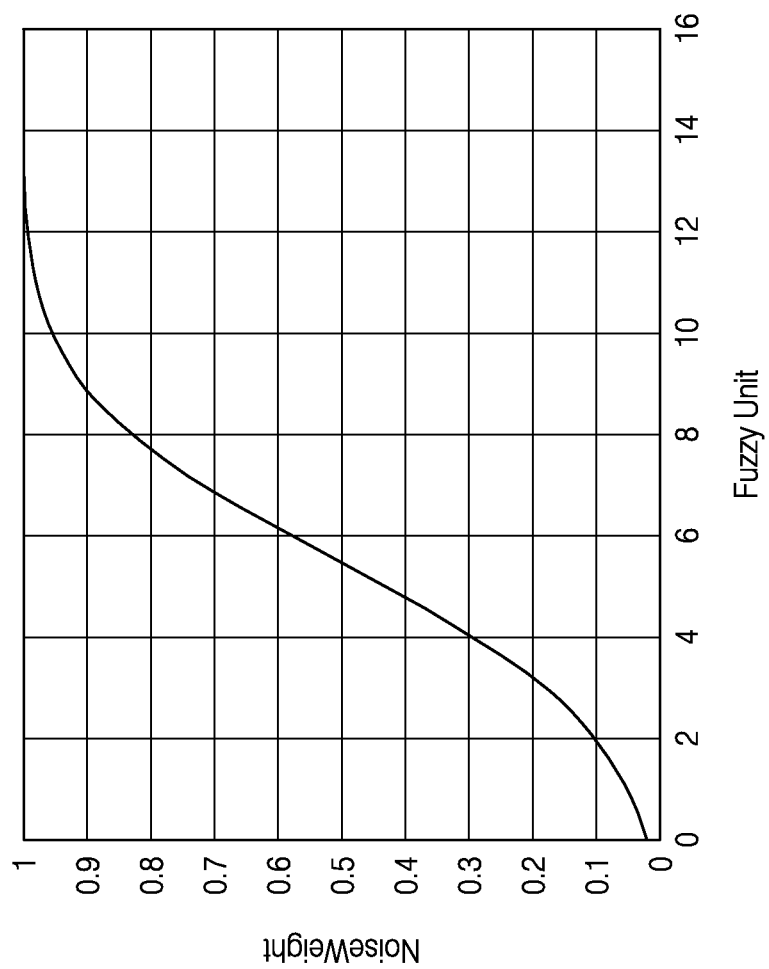
FIGS. 10A-10D illustrate a flowchart and plots for applying fuzzy logic in noise determination.

The relationship between the fuzzy unit FU and NoiseWeight takes the shape illustrated in FIG. 10A. As may be seen in the figure, as noise increases, the filter is applied to an increasing extent.

Figure 10B:
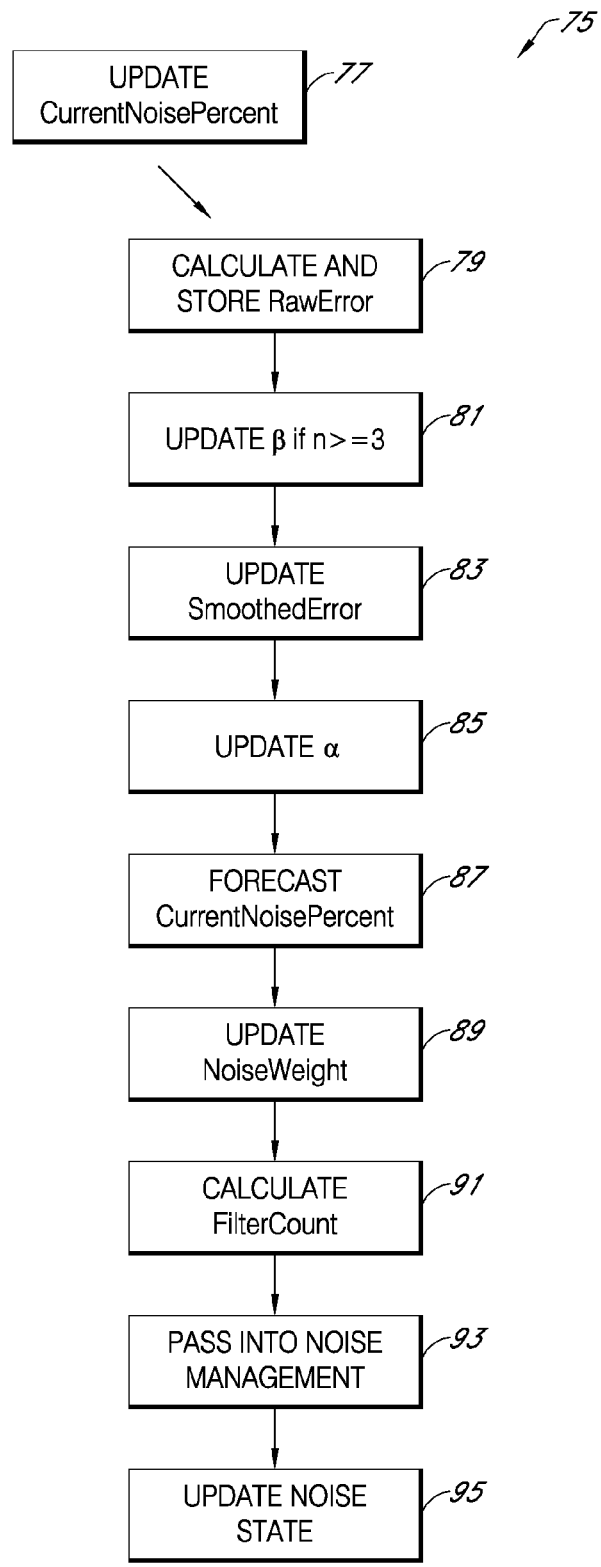

Referring to the flowchart 75 of FIG. 10B, after the first fuzzy unit is calculated, the following steps may be executed for each subsequent calculation of the fuzzy unit (CurrentNoisePercent) (step 77).

A first step to calculate RawError and to store the same (step 79):

$$RawError[n] = \left|\frac{PreviousNoisePercent - CurrentNoisePercent}{CurrentNoisePercent}\right|.$$

If n>=3, β is updated (step 81) as shown below:
TwoPointError=|RawError[n−2]−RawError[n−1]|,
OnePointError=|RawError[n−1]−RawError[n]|, $$DeltaError = \left|\frac{TwoPointError - OnePointError}{OnePointError}\right|,$$

and subsequently:

$$\beta = \frac{1}{2}\left[1 + \text{erf}\left(\frac{DeltaError - \mu}{\sqrt{2\sigma^2}}\right)\right].$$

Figure 10C:
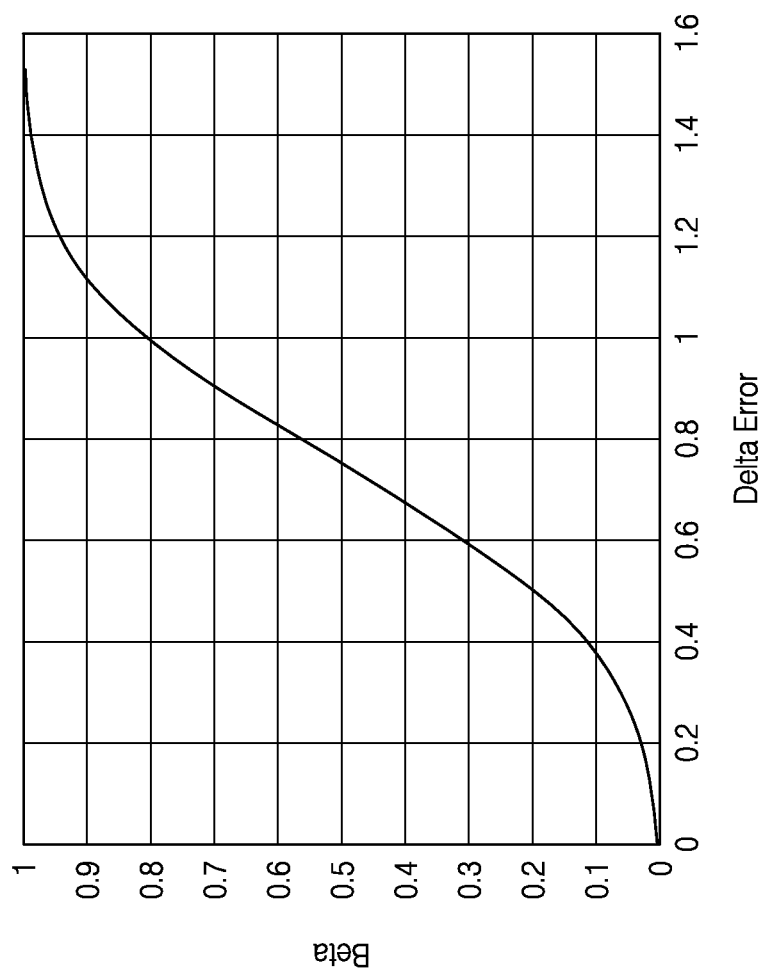

And where, for example, μ0.75 and σ=0.29, β takes the shape indicated in FIG. 10C, which indicates that as the change in the error increases, β increases and thus more emphasis will be placed on the current SmoothedError.

A next step is to update the SmoothedError (step 83):

SmoothedError[$n$]=(1−β)*RawError[$n$]+
β*SmoothedError[$n$−1].

A next step is to update α (step 85):

$$\alpha = \frac{1}{2}\left[1 + \text{erf}\left(\frac{SmoothedError - \mu}{\sqrt{2\sigma^2}}\right)\right].$$

Figure 10D:
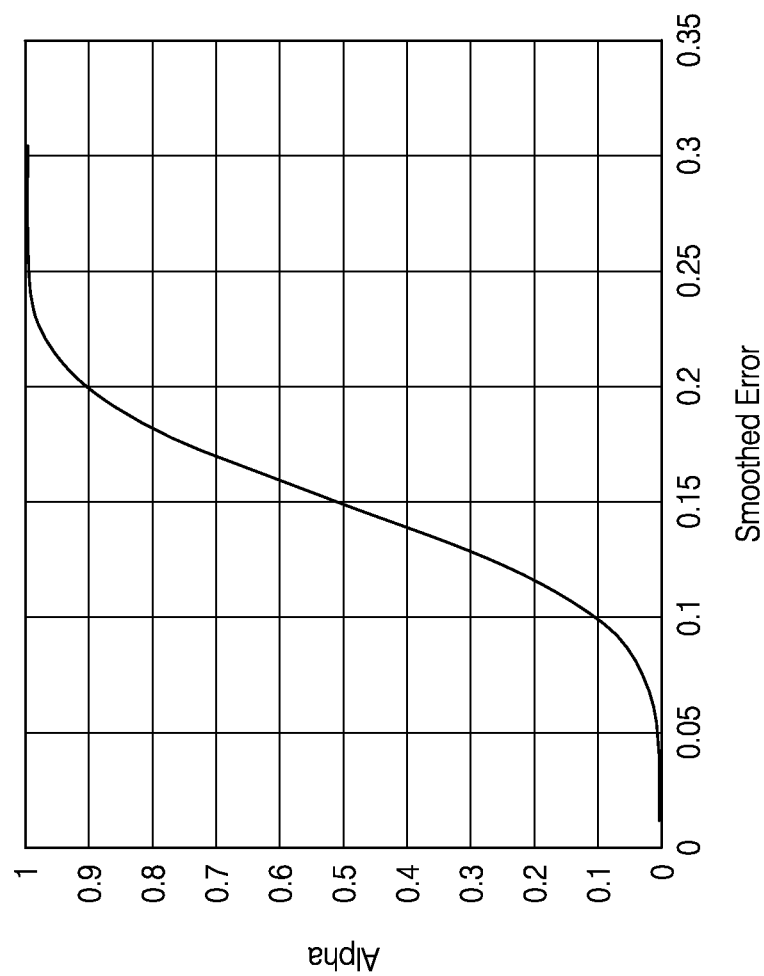

And α takes the shape illustrated in FIG. 10D.

A next step is to make a forecast of the CurrentNoisePercent (step 87):

PreviousNoisePercent=α*CurrentNoisePercent+(1−α)
*PreviousNoicePercent.

This step is followed by updating the NoiseWeight (step 89):

$$NoiseWeight = \frac{1}{2}\left[1 + \text{erf}\left(\frac{PreviousNoisePercent - \mu}{\sqrt{2\sigma^2}}\right)\right]$$

The new FilterCount is then calculated (step 91):

$$FilterCount'[n] =$$
$$NoiseWeight * FilterCount[n] + \frac{(1 - NoiseWeight) * RawCount[n]}{2}$$

The FilterCount' and RawCount are then passed into an appropriate noise management algorithm (step 93 (FIG. 10B)), and then the point and noise states are updated, e.g., using probabilistic thresholds. Exemplary probabilistic thresholds are shown in the table below:

| | |
|---|---|
| If NoiseWeight > 0.95 | PointNoise = severe |
| | NoiseState = severe |
| ElseIf NoiseWeight > 0.82 | PointNoise = medium |
| | NoiseState = medium |
| ElseIf NoiseWeight > 0.4 | PointNoise = light |
| | NoiseState = light |
| Else | PointNoise = clean |
| | NoiseState = clean |

It will be understood that other thresholds may also be employed.

In tests, fuzzy filters have provided significantly faster responses to noise spikes as well as more rapid recovery from noise episodes than illustrated by prior efforts simply involving filtering. Fuzzy filters have also exhibited higher accuracy than such prior efforts.

In yet another variation in signal analysis methods, metrics may have weights associated, and the weights may be standard or may vary depending on metric. In this variation, accommodation is made for the observation that some metrics are larger indicators of a particular fault than others. For example, skewness and variance are larger indicators for oxygen noise (indicated by high-frequency noise and a downward trend) than they are for a shower spike (indicated by a smooth upward rise).

Other types of signal processing will also be understood from this disclosure to be employable according to implementation, and other factors, parameters, and variables may be used in the fault discrimination. For example, timestamps of data may be used in certain analyses, e.g., to detect certain time-based patterns or to determine time since implantation, which bears strongly on the determination of end-of-life. In this respect it is noted that in some cases the raw signal data correlates to established patterns of the patient. For example, raw sensor data indicating a potentially faulty situation because of an abnormally high signal value may at first appear to indicate a fault, but may also be caused by the user eating a regular meal. The determination that the user has eaten a regular meal may be by way of timestamp data, as well as machine learning (or other technique) in which a pattern may be established. Similarly, a spike in the data at a consistent time of day may be indicative of a water related error, such as related to a daily shower. Similarly, other types of faults may be more likely to occur at night, such as compression artifacts.

Other types of signal processing may include analysis of a time duration since the implant of the analyte monitor, e.g., which may be particularly important to examine to account for faults or errors that may occur over time or to older implants.

Finally, it is noted that where a specific factor, parameter, or variable has been noted above, a corresponding duration over which the same has occupied a range of values may be employed in fault discrimination, where the range of values is a narrow range or a wide range. Combinations of the above factors, parameters, and variables, may also be employed.

Clinical Context Information

Types of data corresponding to clinical context information are now described. These types of data relate to the observation and treatment of actual patients rather than simply looking at internal signals unknown to the patient. However, it should be understood that clinical context information may be derived from internal signals, using processing that transforms the internal signals into data related to the observation and treatment of actual patients. For example, while the raw sensor signal is unknown to the patient, the actual glucose concentration, calibrated and transformed from the raw signal, constitutes clinical context information 186. Similarly, while temperature and time information may be considered internal information, the comparison of temperature and time information to certain clinical context criteria (e.g., sleep/awake, showering, sedentary/active information) may be used to derive clinical context information, In general such clinical context information includes anything that affects the person with the condition, e.g., diabetes, including social, emotional, physical, and environmental influences, and indeed anything which may relate to or impacts the physiological health or environment surrounding the patient. By identifying the clinical context, additional intelligence is gained for fault discrimination and responsive processing purposes.

Figure 11:
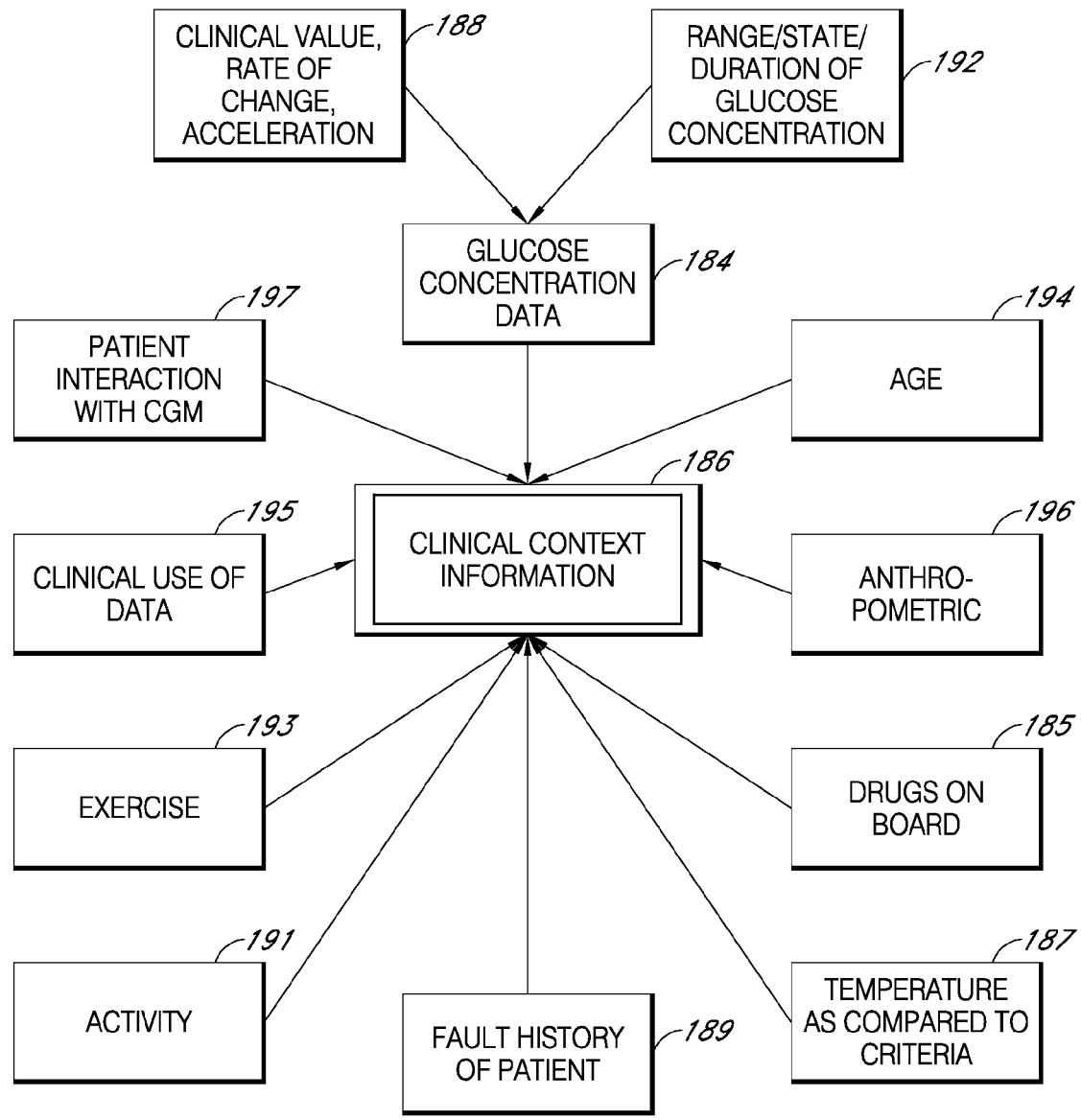
FIG. 11 illustrates various types of clinical context information.

FIG. 11 illustrates various types of data or other information that may constitute or be involved in the determination of clinical context information 186. A key contributor to clinical context information 186 is the glucose concentration data 184. This data may include aspects 188 such as the actual clinical value, its rate of change, acceleration, higher order derivatives, and the like. The glucose concentration data 184 may also include aspects 192 such as ranges of glucose concentrations, e.g., ranges maintained by the patient's glucose concentration, as well as durations over which users have clinical glucose values within specific ranges. Similarly, states may be defined and used as ranges, e.g., hypoglycemic, hyperglycemic, or euglycemic. Such a state data may also include impending, predicted, or expected states. Other potential contributors to glucose concentration data 184 may include whether the patient is in a steady-state or is experiencing change in their glucose concentration.

Analyte concentration such as glucose concentration, when used as clinical context information, constitutes information that has been translated from a raw signal into a meaningful value for diabetes management, e.g., mg/dL or mmol/L, or time derivatives including mg/dL/min or mg/dL/min$^2$. Such is different from "sensor data" because it has been calibrated for clinical relevance. Quantities derived in part from glucose concentration information may also be employed, including glycemic urgency index ("GUI"), dynamic risk ("DR"), static risk ("SR"), and the like.

In many implementations, clinical context information will include, or be determined from, at least some aspects of analyte concentration, e.g., glucose concentration, or from the quantities derived in part from analyte concentration as noted above, e.g., glucose rate of change, glycemic state, GUI, and the like. In other words, where clinical context information is employed in fault discrimination and responsive processing, the clinical glucose value or a state pertaining thereto will be used. For example, given a particular fault, responsive processing may often depends on whether the user is hypoglycemic, hyperglycemic, or euglycemic. Such states may bear on whether a glucose display is suspended and/or whether a warning is given to the user. In the same way, the rate of change may often be employed, because if a fault causes a user's glucose value to become unknown or uncertain, the responsive processing will strongly bear on whether the glucose level was rising or falling prior to the fault, as well as the speed of rise or fall. Higher order derivatives may be employed to determine if a user's glucose level is likely to return to normalcy or if further excursions are expected. Thus, the clinical glucose value and related parameters are often used in fault discrimination and responsive processing.

Regarding non-glucose concentration related information, the same may include information and data relating to age 194, as such data often has a strong bearing on the clinical context; in other words, whether or not a fault is discriminated, or the type of fault, may depend on the age of the patient. Put another way, sensor data may be regarded as faulty for one patient but not for another, and age can be an indicator of "which bucket the data falls into". For example, for very young patients as well as elderly ones, each data point may be given significant weight as the consequences of faulty data may be more dire than that for stronger young adult patients. Accordingly, the system may be configured to be especially sensitive and to thus discriminate more faults in such situations and for such patients. It will be understood that generally age is one of many clinical context data variables that may be taken into account in the determination of the clinical context information 186, and thus the actual resulting fault discrimination and responsive processing behavior will depend on many factors.

Similarly, anthropometric data 196, which generally relates to body information such as BMI, can also bear on the determination of whether a fault has occurred. One way of measuring anthropometric information for such uses is by measuring the impedance from the tip of the sensor to the base patch, as discussed in greater detail above and below. While the above discussion was related to measuring the impedance in order to determine an internal aspect of the sensor or sensor electronics, here it is noted that impedance measurements may be employed to determine an external aspect, and in particular clinical context information. Impedance measurements can result in determinations of clinical context information including tissue type, BMI, and the like.

A further aspect includes data 185 about whether drugs have been administered such as insulin. In this case, raw sensor data indicating a potentially faulty situation because of an abnormally low signal value may indicate a fault, but may also be caused by a recent injection or bolus of a medicament such as insulin. By consideration of such clinical context, that which may otherwise be ascribed to a fault may be determined to be actual physiological data, i.e., not a fault. Conversely, if a recent injection or bolus has been made, but the signal is abnormally high, such may increase the likelihood of a fault being discriminated. Data about potentially interfering drugs may also be considered in the fault discrimination.

Yet another type of clinical context information includes data 187 about the external temperature as compared to clinical context criteria to determine clinical context information. Generally the temperature data and its comparison with criteria is combined with other clinical context information in the evaluation of a particular patient situation. Such clinical context information may indicate that the patient has entered a hot tub, shower, has been working out, has a fever, or the like.

Yet another aspect includes data 191 about the activity level of the patient, as well as data 193 about exercise relating to the user. Data 191 or 193 may be inferred from another wearable sensor, as well as a "fitband", gyroscope, accelerator in on-skin electronics, an accelerometer or GPS in a smart phone or smart watch, or via patient input, as well as other means. The data 191 may be quantitative or qualitative, and in the latter case may be measured as, e.g., "sedentary" or "active". Other gradations will also be understood. The data 193 may also be quantitative or qualitative, and in the former case, may provide an indication of the amount of movement the sensor has undergone, the period of time over which the movement has occurred, and derived quantities such as calories burned.

Yet another contributor to clinical context information 186 may be data 189 about the fault history of the patient. In particular, certain patients may have a particularly active fault discrimination history. Such patients include those with high wound responses, or who more often see early wound effects, or the like, which increase the overall likelihood of such a fault being seen for that patient in future sessions. Other patients may be more prone to compression faults, and this tendency may be factored into the analysis.

A further contributor to clinical context information 186 is data 195 about the clinical use of the data. This contributor pertains to how the data is used, e.g., whether in a closed loop system, open loop system, artificial pancreas system, with an integrated pump, or the like. In more detail, if the data is used in a closed loop system, the same may provide a driving factor for a pump which administers a medicament, e.g., insulin. In a closed loop system, the determination of whether a given signal is faulty may, for example, be more conservative because medicament delivery depends on the signal. In other words, the system may be configured to discriminate more or have a higher sensitivity for faults in this clinical context. Conversely, in an alternative implementation, where a pump driving algorithm has its own fault discrimination routines, the system may be configured to discriminate less or have a lower sensitivity for faults.

The above is premised on a potentially faulty signal driving a pump. Pump information may also be employed in a converse fashion to supplement, inform, and drive fault detection. For example, if a large bolus of insulin was recently injected, then a negative rate of change in glucose would be expected, but not a positive spike in the signal. Accordingly, if a positive spike in the signal occurs, such is more likely to be a fault that an actual glucose excursion. Variations of the use of "clinical use" data will also be seen given this teaching.

Another contributor to the clinical context information 186 is data 197 about patient interaction with their analyte monitor, e.g., CGM. The level to which a patient or user is interactive with their analyte monitor may be a factor in the determination of the clinical context information. For example, if a user does not consult their CGM very much, i.e., is noninteractive, then it may be presumed that each interaction, i.e., each data point received by the user, bears significant weight in user management of their disease, just based on the relative rarity of data points the user encounters. Conversely, for highly interactive users, each data point is important, but a fault may be less dangerous because the user is likely to receive another data point relatively soon. Patient interactions with their CGM can be tracked by button presses on the receiver, menu selections or screens viewed, calibrations, or the like.

Other clinical context information will also be understood. For example, correlation with normal glucose behavior may constitute clinical context information. In this example, patterns of glucose values may be established for a patient. Such patterns may be time-based or event-based, but generally indicate normal glucose behavior for a patient. Time-based patterns may be based on time of day, a weekly basis, a monthly basis, and so on. A current glucose levels can then be compared to normal or expected glucose patterns and profiles for the same time of day, week, or month, respectively deviations from the norm may then indicate a clinical event. Wavelet correlations may be employed in this analysis.

A local pressure surrounding the sensor may be employed in the determination of clinical context information, as the same can detect certain movements (or lack thereof) of the patient that may affect sensor function. Appropriate pressure sensors may be incorporated on or adjacent the sensor and/or sensor electronics described above by including a strain gauge or a piezoelectric material on the shell or outer body of the transmitter body, or pressure plates, gauges, or materials in the base (e.g., flexible portion) of the body. Such thin-film sensors may be employed for pressure detection and quantification. Generally, however, the use of such data is as an input to the overall determination of clinical context, and not merely to determine sensor function itself. In one implementation, the pressure may be employed as an input in the determination as to whether the patient was moving, sedentary, awake, asleep, and so on. For example, a sudden increase in pressure as detected by such a sensor may be combined with pattern data and/or time of day data (e.g., a patient usually goes to sleep at the same time the pressure increase occurred), and the patient movement data (e.g., the patient shows little to no movement). These signals evaluated together may lead to a clinical context of moving, sedentary, awake, asleep, or the like being determined. Additional details of certain of these aspects are provided in US PGP 2012/0078071, owned by the assignee of the present application and herein incorporated by reference in its entirety. Moreover, exemplary thin-film sensors are described below which may be integrated into the sensor electronics or the transmitter housing.

Certain types of clinical context information discussed above may be provided by the patient and entered in the monitor, particularly if the monitor is embodied by a smart phone or other device with a substantial user interface. For example, a user may be queried as to meals ingested, exercise performed, and the like. In some cases, a user query may be prompted by a fault, so as to disambiguate the same. For example, a user could be queried as to whether they were laying on top of their sensor, e.g., to discriminate a compression fault. Other questions will also be understood.

A patient query may be prompted to determine if a fault was preceded by a meal, so as to attempt to resolve an ambiguous rise in signal value. For example, if the query determines that the patient recently ingested a meal, a rise in signal value will likely be attributable to a post-prandial rise rather than an error or fault. Such information may also be provided by a processor module, e.g., in data communication with a food ingestion application, a camera for imaging a meal, and the like.

Similarly, a patient query may be prompted to determine if a fault was preceded by an insulin intake. Insulin information may also be provided by an integrated pump. For example, a sudden decrease in raw signal may be determined in this way to be the effect of a bolus of insulin rather than a fault.

Yet another type of clinical context information includes behavioral or contextual information. Such information may correspond to how a patient uses their mobile device, and thus gives context to certain data determined by the device. Behavioral or contextual information may be obtained via the system and can include an amount of interaction, glucose alerts/alarms states, sensor data, number of screen hits, alarm analysis, events (e.g., characteristics associated with the user's response, time to response, glycemic control associated with the response, user feedback associated with the alarm, not acknowledging alerts/alarms within X minutes, time to acknowledgment of alerts/alarms, time of alert state, and so on), diabetes management data (e.g., CGM data, insulin pump data insulin sensitivity, patterns, activity data, caloric data), data about fatty acids, heart rate during exercise, IgG-anti gliadin, stress levels (sweat/perspiration) from a skin patch sensor, free amino acids, troponin, ketones, adipanectin, perspiration, body temperature, and the like. The inputs may be provided by a sensor in data communication with the monitoring device. In some implementations, the information may be obtained through an intermediary such as a remote data storage. In some situations, a patient may use more than one device to track their diabetes (e.g., glucose displayed on medical device receiver and smart phone).

Contextual information which may be provided as clinical context information includes a person's biology, location, sensing surroundings (e.g., light, sound level), environmental data (e.g., weather, temperature, humidity, barometric pressure). The inputs may be received via a peer-to-peer or a mesh network via machine-to-machine communication. Context information can include daily routine information (which may change especially from weekdays to weekends) from a calendaring application. Context information can include a frequency of touching or grabbing the monitoring device, even if not interacted with, based on a sensed motion of the device.

Photos can provide contextual information. For example, photos of one or more of: a glucose meter reading, an insulin pen or pump JOB, a location (e.g., a gym, park, house, Italian restaurant), or a meal may be used to provide context information. The photos may be processed to identify, for example, caloric intake for the meal shown in the photo. The type of insulin used may also be provided to the monitoring system as a useful contribution to the clinical context information. Context may also be provided by basal or bolus settings provided to or determined by the monitoring device.

Other inputs to the clinical context information which constitute context/behavioral data may include data types referenced elsewhere in non-context/behavioral inputs, such as exercise information from a fitness bike or the like, glucose sensor information from a blood glucose (BG) meter or CGM, insulin delivery amounts from insulin delivery devices, insulin on board calculations for the device, and other device provided or calculated information. Other context/behavioral data inputs to the GUI determination may include: hydration level, heart rate, target heart rate, internal temperature, outside temperature, outside humidity, analytes in the body, hydration inputs, power output (cycling), perspiration rate, cadence, and adrenaline level, stress, sickness/illness, metabolic/caloric burn rate, fat breakdown rate, current weight, BMI, desired weight, target calories per day (consumed), target calories per day (expanded), location, favorite foods, and level of exertion.

For any of the above referenced behavior or contextual inputs, the system may be configured to receive and/or generate analytical metrics based on the inputs. For example, a composite value may be generated based on the glucose level, temperature, and time of data generated index value for the user. The composite value may then be considered in the determination of the contribution to the clinical context information from the behavior and contextual information.

This information can be collected from various sensors within or outside of the device, such as an accelerometer, GPS, camera data, and the like, as well as third-party tracking applications, including sleep cycle applications. For example, such tracking applications may employ geolocation to determine context and behavior. Moreover, context and behavior may also be determined by use of social networking information available about the user, where a social networking feed, associated with the user, is arranged to provide a source of data in forming the clinical context information.

Additional details about context and behavior information may be found in U.S. Patent Publication No. US-2015-0119655-A1, owned by the assignee of the present application and herein incorporated by reference in its entirety, and in particular at FIG. 4 and accompanying text.

Signals and signal analysis, as well as clinical context information, are further discussed below in the context of the description of specific methods, as well as in several examples.

Figure 5:
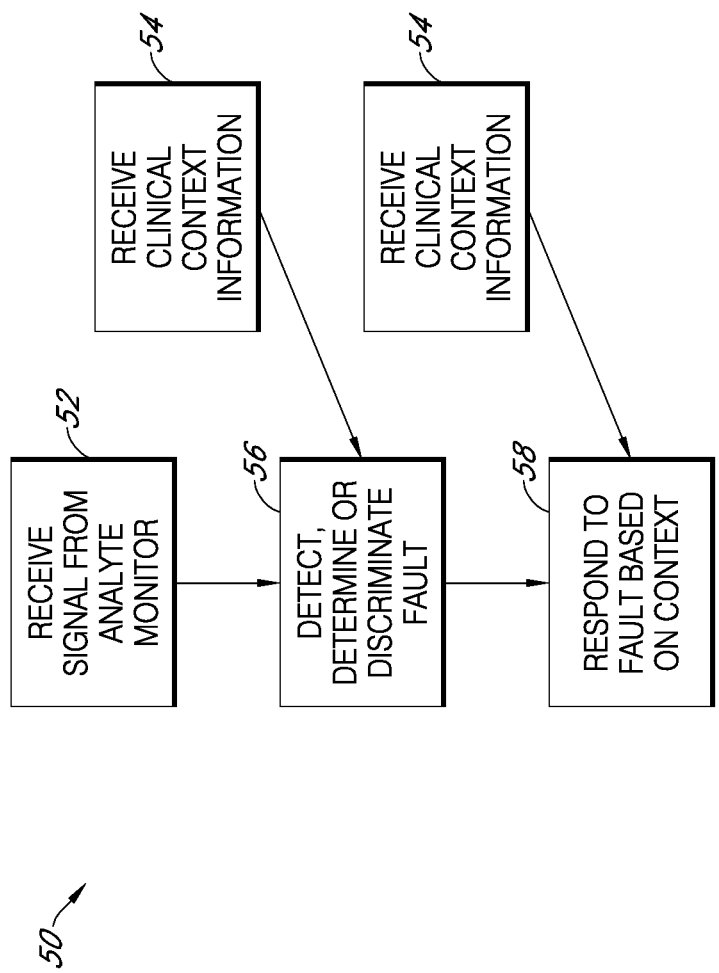
FIG. 5 is a flowchart of a method according to present principles.

As noted in FIG. 5, clinical context information may be used both in fault discrimination as well as in responsive processing. The following figures detail these methods. Referring first to FIG. 12A, a flowchart 222 illustrates a first regime (regime I) in which fault discrimination occurs from signal analysis alone, without regard to clinical context information. In this regime, a first step is to discriminate the fault from the signal alone (step 228). Clinical context information may then be received or otherwise determined (step 232). The discriminated fault is then responded to based on the context (step 234). In other words, there are two separate metrics, i.e., the signal data and the clinical context, and the former is used as a single metric to discriminate the fault and the latter determines the responsive signal processing (given the particular discriminated fault).

The table of FIG. 12B illustrates regime I in another way. First, a signal behavior SBi leads to a corresponding discriminated fault DFi. In the same way, a context variable VCj leads to corresponding clinical context data CDj. SBi and CDj are then used to determine a responsive processing RPji.

For example, and referring to the graph 236 of FIG. 12C, in which as before the abscissa axis 126 represents time and the ordinate axis 136 represents the raw signal, a steep downward trend 237 (SBi) is seen in the raw signal 235, accompanied by noise, which then flattens out and has less noise or variability 239 on the flattened portion. These signal characteristics may indicate by themselves a fault of compression (DFi). If one of the variables (VCj) known about the clinical context of the user indicates that it is the usual time for the user to go to sleep (CDj), then the responsive processing (RPji) may be to do nothing. On the other hand, if one of the variables known about the clinical context of the patient indicates that it is unlikely the user is sleeping (CDk), the responsive processing may be to perform self diagnostics (RPki) or to prompt the user to check their sensor.

As another example, the same detected fault may be handled differently depending on other aspects of the clinical context. For example, a variation in responsive processing may occur based on whether the measured glucose level is high versus low, or whether the rate of change of glucose level is slow versus fast.

Figures 13A, 13B:
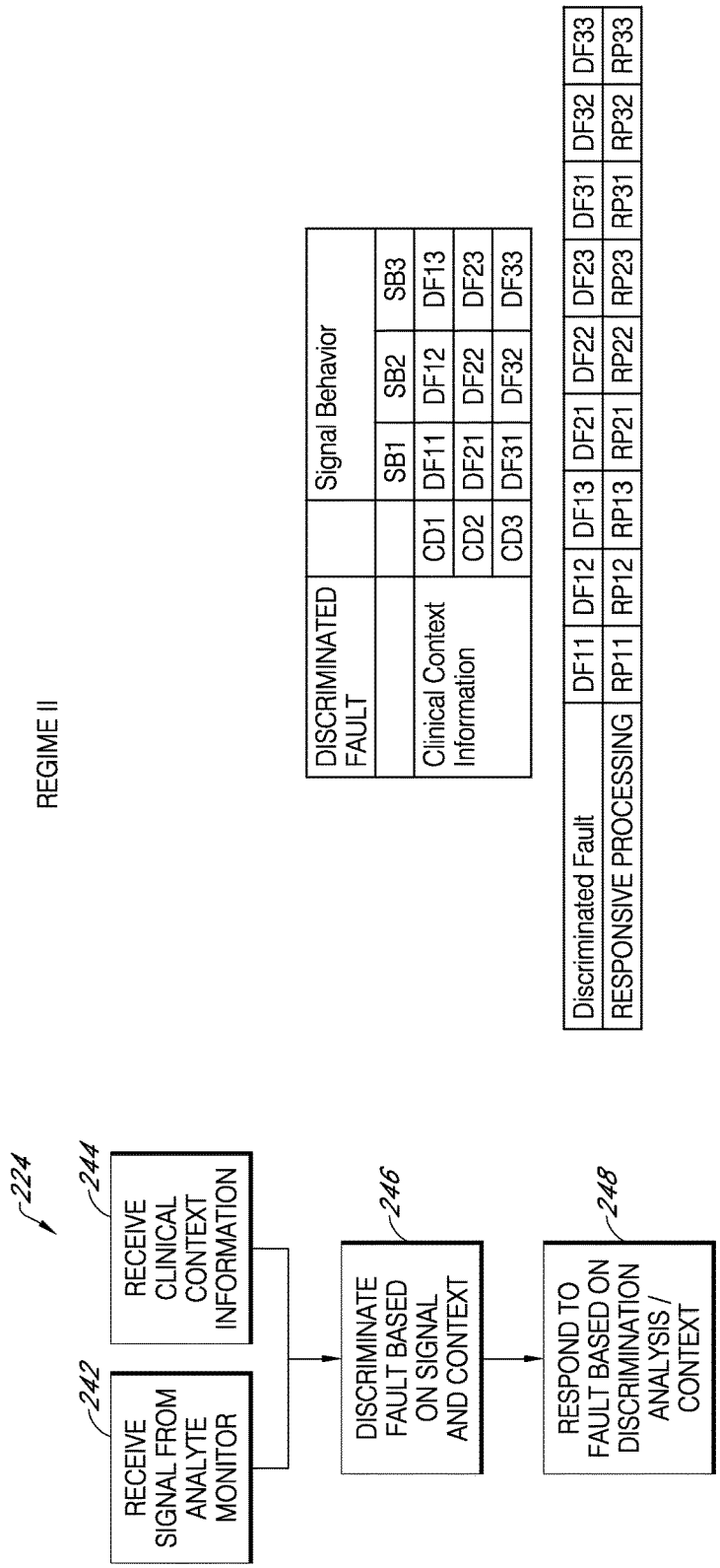
FIGS. 13A-13C illustrates aspects of a second regime of fault discrimination and responsive processing.

Next, regime II is illustrated in FIG. 13. FIG. 13A shows a flowchart 224 in which fault discrimination occurs from signal analysis in combination with clinical context information. In this regime, a first step is to receive the signal from the analyte monitor, and optionally perform any of the various signal processing functions described above (step 242). Prior to, subsequent to, or contemporaneous with the reception of the signal, clinical context information may be received or determined (step 244). The fault is then discriminated based on the signal and the received clinical context data (step 246). In other words, two separate metrics are used to discriminate the fault, i.e., signal data and clinical context, rather than just one as in regime I above. The fault is responded to appropriately, based on the fault itself (step 248).

The table of FIG. 13B illustrates regime II in another way. First, a signal behavior SBi is used in combination with clinical context data CDj to lead to a corresponding discriminated fault DFji, which is a fault discriminated not just on the basis of the signal data but also on the basis of clinical context data. Responsive processing RPji is then directly based on the discriminated fault DFji.

Figure 13C:
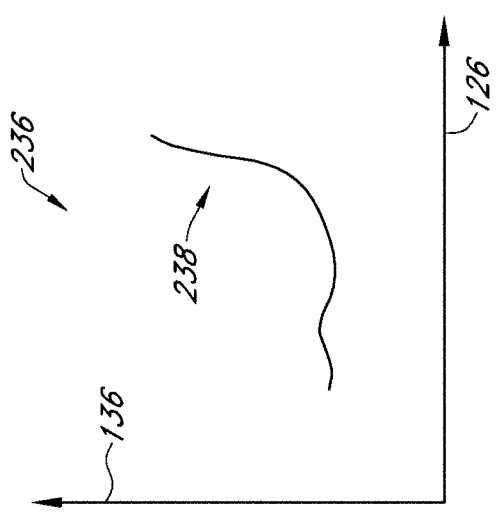

For example, and referring to the graph 236 of FIG. 13C, a steep upward trend 238 in the raw signal (SBi) may potentially indicate a fault of water ingress, but the indication is ambiguous because other factors could also cause such behavior. If one of the variables (VCj) known about the clinical context of the patient indicates that it is the usual time for the user shower (CDj), then CDj may be used in combination with SBi to disambiguate the fault and discriminate a fault of water ingress (DFji). Then the responsive processing (RPji) may be to do nothing. On the other hand, if one of the variables known about the clinical context of the patient indicates that it is unlikely the user is showering (CDk), then the fault DFki may be discriminated and the responsive processing may be to perform a step of self diagnostics (RPki).

Figures 14A, 14B:
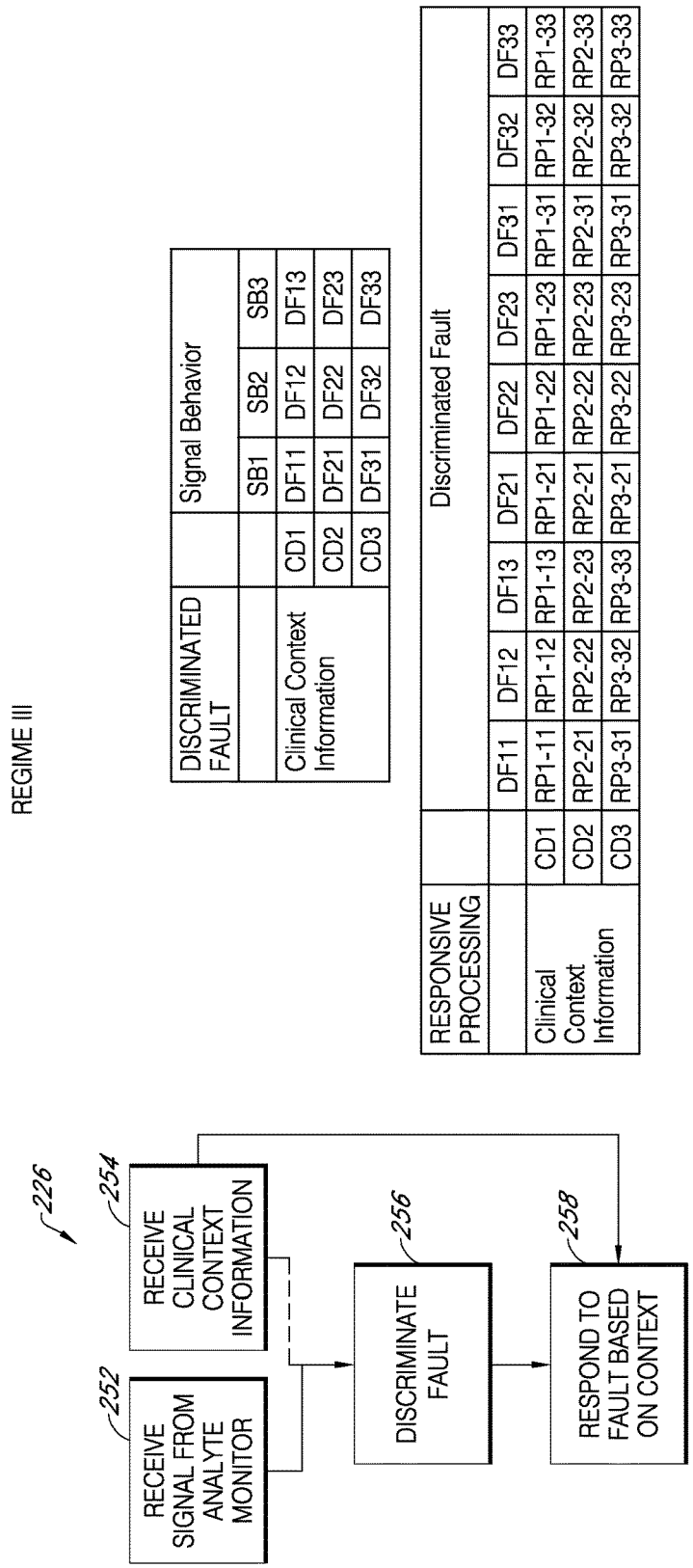
FIGS. 14A-14B illustrates aspects of a third regime of fault discrimination and responsive processing.

Finally, regime III is illustrated in FIG. 14. FIG. 14A shows a flowchart 226, in which fault discrimination occurs from signal analysis optionally in combination with clinical context information, but where clinical context information is also used to drive the responsive processing. In this regime, a first step is to receive the signal from the analyte monitor, and optionally perform any of the various signal processing functions described above (step 252). Prior to, subsequent to, or contemporaneous with the reception of the signal, clinical context information may be received or determined (step 254). The fault is then discriminated based on the signal and optionally also on the received clinical context data (step 256). The fault is responded to appropriately, based on both the fault and the clinical context (step 258).

The table of FIG. 14B illustrates regime III in another way. First, a signal behavior SBi is used optionally in combination with clinical context data CDj to lead to a corresponding discriminated fault DFji, which is a fault discriminated on the basis of the signal data and optionally also on the basis of clinical context data. The discriminated fault DFji is then used in combination with clinical context data CDk to determine a step of responsive processing RP (k-ji).

Figure 15:
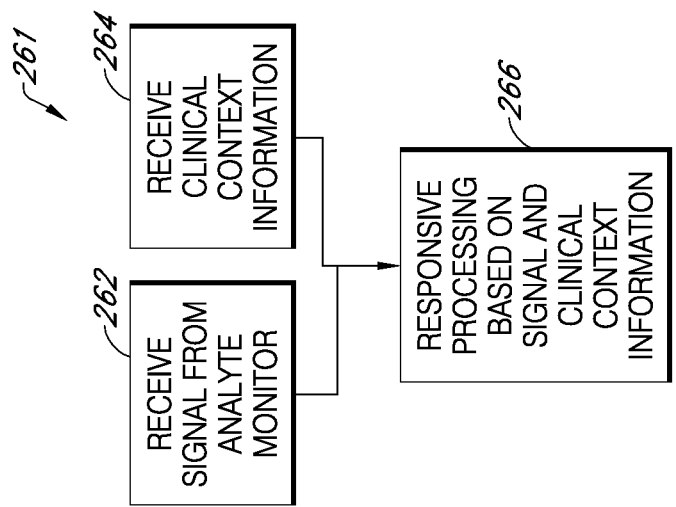
FIG. 15 is a flowchart of another exemplary method according to present principles.

The above regimes are exemplary, and it will be understood that other regimes are also possible. For example, and referring to the flowchart 261 of FIG. 15, in some cases it may not matter how the fault discrimination is characterized and/or discriminated, so long as both the signal data (step 262) and the clinical context (step 264) are taken into consideration when determining responsive processing (step 266). That is, the fault discrimination or categorization may not be required as a separate step.

In another variation, a "zone of indifference" may be defined for one parameter, factor, or variable (collectively, "metrics"), e.g., clinical glucose value, or for many or all of these, e.g., clinical glucose value, rate of change, smoothness of trace, etc. In such a zone of indifference, faults may be prohibited or suppressed because the effect or danger of a fault is defined to be low. Conversely, a "zone of danger" may also be defined in which faults are always discriminated and in which responsive processing always occurs.

In some cases, just a single input may be employed to determine clinical context information, where the single input is compared against clinical context criteria and the results of the comparison used to determine the clinical context information. The single input may be based on the signal received from a sensor, e.g., a CGM sensor, or may be based on a different type of input, e.g., time of day. In other cases, multiple inputs may be employed to determine clinical context information about one or more faults, wherein one or all of the multiple inputs are compared against clinical context criteria and/or otherwise combined by a mathematical formula.

In any of these regimes, the discriminated fault may be determined to fall into one of several predetermined fault categories, and the response to the fault may then be at least in part determined by the category the fault is in. Exemplary fault categorization schemes are now described.

Figure 16:
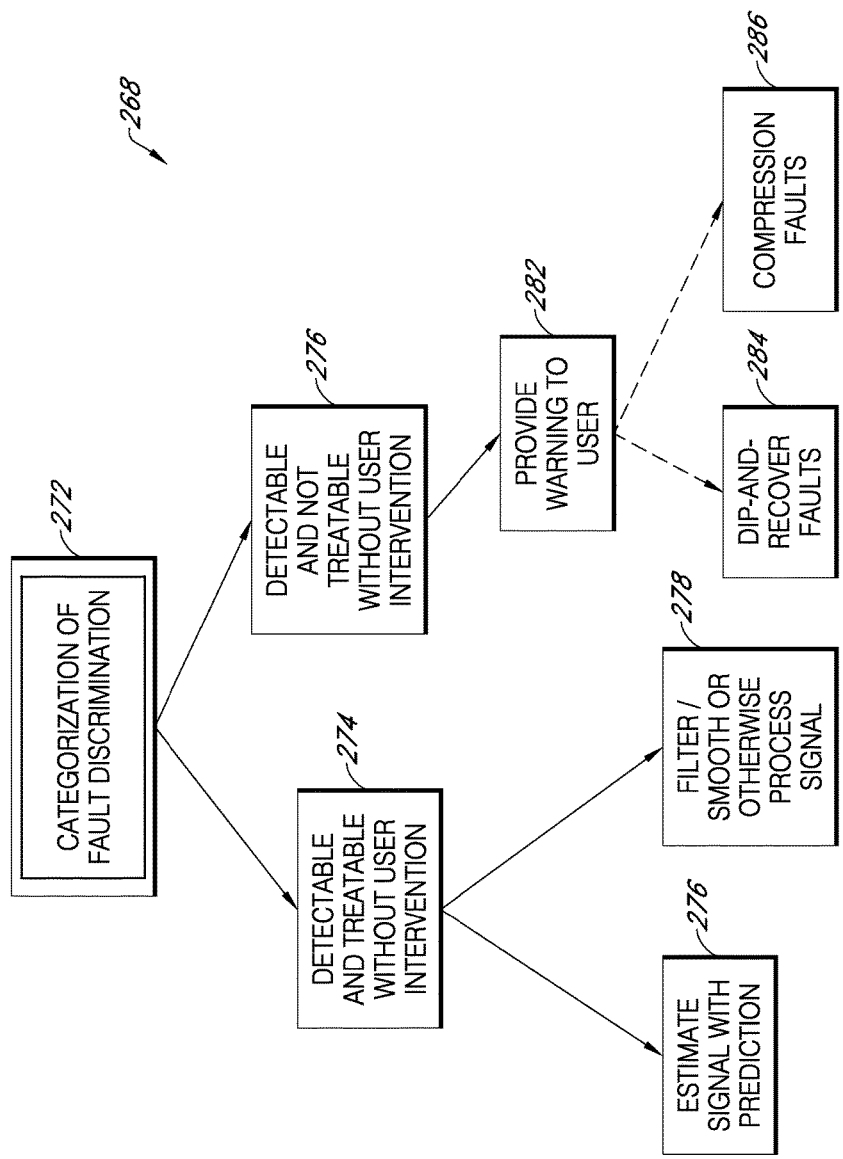
FIG. 16 illustrates one categorization scheme for fault discrimination.

Referring to the diagram 268 of FIG. 16, a fault categorization scheme illustrated. In this scheme, a categorization scheme 272 of fault discrimination may be broadly categorized into two types: those faults 274 that are detectable and treatable without user intervention, and faults 276 that are detectable but not treatable without user intervention, where user intervention corresponds to the user performing an act to correct the fault, e.g., "rolling over" if a compression fault, providing information to confirm a fault type, e.g., answering a prompted question or providing a reference glucose value, or performing treatment of their diabetes without the use of the CGM data, e.g., treating diabetes based on their meter value. For faults 274, various processing steps may be undertaken to provide service to the user until such time as the fault is alleviated or otherwise responded to. For example, an estimated or predicted signal 276 may be provided to the user. Alternatively, a processed signal 278 may be provided to the user, where the processing includes steps of filtering, smoothing, or other steps as required to reduce the effect of the fault. For example, where the signal undergoes a rapid upswing, typical of a water ingress fault, the signal may be replaced with a short-term prediction. Alternatively, if random noise is encountered, the signal can be filtered or smoothed.

In the other categorization, faults 276 are detected but cannot be fully responded to by the system. In this case, a warning 282 may be provided to the user that the displayed clinical glucose value, or GUI, may be inaccurate or should not be relied upon. Two examples are given in FIG. 16. First, a dip-and-recover fault 284 may be encountered, e.g., corresponding to an early wound response. With such a fault, a user may be warned that their glucose level may be incorrect. Another example is a compression fault 286. If this type of fault is detected, the responsive processing may be to prompt the user to change position.

It is noted that the above relates to responsive processing or other actions taken once a fault is discriminated. The act or step of fault discrimination itself entails steps of signal analysis and optionally also knowledge of clinical context. The responsive processing generally follows from the fault discrimination.

Figure 17:
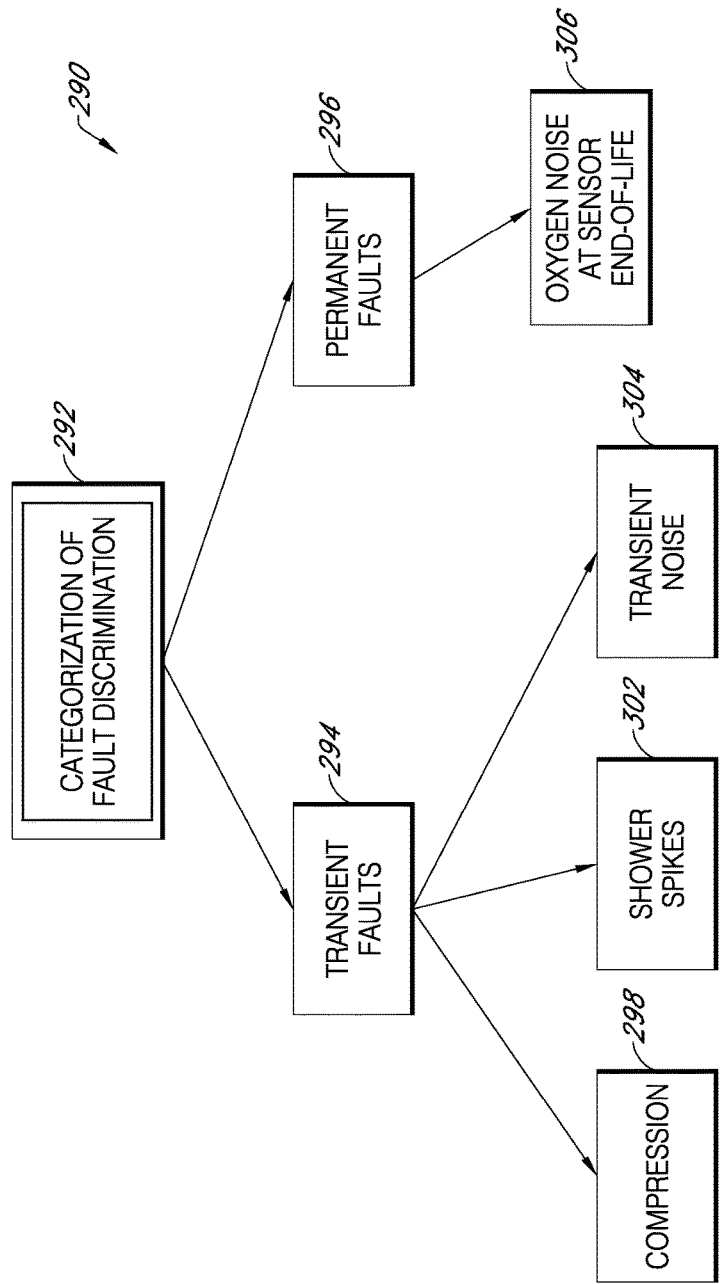
FIG. 17 illustrates another categorization scheme for fault discrimination.

The diagram 290 of FIG. 17 illustrates yet another categorization scheme 292 which may be employed in fault discrimination. In the categorization scheme 292, faults are divided into transient faults 294 and permanent faults 296. Transient faults 294 are those that tend to self-alleviate or self-cure, e.g., faults 298 related to compression, faults 302 related to shower spikes, and faults 304 related to transient noise. Permanent faults 296 are those that are not cured or remedied over time, including oxygen noise 306 encountered at the end-of-life of the sensor.

Figure 18:
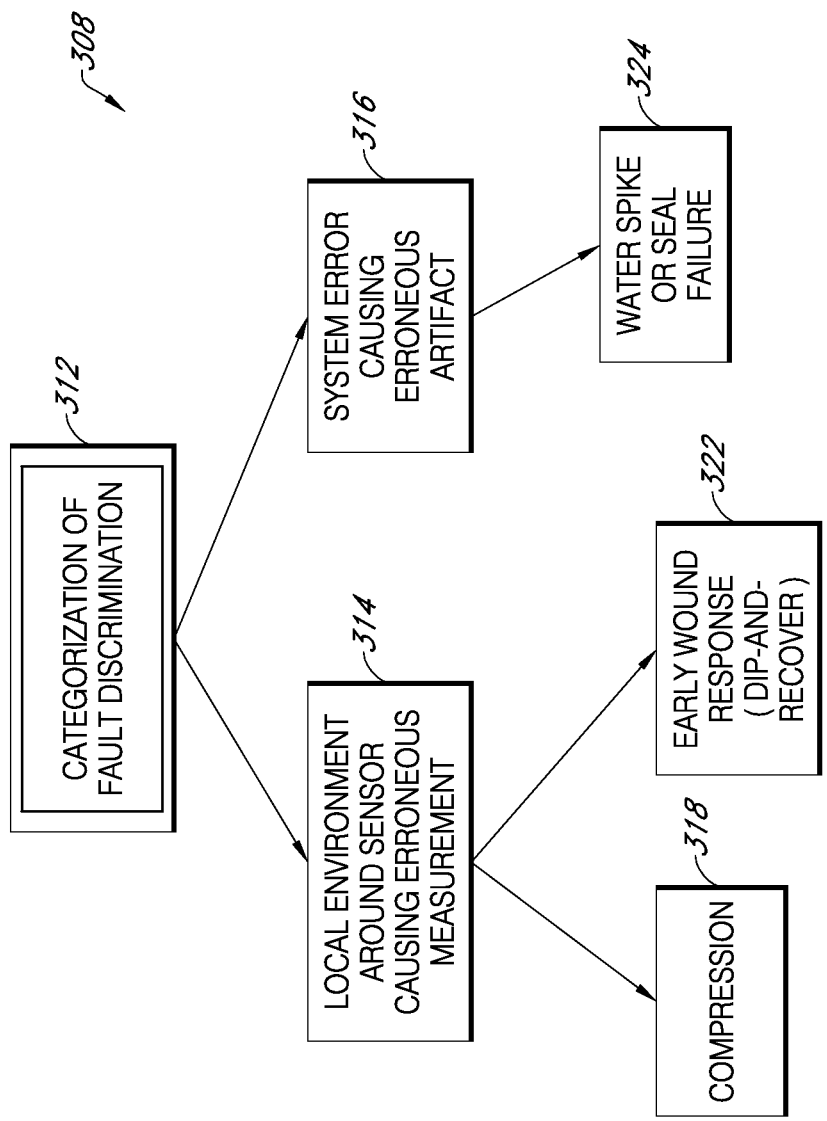
FIG. 18 illustrates a further categorization scheme for fault discrimination.

The diagram 308 of FIG. 18 illustrates yet another categorization scheme which may be employed in fault discrimination. In a categorization scheme 312, exemplary fault categories are indicated, categorized by a specific technical category. For example, faults are divided into faults 314 relating to the local environment around the sensor causing an erroneous measurement, and faults 316 relating to system errors which in turn cause erroneous signal artifacts. The faults 314 tend to be more compartmentalized and local. Examples of faults 314 include faults 318 relating to compression and faults 322 relating to early wound responses. An example of a fault 316 includes those relating to water spikes, which in many cases are caused by seal failures.

In each of these cases, i.e., compression, early wound response, and a water spike or seal failure, as well as with other signal behaviors, there would exist predetermined signal criteria used by the fault discrimination and responsive processing routine or algorithm. If the received signal meets the criteria, the fault category would be assigned accordingly.

Predetermined signal criteria for compression faults 318 may be based on a type of noise pattern and/or a rate of change of the raw signal, i.e., typically downward. Compression faults are generally not preceded by post-prandial rises, which are typically associated with a rise in signal accompanying ingestion of a meal. Other exemplary signal criteria for compression faults are that the same tend to be more binary, from one state to another, and not a smooth transition. Other signal criteria that may be examined in the context of compression faults are for signals that appear to follow patterns not associated with physiological changes. Predetermined criteria for clinical context information for compression faults may include the time of day, e.g., night time, when a sleeping user may roll onto their sensor, as well as accelerometer data, which may also indicate sleeping, or heart rate information, which may be slower for a sleeping user, as well as impedance data. As an example of compression in an intravenous system, where the glucose sensor is placed intravenously, increased impedance can result from the sensor resting against the wall of the blood vessel, for example, producing non-glucose reaction rate-limiting noise due to oxygen deficiency. The use of impedance data in determining clinical context information is explained more fully in U.S. Patent Publication No. US-2012-0265035-A1, owned by the assignee of the present application and herein incorporated by reference in its entirety. Exemplary uses of impedance data, as well as devices to calculate impedance, are described below.

Other data that may be employed as predetermined clinical context criteria include whether a meal has been recently ingested, or whether insulin has been recently delivered, as often compression faults are not preceded by a meal or medicament delivery.

Another fault category mentioned above pertains to early wound responses, one variety of which is a temporary wound healing response, termed "dip-and-recover". Without wishing to be bound by theory, it is believed that dip-and-recover may be triggered by trauma from insertion of the implantable sensor, and possibly also from irritation of the nerve bundle near the implantation, resulting in the nerve bundle reducing blood flow to the implantation area. Alternatively, dip-and-recover may be related to damage to nearby blood vessels, resulting in a vasospastic event. Generally any local cessation of blood flow in the implantation area for a period of time leads to a reduced amount of glucose in the area of the sensor. During this time, the sensor has a reduced sensitivity and may be unable to accurately track glucose. Thus, dip-and-recover typically manifests as a suppressed glucose signal. Dip-and-recover often appears within the first day after implantation of the signal, most commonly within the first 12 hours after implantation. Importantly, dip-and-recover normally resolves within 6-8 hours. Identification of dip-and-recover can provide information to a patient, physician, or other user that the sensor is only temporarily affected by a short-term physiological response, and that there is no need to remove the implant as normal function will likely return within hours. Additional details may be found in U.S. Patent Publication No. US-2014-0005509-A1, owned by the assignee of the present application and herein incorporated by reference in its entirety.

Exemplary signal criteria which may be employed to detect dip-and-recover faults include: a severe decline in signal, indicating the physiological conditions noted above, data about time since implant, as well as internal sensitivity measurements. Patterns may also be employed, where such patterns have been previously identified with such faults. A signal repeating such a pattern may be inferred to be indicative of a dip-and-recover fault.

Exemplary clinical context criteria which may be employed to detect dip-and-recover faults include pattern analysis, where the base pattern is defined by a clinical glucose profile for the patient. Current signals can be compared against such patterns to determine whether the current signals are outside normal glucose patterns for the patient. Patterns may also be established and used to determine if the patient is at a higher risk for wound response type faults, e.g., does the patient have a pattern of encountering such faults.

Besides dip-and-recover, other wound responses may also be the cause of faults and thus can be categorized within their own category or as part of a broader wound effect category. Appropriate responsive processing can then be defined for such faults. Exemplary signal criteria for other wound responses include impedance measurements between the working electrode and an external electrode to measure increases in electrochemical impedance between the physiological environment and the working electrode. Such impedance measurements are described in greater detail elsewhere.

In another exemplary fault category, a local effect at the sensor may prohibit the analyte such as glucose from being measured properly. Examples of this type of fault or error include those in which the membrane of the sensor has been deleteriously affected. In general, however, such faults are characteristic of sensors nearing an "end-of-life" period. For example, biofouling can cause such a fault. In this case, exemplary signal criteria may include the amount of time since sensor implantation, as well as certain characteristic noise patterns. Other criteria include increased noise at higher glucose levels compared to that at lower glucose levels. In yet other signal criteria which may be employed to detect faults due to such local effects of the sensor, an impedance measurement between the working electrode and an external electrode may be employed to measure increase in electrochemical impedance between the physiological environment and the working electrode. Comparative responses at different electrode potentials may also be employed.

Besides biofouling, oxygen noise may similarly be a fault caused as a local effect at the sensor or membrane. Exemplary signal criteria for oxygen noise include a number of episodes of a similar signal characteristic. This may be contrasted with, e.g., the biofouling fault above, in which there are several "small" episodes before larger episodes start appearing. In other words, in biofouling faults, there are several episodes of lower frequency and duration before larger episodes appear of higher frequency and longer duration. In general an increase in the signal frequency over the sensor session may be a criterion of an oxygen noise fault.

In these "local effect" faults, the clinical context may also be used in a determination of how to respond. In one type of responsive processing, the monitor may only display or rely on glucose values at "low glucose" levels, e.g., those below 100 mg/dL, as noise is more likely at high glucose levels.

Another type of fault involves the sensor end of life ("EOL"). In particular, embodiments of continuous glucose sensors described herein may have a useful life in which a sensor can provide reliable sensor data. After the useful life, the sensor may no longer be reliable, providing inaccurate sensor data. The signs of EOL may be recognized and any resulting user safety or in convenience may be prevented. To prevent use beyond the useful life, some embodiments notify a user to change the sensor after it has been determined that the sensor should no longer be used. Various methods can be used to determine whether a sensor should no longer be used, such as a predetermined amount of time transpiring since the sensor was first used (e.g., when first implanted into a user or when first electrically connected to sensor electronics) or a determination that the sensor is defective (e.g., due to membrane rupture, unstable sensitivity or the like). Once it is determined that the sensor should no longer be used, the sensor system can notify a user that a new sensor should be used by audibly and/or visually prompting a user to use a new sensor and/or shutting down a display or ceasing to display new (or real-time) sensor data on the display, for example.

In some embodiments, a plurality of risk factors may be evaluated that are indicative of sensor EOL, for example using risk factor instruction(s), algorithm(s) and/or function (s). In general EOL symptoms are progressive, e.g., not all symptoms (or episodes) indicate sensor failure. Each of the risk factors may be evaluated periodically or intermittently as often as with the receipt of sensor data (e.g., every 5 minutes) or more intermittently (e.g., every few hours or every day). The risk factors can be iteratively determined, averaged or trended over time and the results used in later processing. In some embodiments, the evaluation of one or more risk factors may be triggered by another event, such as a trended error in BG (e.g., from outlier detection) meeting one or more criteria.

In some embodiments, detection of EOL may be achieved using a combination of methods that each individually detect of EOL signatures or risk factors. The combination of methods or signatures may result in improved specificity (e.g., low false positives). It should be appreciated that the EOL determination methods or algorithms can use a combination of the risk factors in determining EOL.

In some embodiments, suitable risk factors may be selected from the list including, but not limited to: the number of days the sensor has been in use (e.g., implanted); sensor sensitivity or whether there has been a decrease in signal sensitivity (e.g., change in amplitude and/or variability of the sensitivity of the sensor compared to one or more predetermined criteria), including magnitude and history; noise analysis (e.g., EOL noise factors (skewness, spikiness, & rotations)), duration, magnitude and history, spectral content analysis, pattern recognition); oxygen (e.g., concentration and/or whether there is a predetermined oxygen concentration pattern); glucose patterns (e.g., mean, variability, meal characteristics such as peak-to-peak excursion, expected vs. unexpected behavior such as after a meal if glucose is not rising as expected); error between reference BG values and EGV sensor values, including direction of error (whether BG or EGV is reading higher as compared to the other); and measure of linearity of the sensor (or the lack thereof). Sensor linearity refers to a consistency of the sensor's sensitivity over a particular range of measurement (e.g., 40-400 mg/dL for glucose sensors). For example, when the sensor signal is reading low with low BG and high with high BG, linearity may be assumed vs. when the sensor signal is reading low with low BG but not reading high with high BG (not changing or increasing beyond a certain BG value), where non-linearity may be assumed (based on error between reference BG values and EGV sensor values).

One risk factor that may be useful in the determination of EOL is the number of days the sensor has been in use (e.g., implanted). In some embodiments, the number of days the sensor has been in used is determined based in part on using initial calibration data, sensor initialization, operable connection of the sensor with sensor electronics, user entered data, or the like. In some embodiments, the system may detect sensor restart and uses restart information in the determination of the days since implantation.

In some embodiments, when a certain threshold has been met, e.g., a certain number of days, the particular variable associated with the threshold may be automatically used in the EOL function. For example, if the number of days the sensor has been in use is determined to be at least 4 days, then the number of days the sensor has been in use is automatically used and/or a simple yes/no indicator that the threshold has been met. In some embodiments, if the number of days the sensor has been in use is at least ⅓ of the days the sensor is approved for use, then the number of days the sensor has been in use is automatically used. In other embodiments, if the number of days the sensor has been in use is at least ½, ⅔, or ¾ of the days the sensor is approved for use, or the like, then the number of days the sensor has been is automatically used. In some embodiments, the actual number of days the sensor has been in use is always used in the EOL function. In some embodiments, the EOL function is performed after a predetermined number of days of sensor use.

Additionally or alternatively, time elapsed from insertion may be mapped to an EOL risk factor value (e.g., likelihood of recovery or probability of sensor failure in future) because the longer a sensor has been in use since implantation, the more the sensor-tissue interface changes (biofouling) will likely impact sensor function. In one example, the EOL risk factor value is mapped to about 1.0 between days 1 and 5 and reduces gradually beyond day 5 reaching to 0.5 at day 8, 0.2 at day 10, and about 0.1 at day 14. Other values and thresholds may be used as may be appreciated by a skilled artisan.

Another risk factor that may be useful in the determination of EOL is sensor sensitivity or whether there has been a decrease in signal sensitivity (e.g., change in amplitude and/or variability of the sensitivity of the sensor compared to one or more predetermined criteria), including magnitude and history. In some embodiments, the processor module may be configured to determine if there has been a drop in signal sensitivity. For example, for some sensors, their sensitivity drifts up or remains relatively flat over most of the life of the sensor, e.g., 3, 5 or 7 days. Towards the EOL, the sensitivity of the sensor to changes in glucose may decrease. This reduction may be recognized as a drop in sensitivity that occurs monotonically over several hours (e.g., 12 hours), either by determining: (a) a change in sensitivity (e.g., m in raw_signal=m*glucose+baseline) or (b) a reduction in sensor raw count signal. For example, the following equation may be used:

> If median(raw count over last 12 hours)−median(raw count over last 12-24 hours)<2*standard deviation over the last 12 hours, then the sensor may be nearing EOL.

In some embodiments, other forms of signal descriptive statistics related to signal sensitivity (e.g., median, percentiles, inter-quartile ranges, etc.) may be used to detect EOL. In some embodiments, whether there has been a decrease in signal sensitivity involves a determination that compares a measured signal sensitivity against a predetermined signal sensitivity threshold or profile to determine if the measured signal sensitivity is within an acceptable range. The acceptable range may be based on a priori information, such as from prior in vitro and/or in vivo testing of sensors. In some embodiments the measured signal sensitivity is outside an acceptable range, then the signal sensitivity may automatically be used in the EOL function. In some embodiments, the measured signal sensitivity, a change in sensitivity and/or an indicator of a predetermined sensitivity decline may be used as an input or a variable in the EOL function.

In some embodiments, the sensitivity variable in the EOL function is based on a trend of sensitivity during a particular sensor session (e.g., during the life of the sensor in the host). For example, the determination of whether there has been a decrease in signal sensitivity includes comparing a first measured signal sensitivity at a first time point against a second measured signal sensitivity at a second time point to determine if rate of change in the measured signal sensitivity is within an acceptable range. The acceptable range may be determined by a priori information, such as from prior in vitro and/or in vivo testing of sensors. In one example, a change of greater than 20% over one day may be an indicator of EOL and useful as an input in the EOL detection function. In one example, a rate of acceleration (e.g., rate of drop of sensitivity) of greater than 20% over 12 hours may be an indicator of EOL and useful as an input in the EOL detection algorithm.

In some embodiments, the rate of change of signal sensitivity may be determined based in part on a slow moving average of raw sensor data (e.g., counts). This embodiment takes advantage of the fact that for most patients, the average glucose over time (e.g., a few days or more) remain relatively constant; thus, a change in the average of the sensor data (e.g., uncalibrated (raw or filtered) over time (e.g., 2, 3, 4, 5, 6, 7 days or more)) may be interpreted as a change of sensitivity of the sensor over time. The results of the slow moving average could be a quantifiable amount and/or simple yes/no indicators of a sensitivity decline that may be useful as one input or variable into the EOL function.

For example, the processor module may use an average of the last x hours (e.g. for 24 hours), a rectangular window averaging or an alpha filter with an exponential forgetting factor to compute the slow moving average to evaluate sensor sensitivity over time. In one example of an alpha filter with exponential forgetting, 'alpha' may be used as follows:

parameter($n$)=parameter($n-1$)*(1-alpha)+ new_info*alpha wherein alpha defines how much of history one wants to remember (how soon to forget). In the above equation, alpha is a "forgetting factor." Alpha may vary between 0 and 1, and its value dictates how fast old measurements are forgotten by the model. For values of alpha close to 1, the model adapts more quickly to recent measurements. For values of alpha close to 0, the model adapts more slowly to recent measurements. The value of alpha may depend on the elapsed time since the sensor was implanted. If alpha is 0.01, then in 1/0.01 (i.e., time constant of 100) samples, 63% of previous information is forgotten. Accordingly, if a sampling rate is 12 samples/hr, then 63% of the signal would be forgotten by 100 samples, e.g., ~8 hours. In such an example, it would follow that with three time parameters or constants, which is about 1 day, only 5% (i.e., 0.37*0.37*0.37=0.05) of signal left from the previous day would remain. It is further noted that the calculation may be recursive or non-recursive.

In some embodiments, sensitivity loss may be indicative of EOL. Sensitivity loss may occur towards the sensor EOL due to physiological wound healing and foreign body mechanisms around the sensor or other mechanisms including reference electrode capacity, enzyme depletion, membrane changes, or the like.

In some embodiments, sensor sensitivity may be computed using an analysis of uncalibrated sensor data (e.g., raw or filtered). In one example, a slow moving average or median of raw count starts showing negative trends, the sensor may be losing sensitivity. Loss of sensitivity may be computed by calculating a short term (e.g. ~6-8 hours) average (or median) of the sensor output and normalizing it by the expected longer term (48 hours) average sensor sensitivity. If the ratio of short term to long term sensitivity is smaller than 70%, there may be a risk of sensor losing sensitivity. Loss of sensitivity may be translated into an EOL risk factor value, for example a value of about 1 until the ratio is about 70%, reducing to 0.5 at 50% and <0.1 at 25%.

Alternative computations for risk of EOL related to sensitivity may use external references such as glucose finger stick readings. In either case, specific estimated sensitivity loss may be transformed into EOL risk factor values using functions described elsewhere herein.

In some embodiments, sensor sensitivity may be computed by comparing sensor data (e.g., calibrated sensor data) with reference blood glucose (BG). For example, calibration algorithms adjust the glucose estimates based on the systematic bias between sensor and a reference BG. EOL algorithms may use this bias, called error at calibration or downward drift, to quantify or qualify EOL symptoms. The error at calibration may be normalized to account for irregular calibration times and smoothed to give more weight to recent data (e.g., moving average or exponential smoothing). In some embodiments, EOL risk factor value is determined based on the resulting smoothed error at calibration. In such embodiments, EOL risk factor value is 1 for all values of error at calibration>−0.3, and reduces to 0.5 at error at calibration=−0.4, and to <0.1 for error at calibration=−0.6.

Another risk factor that may be useful in the determination of EOL is noise based on a noise analysis e.g., EOL noise factor (skewness, spikiness, & rotations), duration, magnitude and history, spectral content analysis, pattern recognition, etc. In some embodiments, the processor module may be configured to evaluate the noise (e.g., amplitude, duration and/or pattern) to determine if there is a predetermined noise pattern indicative of EOL. For example, typical sensor EOL signature may include an increase in spike activity, which can be detected using various methods of spike detection (e.g., by computing the mean rate of negative change).

In some embodiments, the duration of the noise may be indicative of EOL. Some noise detection algorithms that may be useful are described in further detail in U.S. Pat. No. 8,260,393, incorporated herein by reference in its entirety. In some embodiments, the inputs to the calculation of noise duration risk factor metric are the noise categorization of sensor data. For example, each raw sensor count may be categorized as clean, light noise, medium noise or severe noise based on the relative magnitude of sensor and filtered sensor counts and their derivatives. This information may be used to translate severe noise duration (e.g., amount of sensor data that are in severe noise state) into a metric that reflects EOL risk. An assumption behind the calculation of this metric is that sensor EOL manifests as episodes if continuous noise is detected rather than intermittent noise of a few samples. Thus, EOL algorithm may penalize the longer duration noise more. Thus, at each sample time, total duration of noise up to the point is used to calculate the EOL risk factor value at that point.

In some embodiments, whether there is a predetermined EOL signature (noise pattern) involves a determination that includes evaluating the measured signal using pattern recognition algorithms to determine and identify predetermined EOL signatures in the sensor signal. For example, by comparing the measured sensor signal against a noise pattern characteristic of end of noise, it may be determined if the recorded noise pattern is similar to the predicted noise pattern.

In other embodiments, the determination of whether there is a predetermined noise pattern (EOL signature) includes comparing the measured signal against a predetermined noise pattern to determine if the recorded noise pattern is similar to the predetermined noise pattern. For example, the predetermined noise pattern may include a series of specific negative spikes in a short time frame. The predetermined noise pattern may also include an increase in spike activity for a given time frame.

In one embodiment, threshold detection for rate of change may be used to detect upward or downward spikes. Spikes may be detected by various ways as may be appreciated by one skilled in the art. For example, point to point difference and thresholding, sharpness filters, etc. For example, an algorithm or function may output a +1 for an upward spike and a −1 for a downward spike. Using this spike data time series, one may use either upward spike detection algorithms or downward spike detection algorithms or total spike detection (e.g., positive or negative spike time series) algorithms.

In some embodiments, EOL detection using these spike detection functions may be achieved using a negative threshold on the moving average of spike time series (e.g., 2 times negative spikes than positive) or a threshold (e.g. 3 or 4) on total spike activity showing a 3 to 4 times increase in total spike activity. Other forms of spike detection such as least squares acceleration filters may be employed. In some embodiments, an EOL risk factor value may be determined to be 1 for a value of a spike metric <1, and reduced to 0.5 for a spike metric >2, and to <0.1 for spike metric >5, and so on.

In addition to or alternatively, high frequency activity or patterns may be used in EOL detection. For example, EOL signature patterns may show a significant increase in high frequency activity when a power spectral density (PSD) or a Fast Fourier Transform (FFT) is performed on the sensor data. Normal glucose signal has very low frequencies (e.g., 0 and 1.8 mHz). Consequently, a high pass filter or a band pass filter may be used to detect the EOL pattern associated with high frequency activity.

In some embodiments, a slow changing long-time scale average signal may be used to normalize the data to enhance the reliability of detection methods, e.g., signal sensitivity or noise pattern. For example, by using the following definitions:

Long_time_scale=long time (1-2 day) moving average or filtered raw glucose data
Signature=short term (~4-6 hrs) filtered (any including spike detection) data
Normalized_Signal=Signature/Long_time_scale Thresholds for normalized signal and duration constraints may be applied to detect EOL signatures. Consequently, EOL may be detected if:
Normalized_Signal>Threshold for greater than certain Duration.

In some embodiments, the threshold and duration may be optimized to achieve specific sensitivity and specificity. Alternatively, having a short duration constraint may be used to detect oxygen noise instead of EOL.

In some examples, EOL noise may be determined to be sensor EOL specific based on various algorithms that evaluate known EOL failure modes identifiable on the signal. It may have large (>30% point to point drop) downward spikes, negatively skewed over the duration of an episode, with intermittent rapid rotations or oscillations, e.g., multiple peaks and valleys or number of derivative sign changes. Noise discrimination can use these features to identify if a sensor shows EOL symptoms and depending on the magnitude and duration, can calculate the EOL risk factor value from an episode, which may also be termed the noise factor.

Another risk factor that may be useful in the determination of EOL is oxygen (e.g., concentration and/or whether there is a predetermined oxygen concentration pattern). For example, in some embodiments, the processor module may be configured to determine if there is predetermined oxygen concentration and/or trend or pattern associated with the oxygen concentration. Any oxygen sensor useful for quantifying an oxygen concentration may be useful here, separate from or integral with the sensor. In an electrochemical sensor that includes a potentiostat, pulsed amperometric detection can be employed to determine an oxygen measurement. Pulsed amperometric detection includes switching, cycling, or pulsing the voltage of the working electrode (or reference electrode) in an electrochemical system, for example between a positive voltage (e.g., +0.6 for detecting glucose) and a negative voltage (e.g., −0.6 for detecting oxygen). In some embodiments, oxygen deficiency can be seen at the counter electrode when insufficient oxygen is available for reduction, which thereby affects the counter electrode in that it is unable to balance the current coming from the working electrode. When insufficient oxygen is available for the counter electrode, the counter electrode can be driven in its electrochemical search for electrons all the way to its most negative value, which could be ground or 0.0V, which causes the reference to shift, reducing the bias voltage such as described in more detail below. In other words, a common result of ischemia will be seen as a drop off in sensor current as a function of glucose concentration (e.g., lower sensitivity). This happens because the working electrode no longer oxidizes all of the H2O2 arriving at its surface because of the reduced bias.

In some embodiments, a non-enzyme electrode or sensor may be used as an oxygen sensor. In an exemplary dual working electrode sensor, having enzyme and no-enzyme working electrodes, the non-enzyme electrode may be used as an oxygen sensor by changing the bias potential from a positive value (e.g., 600 mV-800 mV) to a negative value (e.g., negative 600 mV-800 mV). At this potential, dissolved oxygen is reduced and gives rise to a negative current through the non-enzyme electrode. In some embodiments, by switching the bias potential on the non-enzyme electrode between the indicated positive and negative biases, a bi-functional electrode results. When a positive bias is applied, the current may be related to baseline and when a negative bias is applied, the current may be related to the local oxygen concentration.

It is known that glucose oxidase based sensors are limited by the amount of oxygen present. When the oxygen level reduces below a threshold value, the enzyme electrode current drops ("oxygen starvation") while the glucose concentration remains constant. This oxygen starvation may result in reduced accuracy, as lower than actual glucose levels may be reported. Oxygen starvation can occur late in sensor life, such as when the sensor is encapsulated in the subcutaneous environment. Consequently, being able to measure oxygen allows the detection of this encapsulation and EOL for the sensor.

In some embodiments, whether there is a predetermined oxygen concentration pattern involves a determination that includes reviewing the oxygen concentration pattern to see if the oxygen concentration is appropriate. For example, an oxygen concentration pattern that shows reduction in oxygen availability over time may be indicative of EOL of the sensor.

Another risk factor that may be useful in the determination of EOL is glucose pattern (e.g., mean, variability, meal characteristics such as peak-to-peak excursion, expected vs. unexpected behavior such as after a meal if glucose is not rising as expected).

Still another risk factor that may be useful in the determination of EOL is error between reference BG values and corresponding calibrated sensor data (estimated glucose value, or EGV), including direction of error (e.g., whether BG or EGV is reading higher as compared to the other) and/or utilizing flagged outliers. In some embodiments, the system may identify discrepancies between reference values (e.g., BG) and sensor values (e.g., EGV). For example, when there is a large difference in the reference values and sensor values, something is likely not working correctly. In certain embodiments, a large discrepancy between the reference values and sensor values may indicate end of sensor life. While not wishing to be bound to any particular theory, this is believed because the sensor is reading either higher or lower than it should. In some embodiments, the direction of the error, for example whether the BG is higher or lower than the EGV is used as an EOL indicator. Still another risk factor that may be useful in the determination of EOL is a measure of linearity of the sensor (or the lack thereof). As described above, sensor linearity refers to a consistency of the sensor's sensitivity over a particular range of measurement (e.g., 40-400 mg/dL for glucose sensors).

In some embodiments, the processor module is configured to evaluate the various risk factors to provide EOL risk factor values, which may include simple binary (yes/no) indicators, likelihood or probability scores (e.g., relatively scaled or percentages) and/or actual numbers (e.g., outputs of the various tests). The risk factor values may be scaled if the weights used in the algorithm are modified.

In some embodiments, the processor module is configured to run probability functions to determine a probability of EOL and/or a likelihood of recovery for one or more of the plurality of EOL risk factors. In some embodiments, risk factors are mapped to a score (e.g., from 0 to 1) based on one or more parameters. The score may be mapped by functions, which translate a particular risk factor or set of risk factors to an EOL risk factor value, indicating for example, a possibility of the sensor to recover from a particular risk factor from EOL. Other methods of translating risk factor outputs into EOL risk factor values may be used as is appreciated by a skilled artisan, such as by using one or more criteria, algorithms, functions or equations.

In some embodiments, risk factors are fuzzified using pre-determined membership functions in order to quantify their propensity to indicate EOL. As used herein, a membership function defines the degrees to which a condition is satisfied, or a degree to which a value belongs to a fuzzy set defined by that function. In binary logic, a number would either satisfy a condition fully or not at all; in fuzzy logic, a number can satisfy a condition to a certain degree described by a membership function.

As an example of a binary indicator function, a noise level is compared to a hard threshold, such as "5"; any value below 5 (such as 4.9) is treated as being noise-free and any value above 5 (such as 5.1) is treated as having an unacceptable level of noise. As an example of a fuzzy membership function, a sigmoidal shape may be used to define a smooth transition in the evaluation of the noise levels. The inflection point of the curve is set at 5, so there is no discontinuity at that point. Thus, the same values of noise (4.9 and 5.1) as above are now treated very similarly. Fuzzification is the determination of the degree to which a value belongs to a fuzzy set defined by a particular membership function.

In some embodiments, each of the plurality of risk factors is partially indicative of the EOL of the sensor if each variable is determined to meet a threshold. In some embodiments, if at least two of the plurality of risk factors are determined to meet a threshold, then the combination of the at least two risk factors is indicative of the EOL of the sensor.

The system may be configured to determine an EOL status. In one embodiment, a likelihood or probability analysis may be used to determine an EOL status of the sensor. The outputs of the risk factors become inputs into an EOL determination process. For example, the outputs of the risk factors may be mapped to EOL risk factor values, for example values from 0 to 1, probability or likelihood scores, actual values (outputs from the risk factor evaluation(s)), and/or the like. The EOL risk factor values then become inputs into the EOL determination function, whereby the risk factors may be weighted or otherwise processed using a probability analysis, decision matrix, various subroutines or the like, to determine an actual EOL indicator, a probability (or likelihood) of EOL, a predicted time to EOL, or the like. Probability functions, decision functions, various subroutines, or the like may be implemented as the EOL determination function as is appreciated by one skilled in the art.

In one embodiment, decision fusion may be used as the function through which the various inputs are processed. Decision fusion may provide a Fused Bayesian likelihood estimate based on sensitivity and specificity of individual detector algorithms associated with each input or variable. Suitable risk factors are measured and fused together to determine whether or not a sensor has reached EOL. A decision can be made for "yes" EOL or "no" EOL based on each individual risk factor. For example, if sensor sensitivity has decreased by more than $\Delta m$ over some amount of time $\Delta t$ then "yes" EOL otherwise "no", or if the sensor has had severe noise (above a predetermined threshold level) for more than 12 hours of the last 24 hours then "yes" EOL, otherwise "no".

The individual decisions can be combined into a single Bayesian likelihood value that can be used to make the best final decision about EOL, using the sensitivity and specificity of each variable in detecting EOL. First, each decision is converted to a likelihood value using the following equation:

$$\lambda(d) = \frac{P(d|H_1)}{P(d|H_0)}$$

where d is a binary decision of 0 or 1 (no or yes), H1 is the case that EOL is present, H0 is the case that EOL is not, and P( ) is the probability function. In practice, this means for a "yes" decision $\lambda$=sensitivity/(1−specificity), and for a "no" decision $\lambda$=(1−sensitivity)/specificity. For an individual variable test with high sensitivity and specificity, λ will be very high for a decision of 1 and very small for a decision of 0.

In some embodiments, the individual likelihood values are multiplied together for a final fused likelihood value that takes into account the ability of each individual variable to separate EOL from non-EOL. Thus, more sensitive and specific tests will be given greater weight in the final decision. A threshold may be determined empirically for the final fused likelihood values to achieve the best separation of EOL and non-EOL.

In some embodiments, linear discriminant analysis (LDA) may be used as the EOL determination function, by taking the input variables and providing an output decision.

In some embodiments, when EOL inputs or variables are fuzzified using pre-determined membership functions, resulting degrees of membership for all data quality metrics are scaled according to pre-determined weights and combined to produce an indicator of the overall quality of the computed glucose value. The weights may be applicable to every metric and may show how indicative a metric is of EOL. These embodiments may use several fuzzy logic concepts such as membership functions and fuzzification, as described above, to determine the degree of severity of each data quality metric. The result of the EOL detection may be a confidence indicator that determines a likelihood of EOL beyond a simple pass/fail criterion.

In some embodiments, EOL status may be determined based on likelihood of a sensor not recovering from an event, rather than occurrence of an event; the likelihood of a sensor not recovering may be defined as the state when a sensor is likely to be no longer accurate or has long episodes of noise (e.g., based on risk factor evaluation(s)). The EOL indicator may also indicate a possibility of recovery (e.g., when the episode may be transient rather than terminal). In some embodiments, the system may be configured to determine a likelihood of recovery and/or monitor the sensor or sensor data over the next x hours to determine whether the sensor may recover from the EOL symptoms (e.g., the likelihood of sensor providing accurate data to user in next 24 hours). In some embodiments, the sensor will only be determined to be at EOL if a high probability of sensor not tracking glucose in the future (e.g., 24 hours) or not showing glucose at all for several hours (e.g., 12 hours) is determined (e.g., inaccuracy may be determined by a comparison of EGV with reference BG using a standard (e.g., within 20% or 20 mg/dL)).

The system may optionally be configured to monitor the risk factors (e.g., for example more frequently after EOL indicator determines a likelihood of EOL) to determine whether it is more than likely that the sensor will not recover from the EOL determination. Functions or algorithms suitable for determining whether a sensor will recover from EOL may be selected from those known by one of skill in the art. For example, determining whether a sensor will recover may be a 0 to 1 scaling based on an evaluation of one or more risk factors.

In some embodiments, the system may be configured to determine, based on recent history, the likelihood of a sensor to recover from the EOL determination. For example, the EOL determination function may determine the EOL status is more than likely if there is a high probability that the sensor will not track glucose in the future or that the sensor is not detecting glucose at all for extended durations. Extended durations may include time periods exceeding 12 hours. In some embodiments, the processor module is configured to suspend display of sensor data during verification or determination of a likelihood of recovery, after which the processor module may be configured to either re-allow display of sensor data if it is determined that the sensor has recovered from the EOL symptoms.

In some embodiments, intermittent signs of EOL may be used to turn on advanced signal filtering techniques. Such filtering techniques are described, for example, as described in more detail in U.S. Pat. No. 8,260,393, which is incorporated herein by reference in its entirety.

In some embodiments, the monitoring application may initiate a countdown timer which, upon expiration, requires or suggests insertion of a new sensor.

Additional details of "end-of-life" sensor issues are found in U.S. Patent Publication No. US-2014-0182350-A1, owned by the assignee of the present application and herein incorporated by reference in its entirety.

Returning to FIG. 18 and in particular faults 316, faults may be categorized as system errors, e.g., resulting in erroneous signal artifacts. In these faults, system errors such as those related to the sensor, connections within the sensor or sensor electronics, transmitter errors, and the like, may cause a variety of deleterious signal artifacts resulting in an unreliable analyte reading. One sub categorization includes a seal failure that can lead to a water spike. Exemplary predetermined signal criteria that may be employed to test signals for such faults include a change in the raw signal over a short period of time, e.g., a rapid positive rise. Other signals which may be used in this fault discrimination include the temperature of the sensor, which may indicate the patient has entered a shower or hot tub. Other exemplary signal criteria include time of day and/or signals from temperature sensors. It should be noted here that temperature is being employed in this context in the determination of clinical context information, and is being employed for the purpose of determination of clinical context, as opposed to use of the temperature per se, e.g., for temperature compensation. Thus for use as clinical context information, a measured temperature is generally compared to a clinical context criterion to determine clinical context information. The determination as noted often requires additional clinical context information to avoid ambiguity. For example, if the temperature of the sensor (the measured signal) rises to a certain value or rises a predetermined threshold above a certain value (the clinical context criterion), e.g., 5°, then such may indicate showering (the clinical context information). When considered along with other clinical context information, e.g., pattern data, such as a regular time of day for a shower, and/or signal data, e.g., a spike, may lead to the unambiguous evaluation of a water spike. Another sub categorization includes faults related to electrostatic noise, which may be caused by the rubbing of clothing on the sensor or electronics patch, especially during repetitive activities and dry weather. Signal information which may indicate such a fault includes analysis of the frequency content of the signal and comparison with fault discrimination criteria. Clinical context data may include indications of user movement or exercise, e.g., gleaned from accelerometer data on the transmitter or on an accompanying mobile device in data communication with the monitoring application.

Another sub categorization includes faults related to motion artifacts, such as those caused by exercise or other motion around the sensor patch area. Such faults may be especially common if the patient wears the sensor on their back upper arm or other similar location, as such locations are generally more susceptible to motion affecting the sensor site. Signal criteria which may be used to discriminate such faults include analysis of the signal shape itself, including morphological, time, frequency, and distribution aspects. Clinical context data for such faults include detection of exercise or activity level, such as may be gleaned from an accelerometer, GPS, user input, or the like.

A further sub categorization includes faults related to drift. For example, the drift may be in either of the quantities m or b, where y=mx+b, which is a regression equation where the slope M represent sensitivity of the sensor and the intercept b represents a background or offset. Signal criteria to discriminate such faults may include measuring a potential at a first time and measuring a potential at a second time, at the same electrode, and determining if a drift in m or b has occurred. Calibration errors may also indicate such drift faults.

Yet another sub categorization includes faults relating to poor connections and/or broken wires. A signal criterion which may be used to discriminate such faults includes detecting high-frequency noise, which may be characteristic of poor connections or broken wires. Fuzzy logic may also be employed to determine the type of noise, particularly as the same may be distinguished from other sorts of noise, e.g., during steep changes in rates of change.

Figure 19:
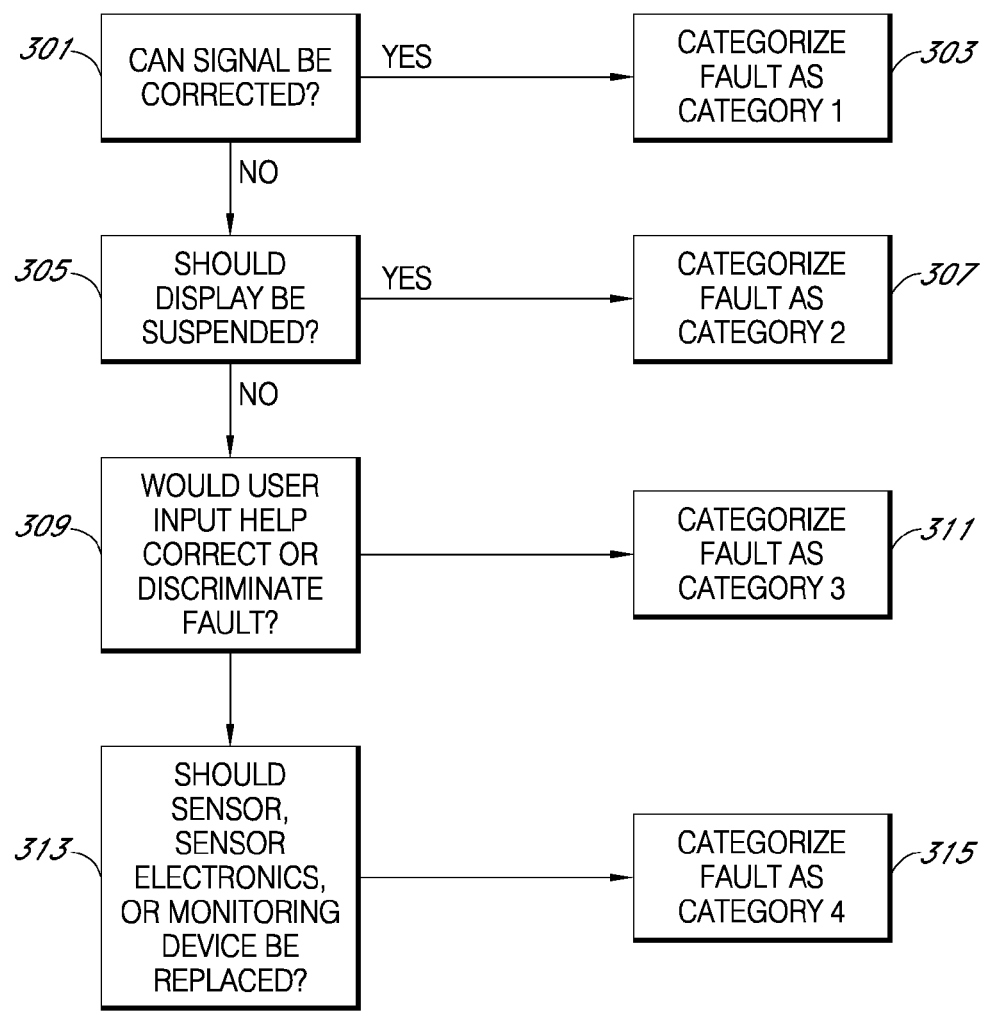
FIG. 19 is a flowchart of another exemplary method according to present principles.

Other categorization schemes will also be understood. For example, and referring to the flowchart 299 of FIG. 19, if the fault discrimination routine determines that the signal can be corrected (step 301), e.g., by a prediction or other sort of signal processing, then the fault may be categorized as a "Category 1 fault" (step 303) and signal processing appropriate for such may be applied. If not, the routine may determine if the display should be suspended (step 305), and if so the fault may be categorized as a category 2 fault (step 307), and display suspended. If display is not suspended, the routine may determine if user input would help correct the fault or discriminate the fault (step 309), and if so the fault may be categorized as a category 3 fault (step 311). In this case, such user input may be prompted for. Finally, the routine may determine if the sensor, the sensor electronics, monitoring device, or a combination of the same should be replaced (step 313). If so, the fault may be categorized as a category 4 fault (step 315). As with the above, for all of these categories, predetermined signal criteria and a predetermined clinical context criteria would be defined which, if met, would cause the fault to be associated with the one or more categories. It will be understood that the above steps may be performed in varying order.

As yet another example of a categorization scheme, a lookup table may be used by the routine which keys off certain signal behaviors and clinical context information. For example, referring to FIG. 20, a lookup table is shown which keys off of signal behaviors and two pieces of clinical context information. Exemplary signal behaviors and clinical context information are shown, but it will be understood that the limited number shown are for clarity and that generally many others may also be employed.

Similarly, a hierarchical approach to fault discrimination or categorization may be applied. Referring to FIG. 21, fault discrimination or categorization may occur by listing faults in their order of occurrence, e.g., from the most common fault to the least common fault, along with appropriate signal analysis and clinical context criteria for each respective fault. The algorithm or routine may then, starting with the most common fault, determine if the current signal analysis and clinical context data meet the criteria. If so, the analysis may end there and the fault or fault category may be determined from the table. If not, the analysis may continue to the next most common fault, again applying the current signal analysis data and clinical context information to the predetermined criteria for the given fault. By the process of elimination, the fault or fault category may be determined. As the faults are listed in order of their prevalence, such a hierarchical approach may lead to a rapid or in some cases optimized fault discrimination or categorization.

Yet another approach to fault discrimination or categorization includes use of "decision fusion" methods. In these methods, fault discrimination, categorization, or determination may be made from multiple inputs. Decision fusion uses a statistical model to optimally combine information from multiple inputs, e.g., clinical context data and signal analysis data, and produces a likelihood value that the data is associated with a particular fault or fault category. Such methods are particularly useful in combining heterogeneous inputs, like glucose rate of change and number of receiver button presses of the last twenty minutes, into a single likelihood scale. Prior information on the sensitivity and specificity of each input in predicting the undesired event, e.g., hypoglycemia, is used to determine how much weight to give each input in the final output.

Additional details about decision fusion methods are provided in U.S. Patent Publication No. 2014-0182350-A1, owned by the assignee of the present application and herein incorporated by reference in its entirety.

While the above description has discussed exemplary categorizations and fault types, as well as discriminating the same, it will be understood that any method for identifying a fault of a particular type or category may be used, whether qualitative or quantitative.

Responsive Signal Processing

Figure 22:
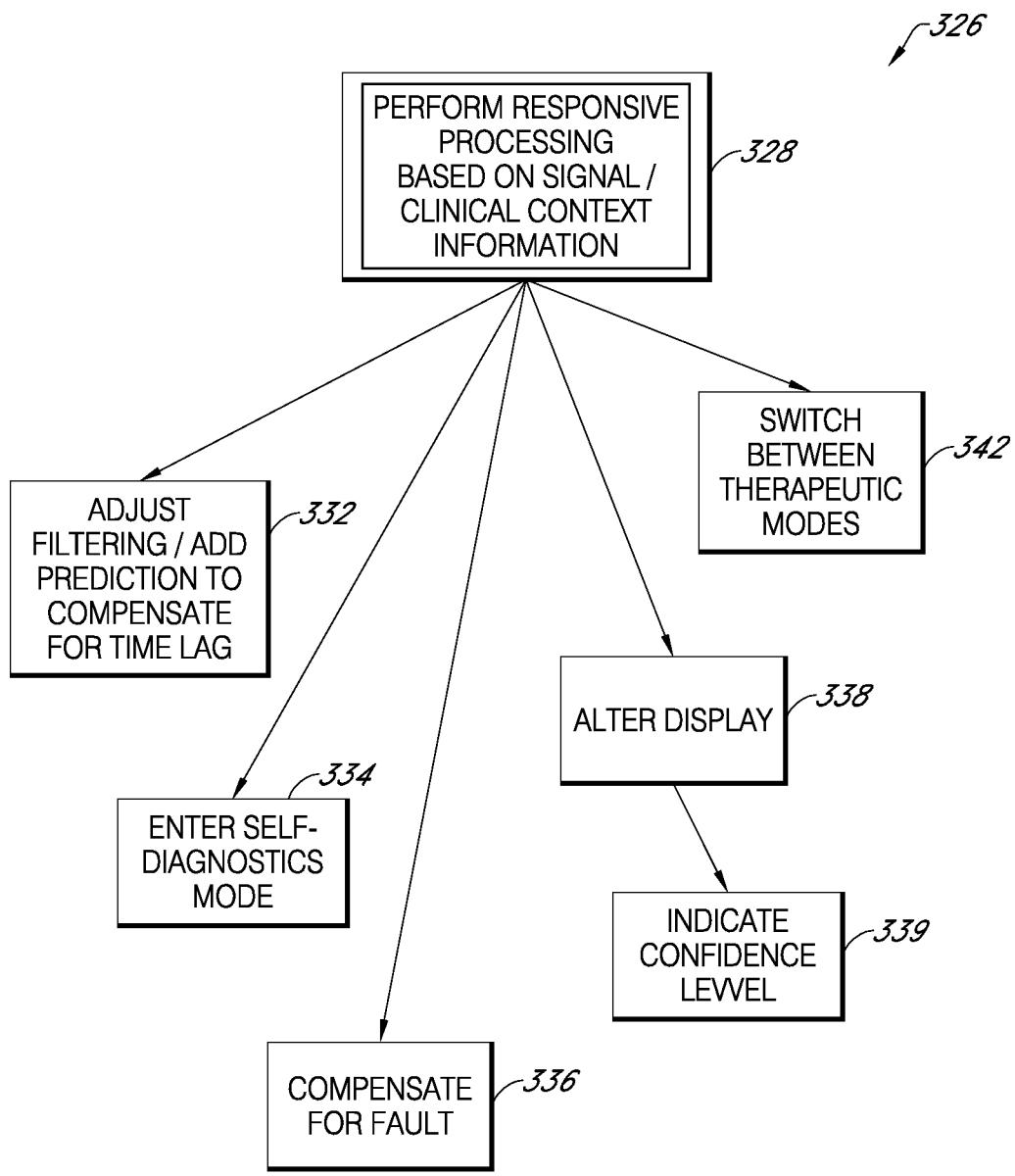
FIG. 22 illustrates types of responsive signal processing.

Various types of steps of responsive signal processing 328 are illustrated by the diagram 326 of FIG. 22. Steps taken in a given circumstance depend on the discriminated fault and the clinical context information, and particular examples are given below. The following are an exemplary but non-exhaustive list of such steps.

First, as discussed above in connection with faults that are detectable and treatable without user intervention, a step 332 may be employed in which filtering is adjusted or a prediction of an analyte concentration is made. These steps may be performed for number of reasons, including compensating for a time lag due to the fault or due to signal processing to compensate for the fault.

In the case of noise filtering, the same may be reduced during the clinical context of a high rate of change in analyte concentration. In this way, if an analyte such as glucose has a concentration that is rapidly changing, the reduced filtering will cause additional data points to be taken or received so as to obtain a more accurate picture of the user's glycemic state. In this way, the values during the rapid change may be more closely and rapidly followed, thereby enabling a more rapid response, where a response is called for. Conversely, filtering may be increased during the clinical context of a low rate of change of analyte concentration, particularly in high noise states. In alternative implementations, filtering may be enhanced by the use of fuzzy filtering as described above as well as below. Other techniques may also be employed in other implementations, including the use of regression and residuals, as described below in the context of FIG. 37.

Figure 23A:
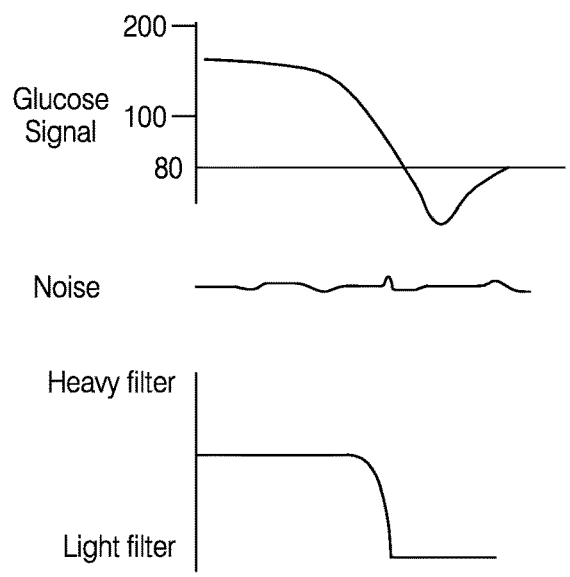
FIGS. 23A-23B illustrate selective filtering based on a signal and clinical context.

In more detail, filtering may be reduced during a clinical context of a low analyte concentration, e.g., a hypoglycemic state. In this way, the reduced filtering causes data points to be processed in a more timely fashion, i.e., with relatively less time lag as compared to more filtering. The situation is seen in FIG. 23A, in which a clinical glucose value is seen approaching a hypoglycemic state. The noise value is relatively stable. However, as the glucose value approaches or enters the hypoglycemic state, the level of filtering is lessened to provide a more responsive system as required to detect and treat hypoglycemic events.

Figure 23B:
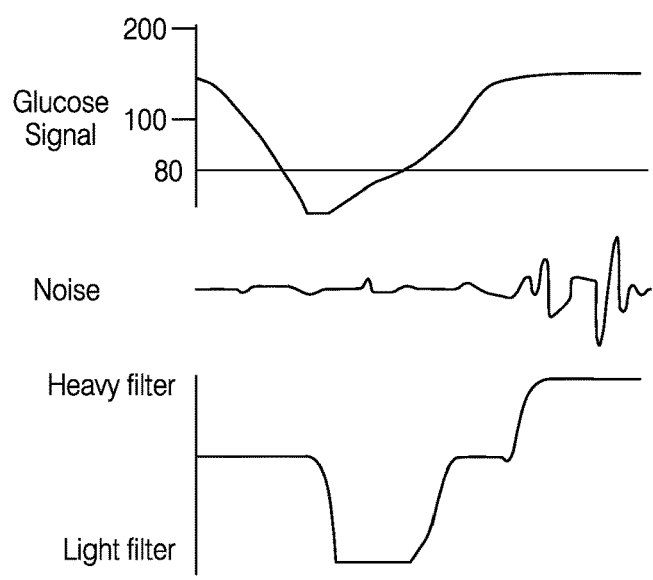

Another situation in which step 332 may be applied are those in which the noise is of a specific predetermined type or severity. In these cases, even without consideration of the clinical context, filtering may be adjusted, e.g., to increase filtering of particularly noisy signals or decrease filtering of especially smooth ones. This situation is illustrated in FIG. 23B, where again filtering is lessened during a period of hypoglycemia. The filtering is seen to go back to a normal value when the user is no longer in the hypoglycemic state. In addition, as the raw signal encounters greater levels of noise, e.g., where the user is running or jogging, an even heavier filter is applied. In general the filtering may be balanced based on noise type and severity, in addition to clinical context information such as the rate of change of the analyte concentration.

In a related step for responsive processing using signal processing or manipulation, the sampling rate may be altered as noted above with respect to FIG. 9. In particular, the sampling rate may be adjusted to a faster or slower rate to accommodate various fault situations. For example, if the fault is indicated by the sudden upward or downward direction of the raw signal, sampling may be automatically increased to allow additional data to be received, allowing a better understanding of the underlying phenomenon.

In another step of responsive processing, the bias potential may be changed to one that might be less susceptible to certain fault types, e.g., less susceptible to noise.

Returning to FIG. 22, another type of responsive processing is for the monitoring device to enter a self diagnostics mode (step 334). In this mode, the monitoring device may run a number of routines to test itself, and thereby to attempt to determine the source of a fault. In some cases the fault may be automatically remedied, and in other cases the fault may require user intervention. The level of user intervention may vary, e.g., from a relatively nonintrusive step of performing a calibration step to a more drastic step calling for replacement of the monitoring device. In self-diagnostic modes, a step of sweeping may be performed across varying potentials to determine proper behavior of the sensor, e.g., to detect a reference bias shift indicative of reference electrode depletion or instability due to ischemic conditions. Self diagnostics routines may also be run with transient signals, pulsed signals, or the like, and the same may be scanned over various frequencies. Such a mode may also be employed to test fault behavior at different potentials, as faults may behave differently at different electrode potentials or when the electrode potentials are switched, e.g., as evidenced by a transient response or decay curve. Self diagnostics routines may also test the transmitter, and may further perform comparisons of resolutions in the slow versus fast sampling techniques noted elsewhere.

A further type of responsive processing is to perform a step of compensating for the fault (step 336). For example, one type of compensation is to provide a predicted, forecasted, or expected analyte concentration value over the duration of the fault. For example, if an upward spike is seen in the raw signal value, but the clinical context indicates a high glucose value or euglycemia, and if other clinical context information indicates that the time of day is the morning, a water ingress fault such as may be caused during a morning shower may be inferred and the actual glucose value replaced with a predicted one, based on the value seen before the water ingress and, e.g., other clinical context information. Redundant signals and average signals may be used similarly. It is noted that the use of forecasting may depend on context, e.g., whether the user is sleeping versus ingesting a meal.

Forecasting may also be employed to compensate for time lag based on glycemic state. In particular, and as noted above, a time lag can lead to deleterious results, particularly during times of high rate of analyte concentration change and at low overall analyte concentration values. Accordingly, the use and display of forecasted or predicted values may be advantageously employed during these times.

However, in some clinical context the use of predicted values may be discouraged. For example, fault compensation by predicted values may be safe at high glucose values but may be more dangerous at low glucose values. In these situations, rather than performing a compensation step, the clinical context may indicate that the responsive processing should call for a finger stick measurement to be taken.

Besides providing a prediction, faults may be compensated for by the use of specific algorithms. For example, to compensate for the discriminated fault of compression, a max average algorithm may be employed, particularly where the clinical context indicates that the time of day is night time and the patient is above a certain clinical glucose value.

Other types of responsive processing will also be seen. For example, in multi-sensor systems (e.g., multi-electrode systems), described in greater detail below, redundant signals may be received and employed as noted above, and in such systems effects due to local sensor surroundings may be isolated and thereby compensated for. In yet another type of responsive processing, where a large amount of noise is present on the signal, the CGM value may be turned off and a very heavy or aggressive filter applied. The CGM may still provide a report, particularly on trends, but such would only include those seen through the aggressive filter. For an actual value of blood glucose, users may be prompted to use a finger stick.

The above-noted steps 332, 334, and 336 may be performed without significant user input, or even user knowledge that the steps are occurring. By contrast, many implementations of steps 338 and 342 below require user knowledge and in some cases user intervention.

For example, another type of responsive processing is to alter the display of the monitoring device (step 338). In this way, the user can be alerted to the situation, e.g., that the current glucose value is unreliable, and the user may further be prompted to input additional information which may be employed by the algorithm in further processing, e.g., to enter meal or exercise information. The user may also be alerted to perform certain steps to alleviate the fault. For example, during high noise periods, additional calibrations may be requested by the system, particularly if the user is near important values, such as hypoglycemic and hyperglycemic thresholds. Similarly, if the fault is discriminated as a compression fault, the user may be directed to relieve the compression from the sensor. The user may also be queried as to various potential causes of a discriminated fault, e.g., "WERE YOU LYING ON YOUR SENSOR?". In certain implementations, the user may be prompted to perform a finger stick to determine their actual blood glucose value, especially when the CGM is detecting a low glucose concentration value. The results of such measurements and queries may be fed back into a user profile and used later for personalized fault discrimination routines. In other words, adaptive or machine learning may be triggered and the system may thus become alerted to faults characteristic or typical of a given patient, enabling even more rapid actionable alerts.

In yet another implementation, the output could be provided with an indicator of the confidence with which the algorithm has computed the analyte concentration (step 339), e.g., a confidence level, a "fault index" indicating the type or severity of the current fault, or the like. Colors, of the display or the background, may be employed to discreetly indicate to the user data confidence. The output may be delayed, or a cautionary notice placed on the output. A range of potential analyte concentration values may be provided to indicate the inherent uncertainty in the data. Alert and alarm conditions may be modified or adjusted to account for uncertainties in the data due to faults, e.g., may be adjusted to more conservative values. Alternatively, certain alarms may be suspended to alleviate false or distracting warnings. Moreover, the output may be changed based on the confidence in data quality, e.g., via a confidence metric.

In more detail, there are various sources of inaccuracy and imprecision that may be present in an analyte monitor. These include noise and/or imprecision in the raw sensor signal, reference and calibration error, compartmental effects and analyte reference temporal mismatch, physiological foreign body responses, and transient electrical, chemical, and biological interference. These sources of error can be quantified by examining prior sensor data and/or using Monte Carlo-based error budgeting models. The combination of the errors results in inaccurate CGM glucose readings, but the degree of inaccuracy varies with varying conditions. For example, current subcutaneous sensors are well-known to have less accuracy during the first day of use compared to later days. Some sensors tend to perform less accurately during fast rates of change of glucose (as compared to steady state glucose trends). A cumulative accuracy measure fails to account for differences in accuracy between individual points. Errors can be visualized and examined in detail during post processing steps by utilizing Bland-Altman style plots or a Clarke Error Grid, but such tools are sometimes difficult to use, and are generally retrospective in nature.

One way of determining a confidence indicator is by the following technique. First, raw sensor data and diagnostic information are collected. Diagnostic information may include signal noise levels, local trend information, data from auxiliary sensors, or the like. This information is used in normal glucose value calculations, but can also be used to evaluate the confidence in the data. In the next step, all pieces of the data are evaluated according to empirical and/or adaptive criteria in order to determine the quality of various aspects of the signal, e.g., noise level, agreement with prior measurements, or the like. Intermediate calculations are performed, such as for sensor sensitivity and baseline, sensor working conditions, and so on. Operational characteristics are also evaluated according to separate sets of criteria to provide additional information. In this step, significant information is gathered and qualified to provide the confidence technique with enough to produce a good estimate of confidence.

Data quality metrics for all applicable pieces of information are then included using predetermined "membership functions" in order to quantify their propensity to cause inaccuracy in resulting glucose values. In the technique of fuzzy logic, such is termed "fuzzification" or being "fuzzified". Resulting degrees of membership for all data quality metrics are scaled according to predetermined weights and combined to produce an indicator of the overall quality of the computing glucose value. The weights are applicable to every metric, and show how indicative the metric is of an inaccurate glucose value. For example, relative contributions of different metrics to an overall confidence indicator may be as follows. A recent glucose value may have a quality of 19% in its propensity to cause inaccuracy, while the glucose trend consistency may indicate a 34% confidence indicator contribution, glucose signal stability may contribute 28%, and the pressure signal may contribute 19%.

The technique can then determine the degree of severity of each data quality metric. In the terms above, a membership function defines the degrees to which a condition is satisfied, or the degree to which a value belongs to a fuzzy set defined by that function. In conventional binary logic, a number will either satisfy a condition only or not at all; in fuzzy logic, the number can satisfy a condition to a certain degree described by a membership function. Fuzzy logic can then be employed to determine whether a level of noise in the signal is a cause for concern.

Figure 23C:
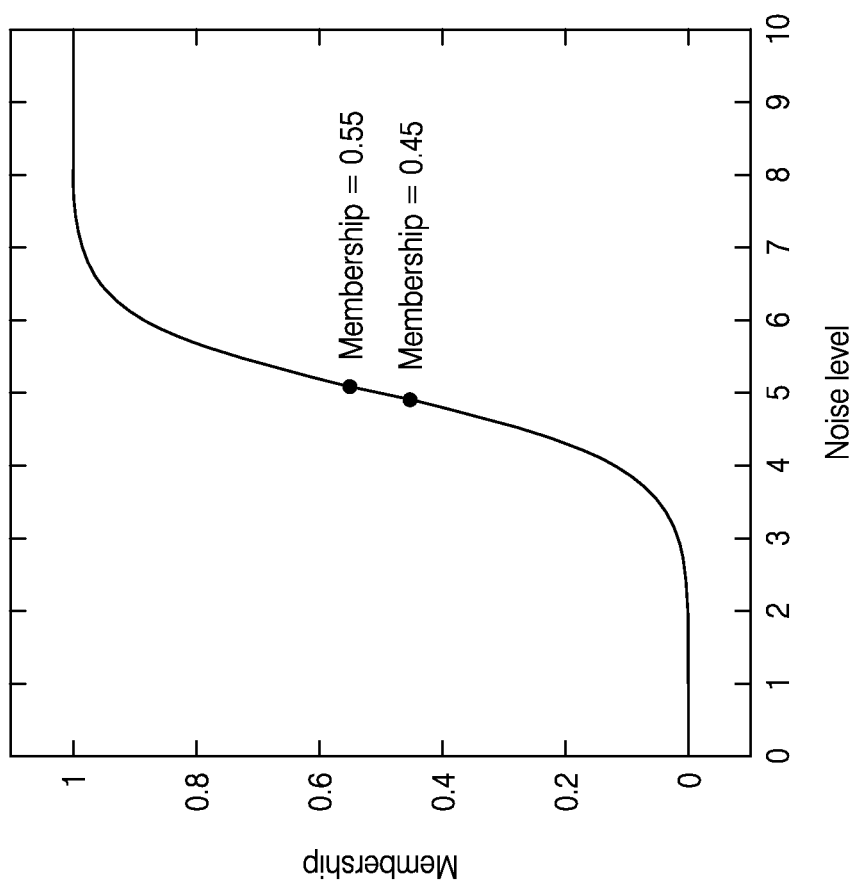
FIG. 23C illustrates a fuzzy membership function for the use of fuzzy logic.

FIG. 23C indicates a fuzzy membership function. The sigmoid shape defines a smooth transition in the evaluation of the noise levels. The inflection point of the curve is set at 5, so there is no discontinuity at that point. Thus similar values of noise, e.g., 4.9 and 5.1, are treated very similarly. Fuzzification is the determination of the degree to which a value belongs to a fuzzy set defined by a particular membership function, and the figure demonstrates the results of fuzzification of the values 4.9 and 5.1 using the provided membership function. The resulting membership values of 0.45 and 0.55 reflect both the levels of noise relative to a threshold in the similarity between the two levels of noise. Use of such fuzzy logic improves the accuracy of the system and the selectivity of the algorithm in marking the points with the potential to be inaccurate as unacceptable. The technique may increase the number of glucose values that are both accurate and displayed and decrease the number of values that are accurate but are erroneously blanked. Such may also help reduce the incidence of false alarms and provide the user with actionable alarms to aid in resolving the issues that arise with the data in the system.

Besides including such in the determination of noise, a confidence level indicator can be provided along with the displayed glucose value (step 339), and the same used for calculations. Advantages include that the confidence level indicator can determine whether a glucose value is acceptable or not, beyond a simple pass/fail criterion. Such may aid in eliminating single point failures as well as making analyte monitoring algorithms more intelligent in their classification of data.

Finally, in the step 338 of altering the display, it is noted that the output display may vary based on the clinical context information, even with a common value of the analyte concentration.

Returning again to FIG. 22, as yet another example of responsive processing, the monitoring device may be caused to switch between therapeutic modes (step 342). In this implementation, a fault may cause a closed loop or connected medicament pump to enter a mode where it is open loop or only semi-closed loop. Similarly, the system may change from having a therapeutic data usability to having an adjunctive data usability. Rather than basing pump actions on the clinical glucose value, the clinical glucose value may be provided to the user and the user may then control the pump action, or perform the affirmative step of acknowledgment or validation of the pump action, where the user is generally taking into account other known data. For example, such resort to open loop processing may occur upon discrimination of a dip-and-recover fault or a biofouling fault.

Similarly, the analyte monitor may be caused to enter a calibration mode, e.g., one in which the same is calibrated against a blood glucose meter calibration or the factory calibration. The calibration scheme may also be modified so as to affect the interpretation or weightings of values determined by finger sticks or other measurements. In a related technique, the system may instruct the user to provide a blood glucose finger stick value, but that calibration may be tagged as a known error, and the same employed for calibration purposes only until it is determined that the error or fault has been remedied, in which case the user is cued to provide an additional calibration point, and the system subsequently ignores the previously-determined faulty calibration point.

Even without switching modes, one type of responsive processing is to manage or control, or cause or instruct the user to manage or control, the interaction between devices involved with diabetes management, e.g., meter, pump, CGM, and the like. In this way, the user may be instructed to more closely or to manually control interaction between devices such that faults on one device do not propagate and cause errors on downstream devices. Such responsive processing may include reducing the risk threshold of insulin amounts, adjusting a default basal mode, and the like.

Other types of responsive processing will also be understood. For example, a "flag" may be placed on the data to indicate the same is less reliable. For certain data known to be faulty, even if the data is still used, a weight attributed to the data may be lessened. Whatever the type, a benefit and advantage to the responsive processing steps noted are that the same tend to extend the life of the sensor, by allowing the sensor to continue working until a permanent failure is detected. This results in significant cost and convenience advantages to the user. This advantage may be contrasted with prior sensors, that generally have a hard shut off after a predetermined number of days.

The above types of responsive processing are generally where the fault is discriminated from the signal without necessarily considering the clinical context, but where responsive processing is based on the fault and the clinical context information (Regimes I and II). As noted above, however, both fault discrimination and responsive processing may be based on clinical context information, i.e., the signal and clinical context may both be taken into account in discriminating the fault, as well as in determining how to respond to the fault (Regime III).

Particular examples would include combinations of the above. In one particular example, a fault may be discriminated as due to compression based on the clinical context of the time of day, i.e., nighttime. Responsive processing may be based on another clinical context, e.g., the glycemic state. For example, if the user has a high glucose level, the fault may be compensated for by a prediction.

In another example, a fault may be discriminated as an early wound response, i.e., a dip-and-recover fault. The responsive processing may be to ignore calibrations during this time and revert to established factory values, i.e., a priori calibrations. A calibration may be requested and employed as soon as the dip-and-recover artifact is determined to be over.

In yet another example, a water spike or water ingress fault may be discriminated based on data and clinical context. Responsive processing for the same may be via a step of compensation, e.g., by subtracting the "spike" profile when presented with contextual evidence, and further optionally performing additional calibration.

In yet another example, if a short duration noise event fault is encountered, and if the glucose rate of change is known and is low, responsive processing may include using a predictive algorithm to estimate the glucose value during the noise event. Further responsive processing may include providing an indicator of the confidence level of the signal, e.g., numerically, or using colors such as red, yellow, and green, or the like.

Examples

Various specific examples are now provided.

Figure 24:
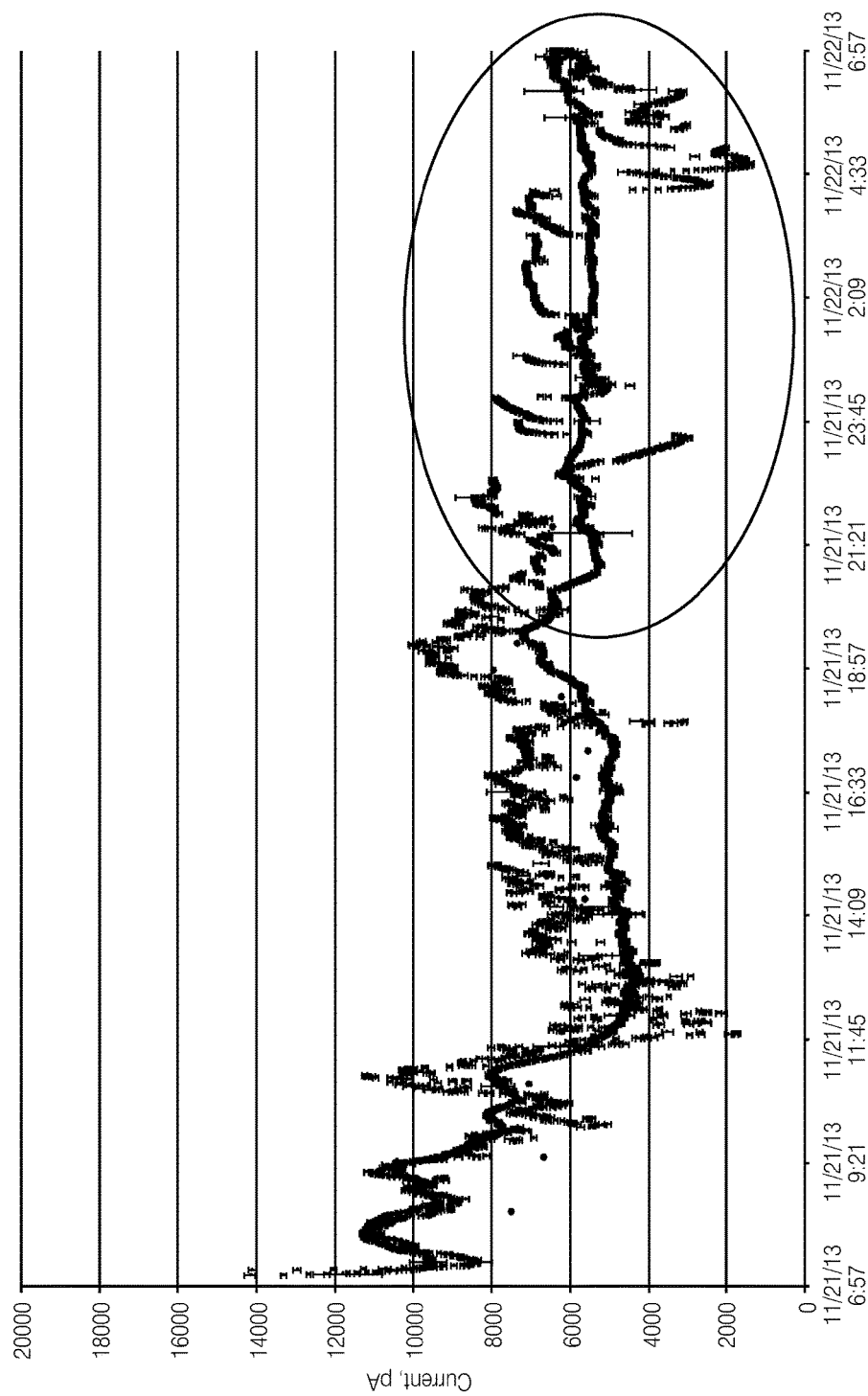
FIG. 24 illustrates a signal exhibiting a compression fault.

FIG. 24 shows an exemplary occurrence of a compression fault. Compression typically occurs over shorter periods of time, e.g., from approximately 20 minutes up to a few hours. In many cases, compression faults also happen when glucose levels are relatively stable, because typically a user is sleeping and not ingesting food or bolusing insulin. Thus, the beginning of a compression episode may be detected based on a drop in glucose, as compared to predicted values or by examining the rate of change. Thus, signal analysis would indicate a drop in potential or counts, and the clinical context would indicate a difference from a normal glucose profile (for a particular host), difference from a predicted value for the host (based on extrapolation from a real time value), or the like. Other clinical context data that may be employed include time of day, e.g., nighttime. Further clinical context data may be that the glucose level was stable prior to the sudden drop.

Responsive processing for the fault, e.g., compensation, may be by prediction, e.g., extending the value of the signal using known or trusted values, e.g., from when glucose was still reliable, up to some period of time, e.g., 40 minutes, so long as the glucose level before the episode was higher than some threshold, e.g., 100 mg/dL, and the previous rate of change was small, e.g., less than 0.5 mg/dL/min If these conditions are not met, then alternative responsive processing may be performed. For example, the display may be blanked and the user woken with the alarm, because if the conditions are not met, the user may potentially be entering a hypoglycemic state.

Other responses to compression will also be understood. For example, the user may be prompted to change body positions so as to remove the compression. However, if the clinical context indicates that the time of day is night, such prompting may be suspended and responsive processing limited to actions in a closed loop mode (unless requiring user intervention or alerting). In certain other clinical contexts, the responsive processing may be to do nothing, in particular if the responsive processing would add little of value. For example, warning a user when a nighttime compression episode is detected may provide no additional insight to the user, if their current reading is 180 mg/dL (indicating that the true glucose is above that value). This reading indicates an elevated glucose value, so the clinical response would be the same, e.g., compensation. Put another way, just because a fault is detected does not mean that the responsive processing is always an affirmative action with respect to the fault—the responsive processing may mean to perform no actions or steps.

As another example, the user's actual glucose level may be 87 mg/dL, and the CGM may read 77 mg/dL. The fault discrimination algorithm may properly detect a compression event based on the signal data and clinical context. The fault discrimination algorithm may quantify the fault as a −25 mg/dL bias, but in this example the true compression bias is actually 10 mg/dL. If the responsive processing is to compensate for the detected fault, then 25 mg/dL would be added to the CGM reading, resulting in a reading of 102 mg/dL. The alternative is to leave the CGM with the negative bias. In this case, leaving the CGM with a negative bias is the safer or more conservative approach, and thus the fault discrimination algorithm may choose to not perform the step of compensation in the circumstance based on the user's glycemic state (e.g., below a predetermined glucose threshold).

With regard to compression, generally multiple inputs feed into the unambiguous determination of a particular fault. As described above with respect to sensor end of life ("EOL") determination, methodologies may be employed to unambiguously determine such faults, or to determine such with a desired degree of probability. The multiple inputs may constitute risk factors, and the risk factors can be evaluated periodically or intermittently, e.g., with the receipt of sensor data, or otherwise. The risk factors can be iteratively determined, averaged, or trended over time and the results used in later processing.

Suitable risk factors for compression may include sensor reading, sensor variability, time of day, pattern data, as well as various others. In some embodiments, the processor module is configured to evaluate the various risk factors to provide compression risk factor values, which may include simple binary (yes/no) indicators, likelihood or probability scores (e.g., relatively scaled or percentages) and/or actual numbers (e.g., outputs of the various tests). As with EOL risk factors, the processor module may be configured to run probability functions to determine a probability of compression and/or a likelihood of recovery for one or more of the plurality of compression risk factors. In some embodiments, risk factors are mapped to a score (e.g., from 0 to 1) based on one or more parameters, which then in turn may be mapped by functions, which translate a particular risk factor or set of risk factors to a compression risk factor value, indicating for example, a possibility of the sensor to recover from a particular risk factor from compression. Other methods of translating risk factor outputs may be used as is appreciated by a skilled artisan, such as by using one or more criteria, algorithms, functions or equations. In other implementations, fuzzy logic may be employed in the determination of a probability of a compression fault, as may decision fusion, both of which are described elsewhere. Look up tables, expert rules, neural nets, and the like may also be employed in the determination according to implementation.

In the above example multiple alternatives were seen for responsive processing. For certain faults, there may be only one alternative. For example, if the fault is dip-and-recover or oxygen noise, the display may be blanked regardless of other contextual information or specific characteristics of the data.

Figure 25:
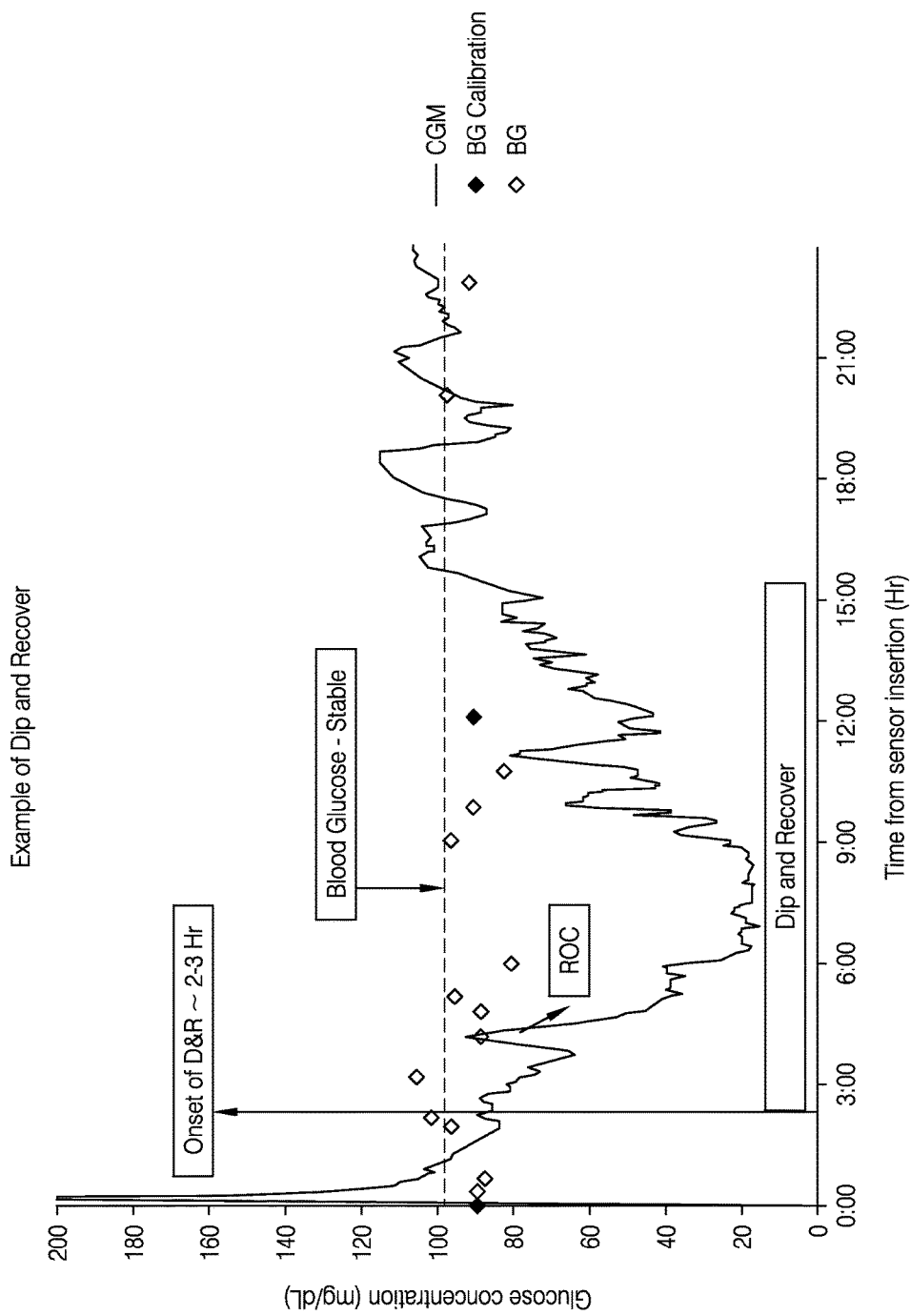
FIG. 25 illustrates a signal exhibiting a "dip-and-recover" fault.

FIG. 25 depicts the case of an early wound response, e.g., "a dip-and-recover" fault. Such faults tend to appear in many ways like low glucose levels, and it is sometimes difficult to discriminate the same by just reviewing the uncalibrated data without consideration of the clinical context.

Figure 26:
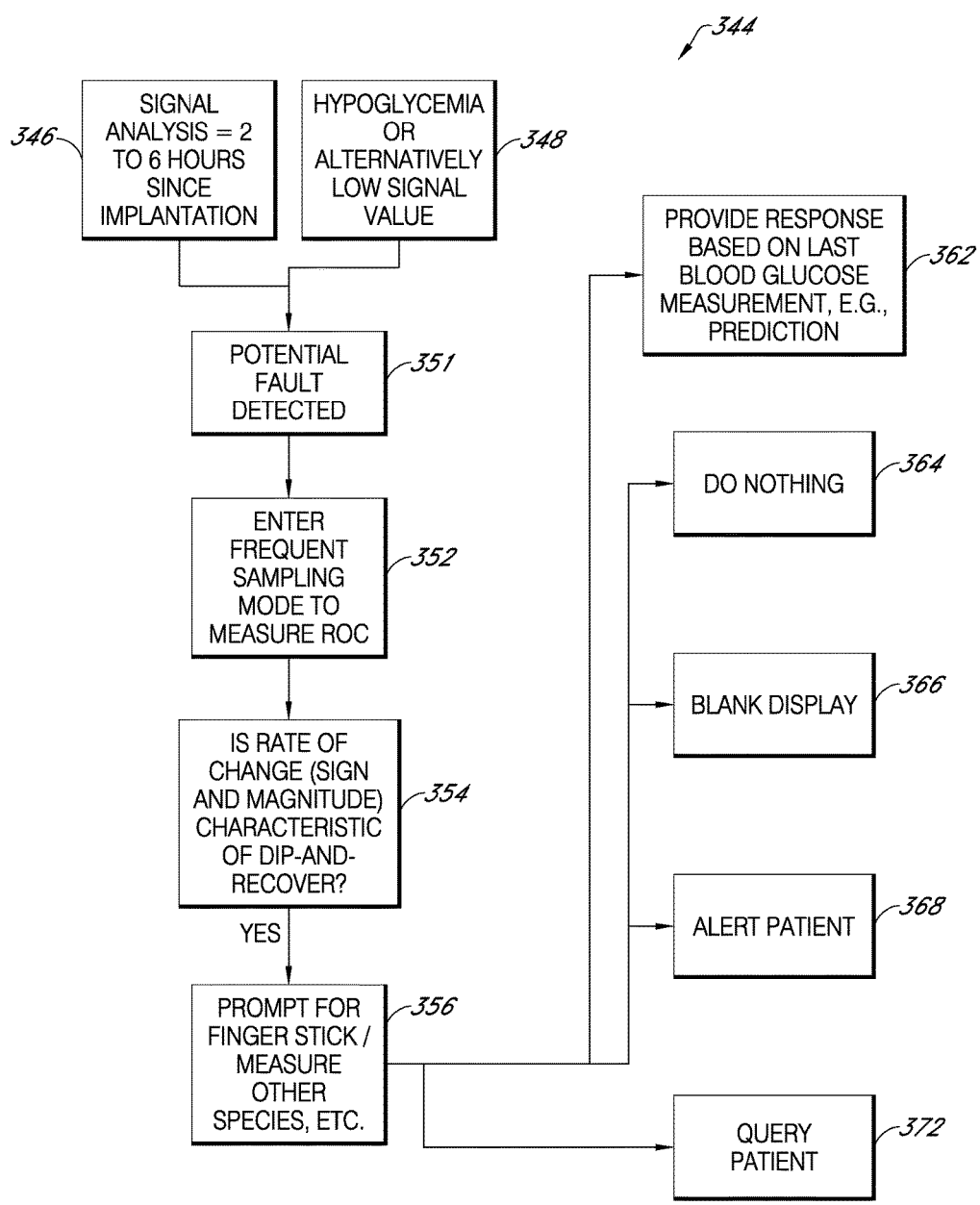
FIG. 26 is a flowchart of another exemplary method according to present principles.

As noted above, dip-and-recover faults are characteristic of recently implanted sensors due to physiological early wound responses. Thus, in one exemplary implementation, and referring to the flowchart 344 of FIG. 26, the time since implant may be used as a signal analysis criterion in fault discrimination. For example, if signal analysis indicates that the time since implant is between, e.g., two and six hours (step 346), and if the clinical context is determined to be that a hypoglycemic state is entered (step 348), then a potential fault may be detected (step 351).

To discriminate the fault, one type of responsive processing is to enter a frequent sampling mode (step 352), e.g., every 30 seconds, in order to ascertain the rate of change of the glucose level. If the rate of change is characteristic of a dip-and-recover fault (step 354), e.g., the sign is negative and the magnitude is greater than a threshold, then various types of responsive processing may take place. For example, the user could be prompted to measure their blood glucose level manually, e.g., via a finger stick (step 356). Alternatively, where an appropriate sensor has been provided, another different chemical species, e.g., NO, may be measured that may be released by inflammatory cells that are believed to be caused by the dip-and-recover fault, e.g., because the same may consume the glucose. In some cases, both steps may be performed. In this way, the fault would be discriminated both on the data and/or on the clinical context.

If the fault is discriminated as due to dip-and-recover, then responsive processing may occur. The responsive processing may take a number of forms, including compensating for the fault by depending on the patient's last blood glucose entry (step 362) for a prediction or forecasting. In some cases, if the underlying signal is not representative of the glucose concentration and if predictive algorithms are not usable, e.g., because of minimal data, then the compensation step may be skipped and no action performed (step 364).

Other types of responsive processing will also be understood. For example, if the blood glucose was previously measured in a hyperglycemic range, than the display screen of the monitor device may be blanked (step 366), so as to not convey a potentially erroneous reading. As the patient started in a hyperglycemic state, but the rate of change indicated a decrease in glucose value, such may not immediately present a dangerous situation. Of course, the length of time for which the display screen is blanked may vary depending on the clinical context, e.g., level of the hyperglycemia, magnitude of negative rate of change, and the like.

On the other hand, if the patient started off euglycemic or hypoglycemic, then the patient may be alerted (step 368). In this case, just in case the rate of change is reflecting the actual glucose value, and is not caused by a dip-and-recover fault, then the alert may be thrown to warn the patient of a potential impending hypoglycemic state. As with the hyperglycemic state, the actual steps taken may depend on other aspects of the clinical context.

Certain implementations may call for querying the patient (step 372), in order to obtain additional information about the clinical context. For example, the patient may be queried as to whether they ingested a meal in the last few hours, and/or recently administered insulin. If no patient response ensues, an alarm may be sounded.

Other variations include providing modifiers to the displayed glucose value, e.g., a range of glucose values, to indicate potential clinical values due to the uncertainty caused by the fault. Historical data may also be employed, e.g., based on the time of day and other clinical contexts, to calculate a range or to inform other responsive processing.

As with compression faults and EOL determination, dip and recover faults also generally involve feeding multiple inputs into their determination. And as above, methodologies may be employed to unambiguously determine such faults, or to determine such with a desired degree of probability, including the consideration of multiple risk factors evaluated periodically or intermittently.

Suitable risk factors for dip and recover may include sensor reading, time since implant, pattern data, as well as various others. In some embodiments, the processor module is configured to evaluate the various risk factors to provide dip and recover risk factor values, which may include simple binary (yes/no) indicators, likelihood or probability scores (e.g., relatively scaled or percentages) and/or actual numbers (e.g., outputs of the various tests). As with EOL risk factors, probability functions may be run by the processor module to determine a probability of dip and recover and/or a likelihood of recovery for one or more of the plurality of risk factors. Other methods of translating risk factor outputs may be used as is appreciated by a skilled artisan, such as by using one or more criteria, algorithms, functions or equations. In other implementations, fuzzy logic may be employed in the determination of a probability of a dip and recover fault, as may decision fusion, both of which are described elsewhere. Look up tables, expert rules, neural nets, and the like may also be employed in the determination according to implementation.

Figure 27:
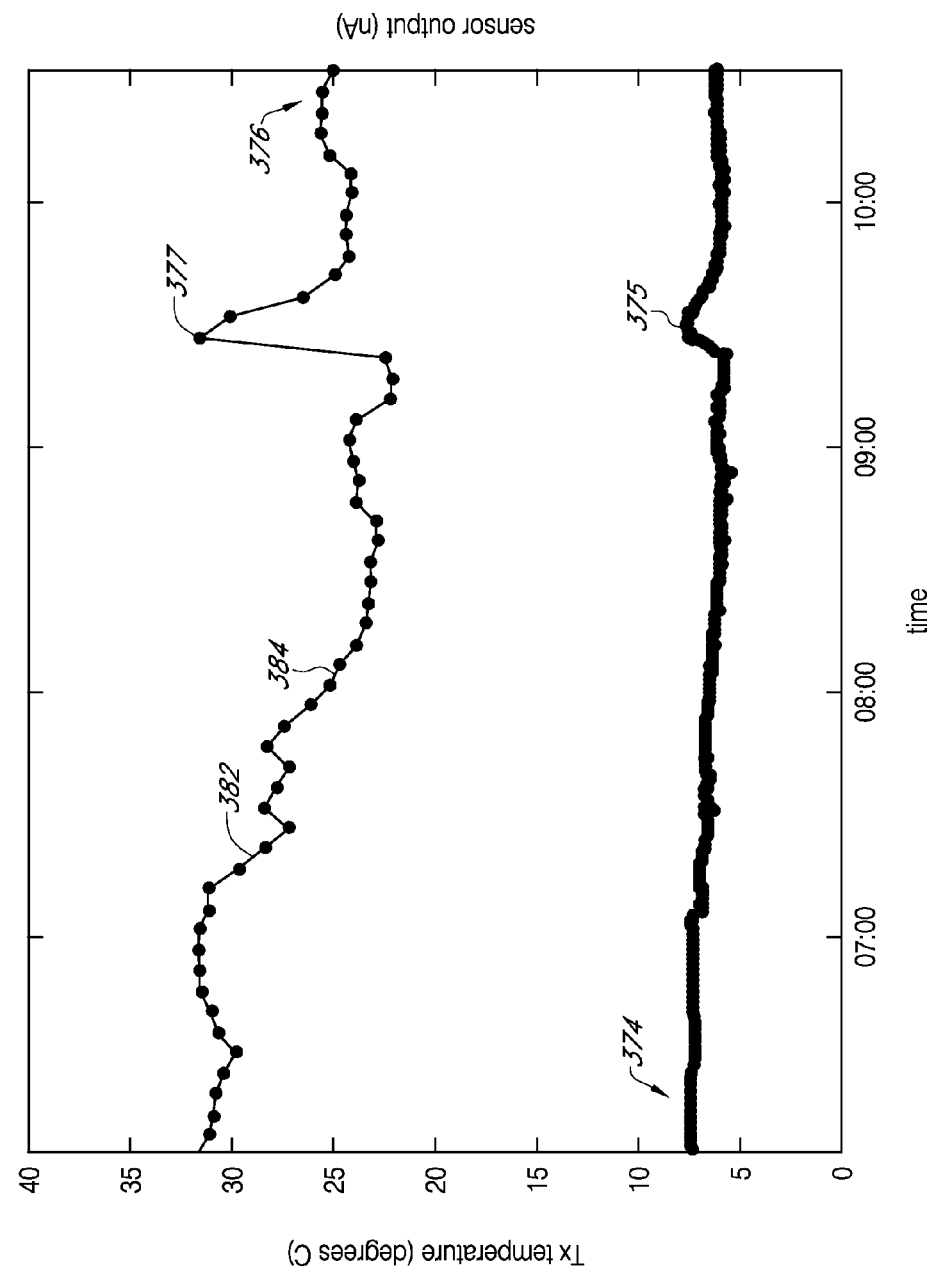
FIG. 27 illustrates a signal exhibiting a "shower spike"

FIG. 27 illustrates fault discrimination of a "shower spike" based on signal analysis including temperature data and time of day criteria, which when combined provide clinical context information indicative of a patient showering. In particular, in a signal analysis step, the sensor signal output 374 indicates a rise in signal at point 375, which correlates with a rise in temperature at point 377 in the temperature plot 376. In analysis of the clinical context information, the time of day of the spike is consistent with the time of a user's shower, either in comparison to other users or based on pattern data for this particular user. Other clinical context information may be seen, e.g., a drop in temperature, at portions 382 and 384, prior to the spike at point 377, which may indicate the patient has gotten out of bed.

To further discriminate this fault, having identified a potential fault based on signal analysis and clinical context, testing may be performed to look for "short circuited" electrodes. For example, a self-diagnostic mode may be entered and the bias potential changed. The system may then look for an absence of a response (short-circuits may generally be seen to be nonresponsive to a various given stimuli).

For example, in one implementation, systems and methods according to present principles may provide a method of discriminating a fault, including a step of identifying a potential fault based on signal analysis and data about clinical context. Other steps may include entering a self diagnostics mode and performing various tasks, e.g., changing the bias potential and examining a response. For example, the absence of a response may indicate a "short circuit", as the same may generally be seen to be nonresponsive to a various given stimuli.

As with EOL, compression, and dip and recover faults, suitable and multiple risk factor inputs may be employed in the determination of a shower spike fault, using statistical and probabilistic models, including fuzzy logic and decision fusion analyses, as well as using lookup tables or the like in the determination.

Figure 28:
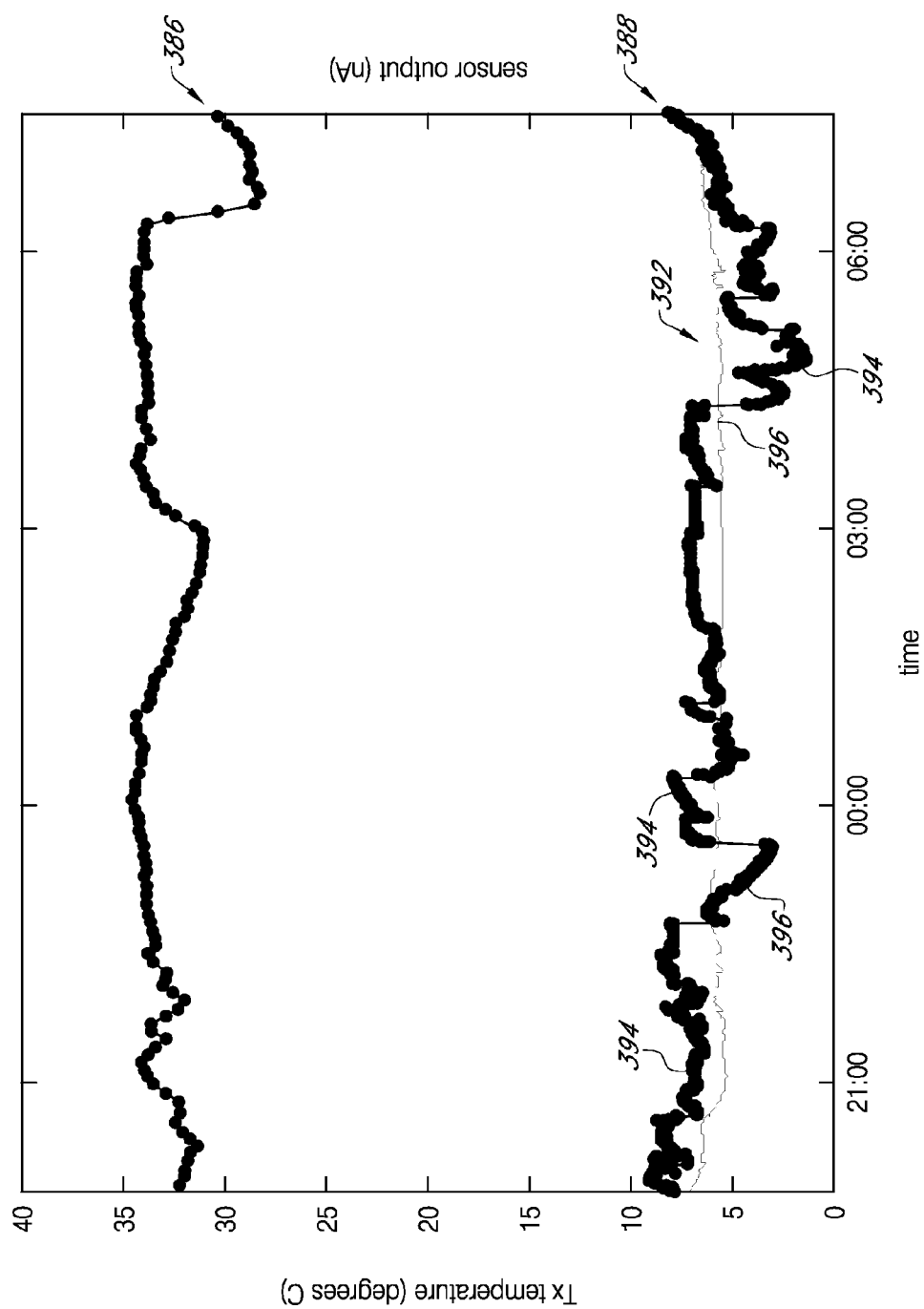
FIG. 28 illustrates another signal exhibiting a compression fault.

FIG. 28 illustrates another example of fault discrimination of a compression fault. Trace 386 corresponds to temperature, and traces 388 and 392 correspond to unscaled paired sensor traces. The signal analysis characteristics based on the traces include low levels of high-frequency noise 394, as well as abrupt shifts 396 in sensor signal at the beginning and end of compression events. These shifts are illustrated in the sensor trace 388. The paired sensor trace 392 represents a similar type of sensor, worn on the other side of the patient, and thus not subject to compression. The trace 392 accordingly shows a reliable glucose signal compared to the trace 388 having significant artifacts. Clinical context information indicates a sleeping user, which may be determined by the time of day compared to certain criteria for sleeping. Other clinical context information includes elevated temperatures, as well as a lack of meter values (not shown), indicating the patient has not recently taken a finger stick.

In one implementation of a method for fault discrimination of a compression fault, a signal is received and analyzed for various aspects. For example, the received signal may be analyzed for low levels of high-frequency noise. As another example, the received signal may be analyzed for shifts in sensor signal, greater than a predetermined threshold, at the beginning and end of a significant or sustained decrease in sensor signal, e.g., one characterized by a steep decline in signal value, followed by a period of sustained decreased value, followed by a steep increase in the signal value. The method for fault discrimination may further include analysis of clinical context data compared to clinical context criteria in order to determine clinical context information. For example, the received clinical context data may include an elevated temperature compared to that which may be expected in the absence of the fault, the time of day, e.g., if it is expected time for sleeping, as well as other such data. If two sensors are worn, the received signals may be analyzed for situations where once sensor sees a decrease in signal value and the other does not. According to the above noted signal analysis and the clinical context information, the system and method may discriminate that a compression fault has occurred.

Figure 29A:
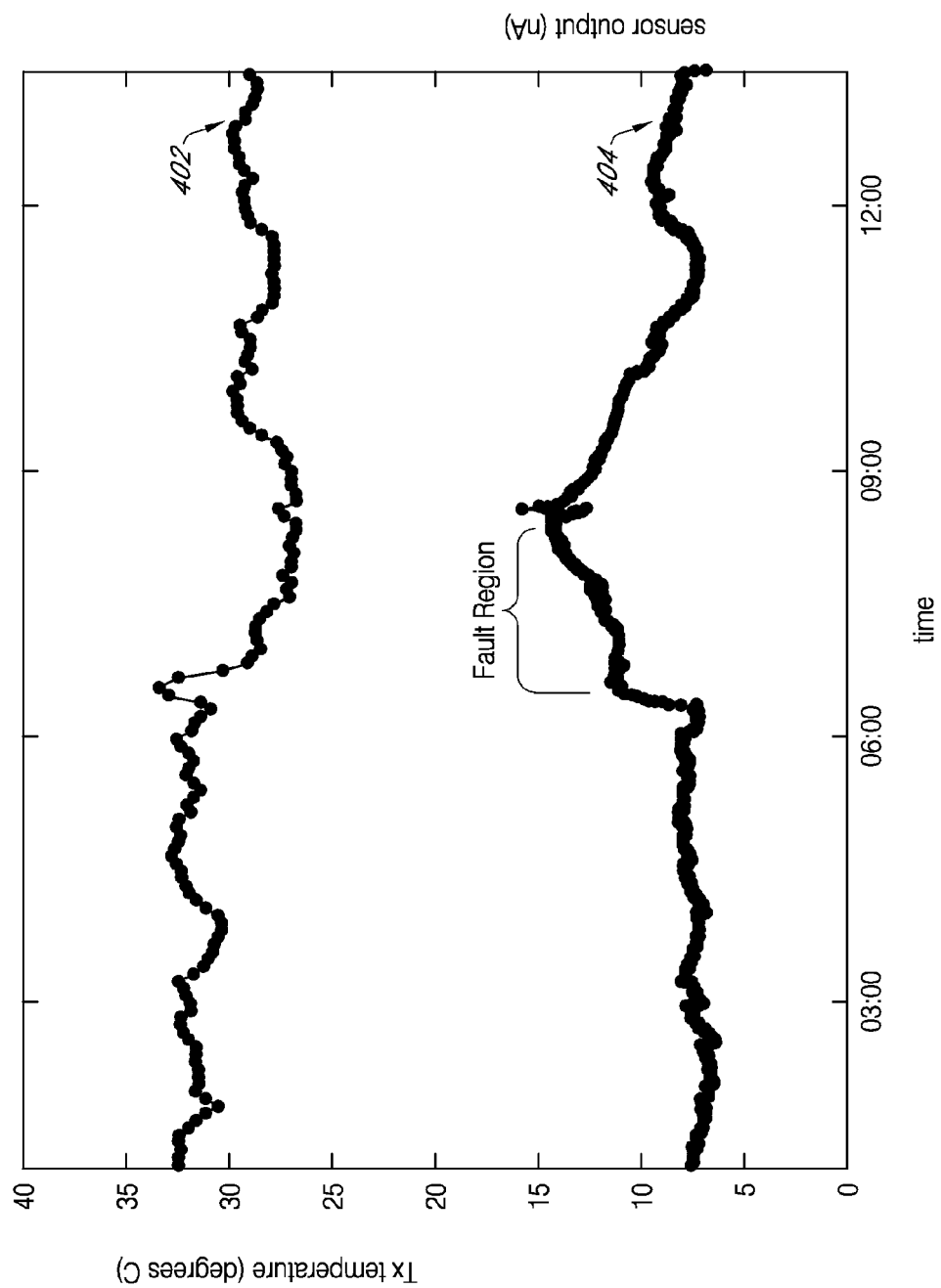
FIGS. 29A-29B illustrate signals exhibiting a water ingress fault.
Figure 29B:
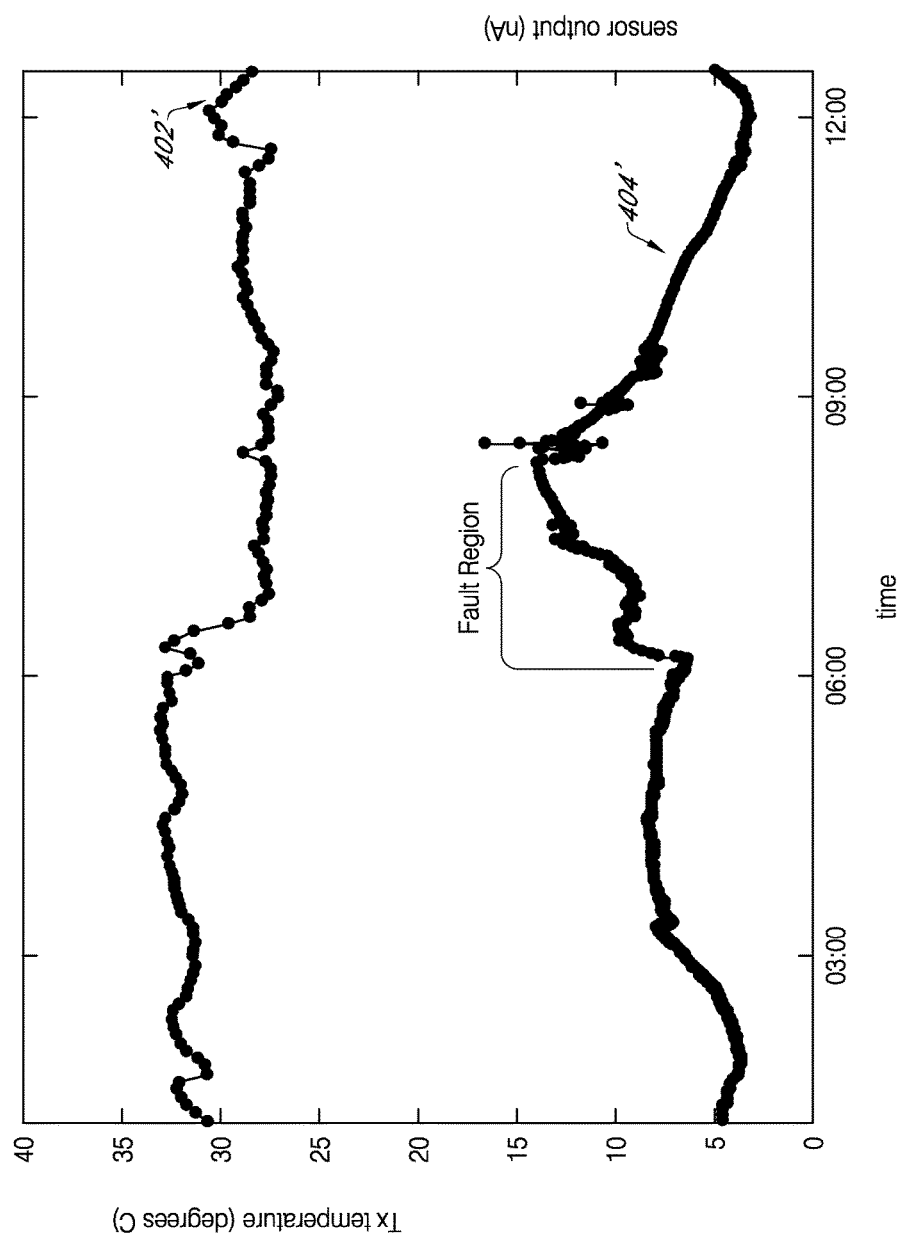

FIGS. 29A and 29B illustrate another example of fault discrimination, with the fault again being water ingress. These figures represent the same patient on different days. Traces 402 and 402' indicate temperature readings, and traces 404 and 404' indicate sensor readings.

The clinical context information may be determined in a number of ways, e.g., by comparing the temperature against the clinical context criteria of an expected temperature, by comparing the time of day (or another scale, e.g., time of week), against clinical context criteria, or the like, and in this way determining behavior patterns, e.g., showering. Such patterns may be seen to be highly consistent on weekdays, and thus the clinical context information in this example indicates a showering user. More particularly, the clinical context criteria indicates a regular time of day at which the signal experiences an abrupt increase (see the noted fault region), followed by a decay over a multiple hour period. Other data which may be compared to clinical context criteria to determine clinical context information includes temperature, e.g., a decrease in temperature, likely caused by the user rising from bed, as well as noise, e.g., a noise level in preceding data, such as may be caused by water ingress caused by a shower.

Figure 30:
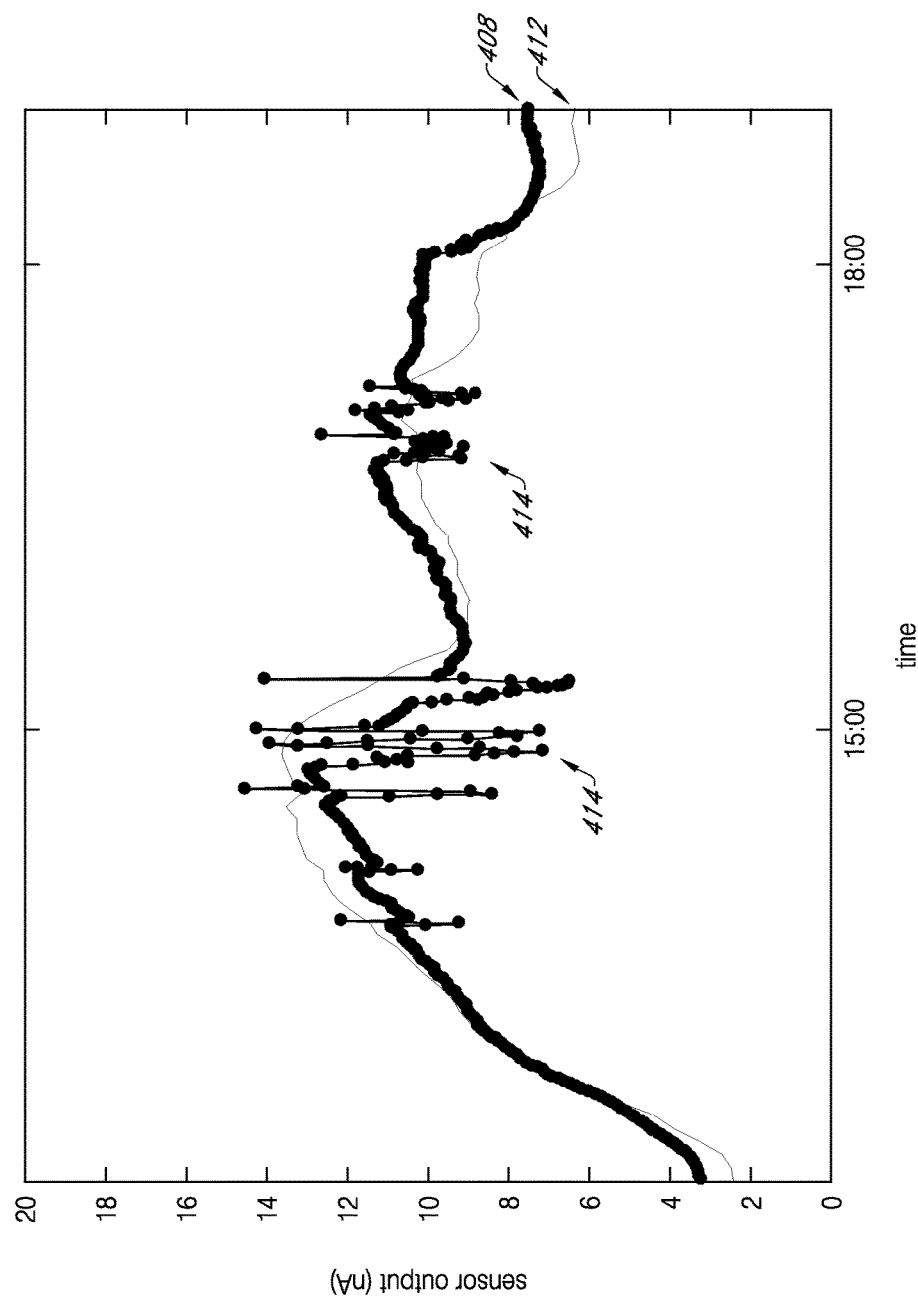
FIG. 30 illustrates a signal exhibiting end-of-life noise.

In this case, temperature compensation would be insufficient to compensate for the shower spike. In particular, while some prior efforts at performing temperature compensation have used measurements of temperature in vivo, at the sensor site, and ex vivo, on the transmitter, in the case of water ingress the problem is not caused by an incorrect or inapplicable temperature reading at the sensor; rather, the same is caused by a short circuit 29 to water ingress into the transmitter. In fact, the 27 of the temperature sensor in FIG. 30 is opposite to that of the temperature sensor in FIG. 28, though both are caused by water ingress. Thus, providing a level of temperature compensation without further signal analysis and clinical context, e.g., by adding a constant value, can lead to significant errors. Accordingly, temperature used as an input here should be understood to be applied in the context of comparing temperature data to predetermined clinical context criteria to determine clinical context information (e.g., whether a user is sleeping, showering, or the like).

In more detail, water ingress faults cause moisture to enter the seal or enter cracks in the insulator, in either case instigating additional signals that are not related to glucose, though the signals still emanate from an electrochemical mechanism (though different from that of glucose). The signal from the non-glucose related mechanism is a function of various factors, including the additional exposed surface area of the sensor, the reaction with the non-glucose analyte, and the exposure of different working electrodes to moisture. During amperometric detection, the signals from both sources look similar and are difficult to distinguish. However, in some cases a unique signature can be obtained from an actual electrochemical reaction with the analyte. The electrochemical signal coming from exposure of additional surface area also differs from that of other interferants, e.g., acetaminophen.

Thus, in one implementation, electrochemical means can be used to obtain a quantitative measure of the surface area using multiple potentials or AC voltammetry or pulsed voltammetry, thus giving another indication of water ingress.

For example, AC voltammetry may be intermittently performed to share the function of the working electrode, e.g., glucose detection may occur for four minutes out of a five-minute cycle, while for the last-minute, an oscillating potential can be applied to the electrodes to see if any of the signals are from nonglucose related signals, or those related (or not) to hydrogen peroxide or other potentially interfering analytes. Distinguishing or separating interfering analytes from each other is not necessary, just distinguishing moisture ingress signals from other signals is generally required in fault discrimination of this type. The above signal apportionment is just an example. In general, this method uses a portion of the measurement cycle for error checking in to see if there is any other unexpected electroactive surface area exposure. Other techniques that may be employed for such include oscillating potentials, impedance measurements, pulsed amperometric detection, and the like.

For example, in one implementation, systems and methods according to present principles may be employed to measure or discriminate a water ingress fault by use of the following steps. In a first step, a signal is received, the signal pertaining to an electrochemical mechanism caused by an analyte and a sensor. In a next step, a quantitative measure of the surface area is determined, e.g., from the signal or from alternate electrochemical means, e.g., multiple potentials, AC voltammetry, pulsed voltammetry, or the like. The quantitative measure of the surface area is then employed to determine if water ingress has occurred to see, e.g., if a portion of the surface area of the sensor is deleteriously taken up by moisture. In some cases, additional steps may be performed, such as detecting a signature is detected from the signal, the signature associated with an interferant and/or with a level of surface area of the sensor.

FIG. 30 illustrates an example of signals in which the fault of "end-of-life noise" can be discriminated on sensors worn simultaneously on a patient. The units for the sensor output, upon scaling, are current [nano-amps]/clinical glucose value [mg/dL] or nano-A/mg/dL. Traces 408 and 412 are shown, where trace 408 is the sensor trace illustrating the fault. The trace 412 illustrates a reliable signal, while the trace 408 has been rendered unreliable because of the fault. As noise can be site specific, e.g., influenced by the wounding of the particular microenvironment, it is not surprising to see a site-specific fault occur in one location on the patient but not another location on the patient worn over the same time period.

Certain characteristic shapes 414 for trace 408 can be seen and used to discriminate the fault, including an abrupt downward spike at the beginning of a noise episode, high-frequency noise present throughout the episode, and a positive overshoot at the end of the noise episode. Signal analysis may also show other potential signal criteria, including that noise episodes tend to be proximate in time to similar episodes, and the tendency for the episodes to become more frequent as time goes on and the sensor endures more wear. Another signal-related predetermined criterion which may be used to discriminate this type of fault is that the fault generally coincides with a gradual decrease in sensitivity. One type of clinical context information for this fault includes that the fault more frequently occurs when glucose is elevated. Another type of clinical context information criterion is that there is an increased probability of occurrence of the fault if there exists a high average sensor current during the session, or a high integrated current from the start of the session. Other exemplary parameters that may be employed in end-of-life detection include amplitude and/or variability of sensitivity, e.g., generally indicating a decline of 5%, 10%, 20%, over the last 6, 8, 10, 12, 24 hours, as well as noise patterns, spectral content, days since implant, oxygen concentration, a glucose value, an error in glucose value at calibration, or the like.

In a particular implementation of systems and methods according to present principles, in particular applied to the discrimination of the fault of end-of-life noise, steps may include receiving a signal trace in analyzing the signal trace for certain characteristic shapes. For example, the signal trace may be analyzed to detect an abrupt downward spike at the beginning of a noise episode, high-frequency noise present during the noise episode, and a positive overshoot at the end of the noise episode. If such is seen, at least an initial determination or discrimination of end-of-life noise may be made. Other aspects may contribute to such a determination or discrimination. For example, if multiple such signal traces are seen, especially over a predetermined time window, where each signal trace includes the above aspects, the likelihood or probability of end of life noise may be increased, and the confidence level of such a determination or discrimination may be caused to rise. If such episodes become more frequent as time goes on, again the likelihood or probability of end of life noise may be increased, and the confidence level of such a determination or discrimination may be caused to rise. In the same way, if additional data is detected about the sensitivity of the sensor, and if the sensitivity is seen to decrease over time, particularly in a gradual way, then again the likelihood or probability of end of life noise may be increased, and the confidence level of such a determination or discrimination may be caused to rise.

Clinical context information may also cause the likelihood or probability of end of life noise to be increased, and thus so too the confidence level of such a determination or discrimination. For example, if the glucose value has been elevated for a long period of time, such may tend the increase the likelihood or confidence of the determination of an end-of-life fault. Other types of clinical context information that serve as an input into the determination or discrimination of an end-of-life fault include: time since implant, oxygen concentration, glucose values, errors at calibration, or the like.

Figure 31:
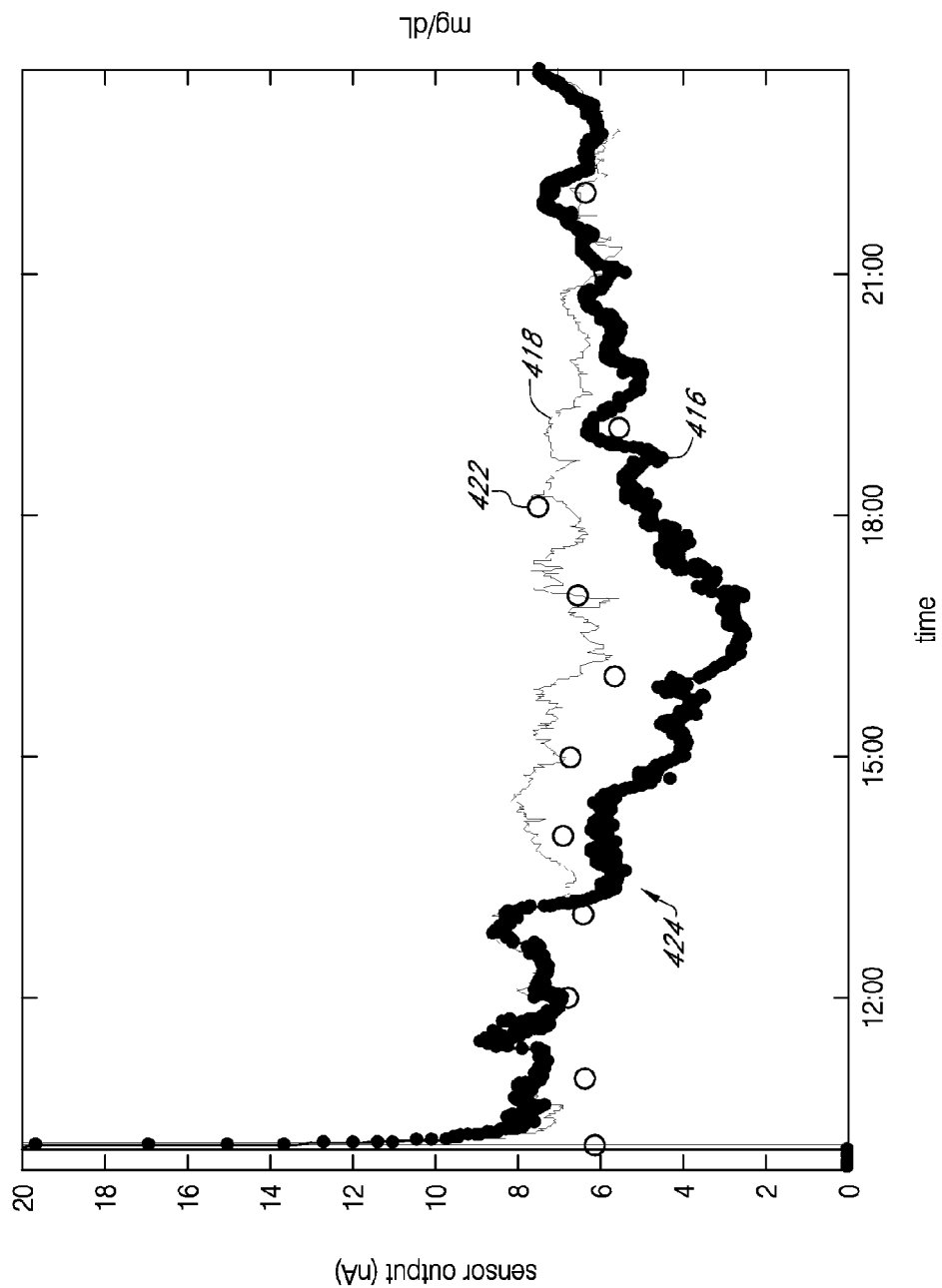
FIG. 31 illustrates another signal exhibiting a dip-and-recover fault.

FIG. 31 illustrates another example of a dip-and-recover fault. In this example, the user wore two sensors simultaneously, both of which showed some artifact, but one which showed a more severe fault, caused by a dip and recover fault. In particular, the trace 416 is a sensor trace showing a dip and recover fault, while trace 418 only shows artifacts related to noise. The circles 422 represent meter values.

As may be seen at point 424, one signal characteristic indicative of a dip-and-recover fault includes a signal drop that is inconsistent with the meter values 422. Another potential signal characteristic is an increase in noise in a specific frequency range (seen in both traces 416 and 418), or in noise that does not correlate with paired redundant sensor (note lack of correlation between 416 and 418 during dip and recover). The level of noise in a specific frequency range can be determined by an appropriate frequency transform. A further potential signal characteristic consistent with a dip-and-recover fault is a downward deviation of the signal from the redundant sensor data, which is also show in FIG. 31 by the deviation between trace 418 and trace 416. One type of clinical context information that may be employed in fault discrimination or responsive processing includes time since implantation, as the onset of this type of fault generally occurs several hours after sensor insertion.

Accordingly, in one implementation, systems and methods according to present principles are directed to ways to discriminate dip and recover faults. A first step in an exemplary method is to receive a signal and to analyze the received signal. Various characteristics can be employed in the analysis to determine if the received signal is consistent with a dip and recover fault. For example, if the received signal decreases at the same time as blood glucose meter values do not decrease, a determination or discrimination of a dip and recover fault may be made. Alternatively, if an increase in noise in a specific frequency range is seen, such may also lead to a determination or discrimination of a dip and recover fault. If the sensor is paired, i.e., a user is wearing two sensors, noise in one but not in the other, or a signal decrease in one but not in the other, may further lead to a determination or discrimination of a dip and recover fault. In the method of a determination or discrimination of a dip and recover fault, clinical context information may also be employed. For example, clinical context data may be received by systems or methods according to current principles, where the clinical context data constitutes time since implantation, and the same may be compared against criteria, e.g., wherein the criteria includes if the time since implantation is before or after a predetermined threshold amount of time from implantation, e.g., 12 hours. If the signal information shows a decrease compared to a blood glucose meter values, or exhibits an increase in noise in a specific frequency range, or meets one of the other criteria noted above, and the time since implantation is less than the predetermined threshold, then the determination or discrimination may indicate the occurrence of a dip and recover fault.

Figure 32:
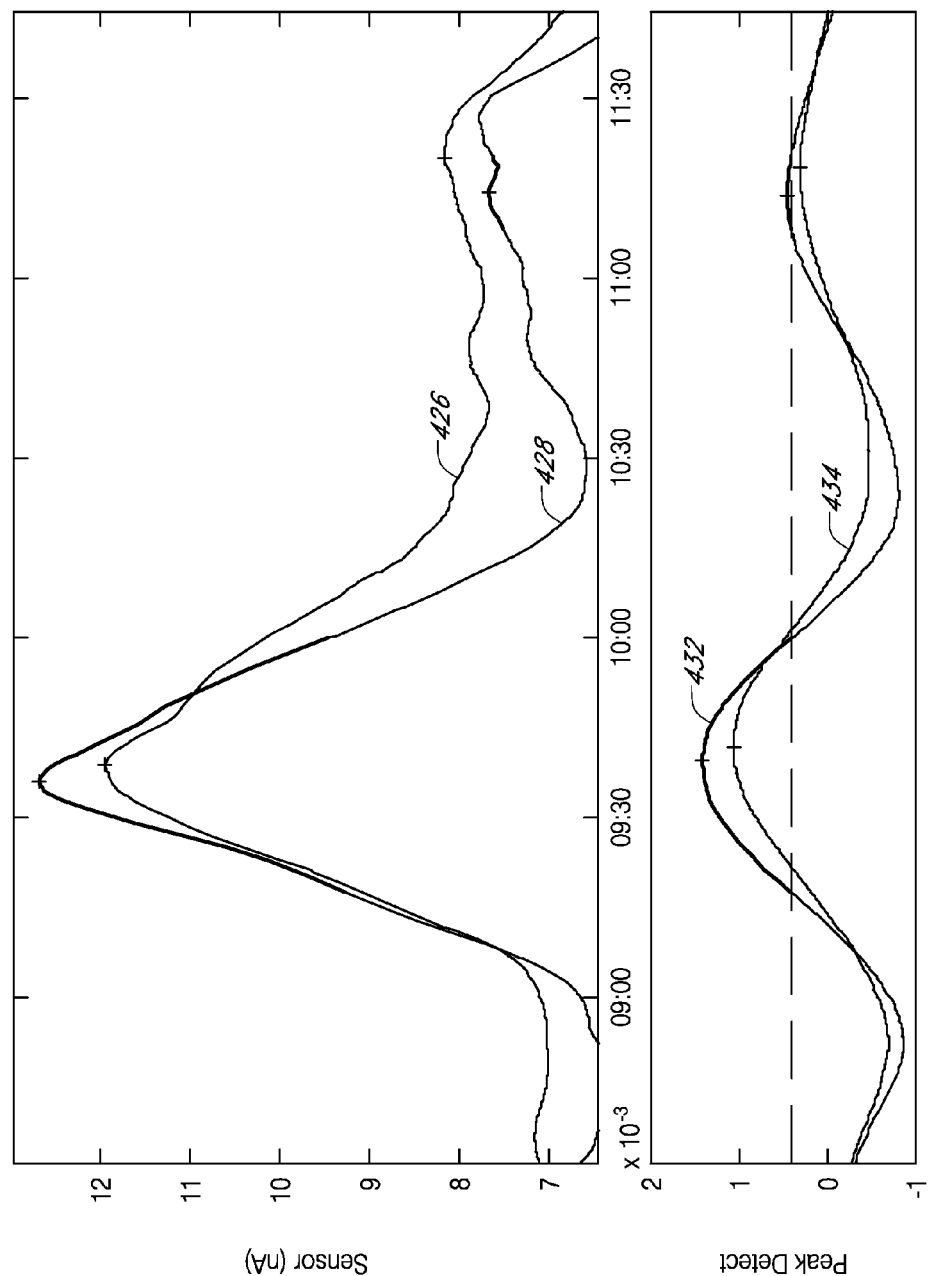
FIG. 32 illustrates signals in which a lag error is present.

FIG. 32 illustrates another type of fault, i.e., lag. Results are shown for two different sensors implanted in a host simultaneously, illustrated by traces 428 and 432, with corresponding peak detected curves 432 and 434, respectively. Once sensor (traces 426 and 434) experienced a few minutes of lag compared to the other. Such lag errors may be important in the context of falling glucose after a meal, with the risk being that a low glucose alarm might be delayed or missed. This phenomenon might be a permanent characteristic of the sensor site or it may be transient, depending on local blood perfusion. In any case, responsive processing may be performed, and in particular the use of a predicted or forecasted value, based on glucose concentration and/or rate of change. In this way the effect of the time lag may be mitigated, so that the same does not cause the user to delay responding to a hypoglycemic event.

In a particular implementation of systems and methods according to present principles, the same may be employed for the discrimination of such lag faults. A first step is to receive the signal from a monitor, e.g., a CGM or other analyte monitor. A next step is to analyze the signal for the presence of lag. The analysis for lag may include analyzing the received data signal itself or analyzing the received signal along with another received signal, e.g., one from a paired glucose sensor. Once the fault of lag is determined or discriminated, responsive processing may be performed. For example, for lags greater than a predetermined threshold, or indeed for any lags, a predicted or forecasted value may be displayed to the user instead of the lagged value, to provide a more accurate indication to the user of their current situation.

Figure 33A:
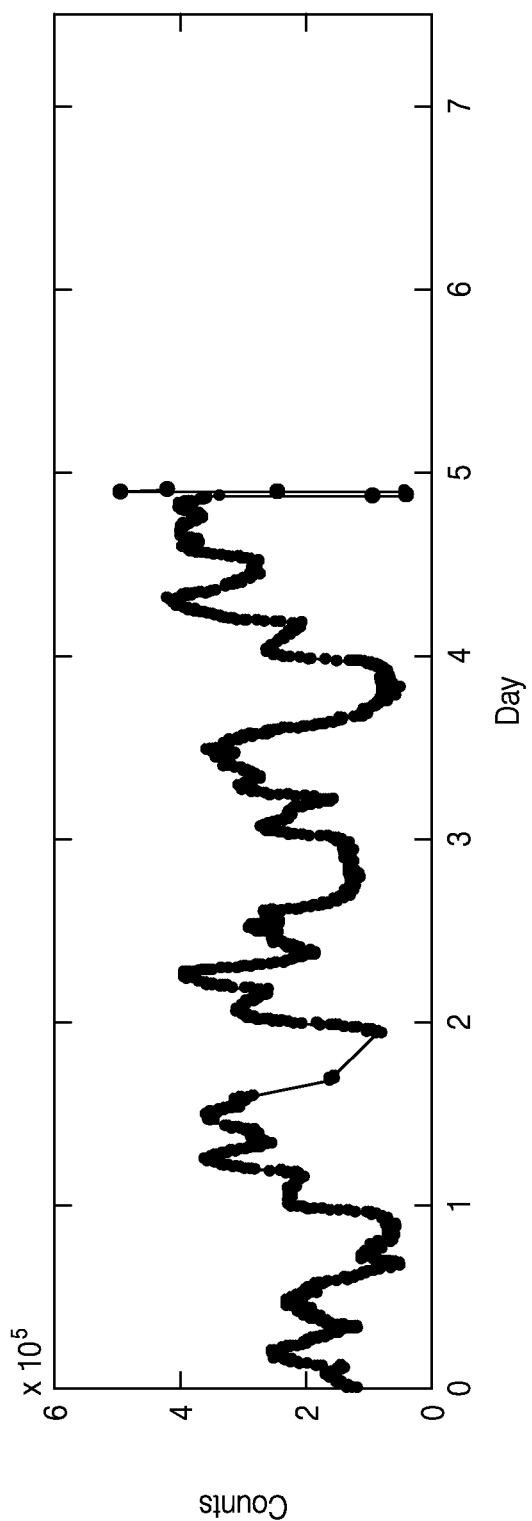
FIGS. 33A-33D illustrate another signal exhibiting a compression fault.
Figure 33B:
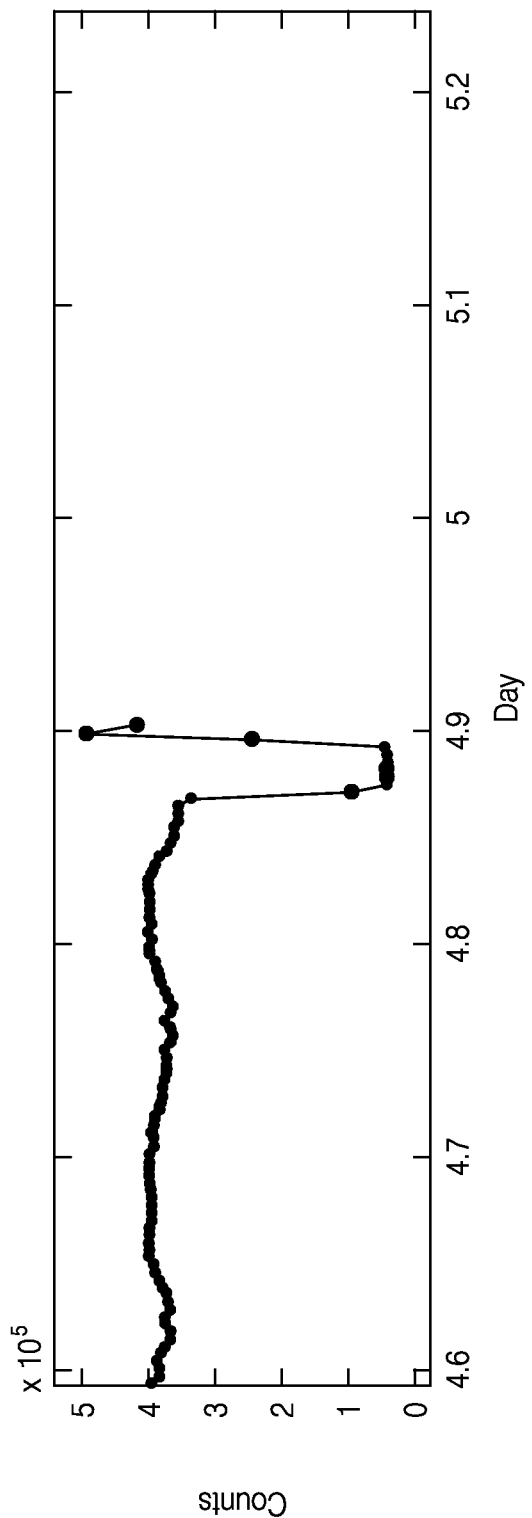
Figure 33C:
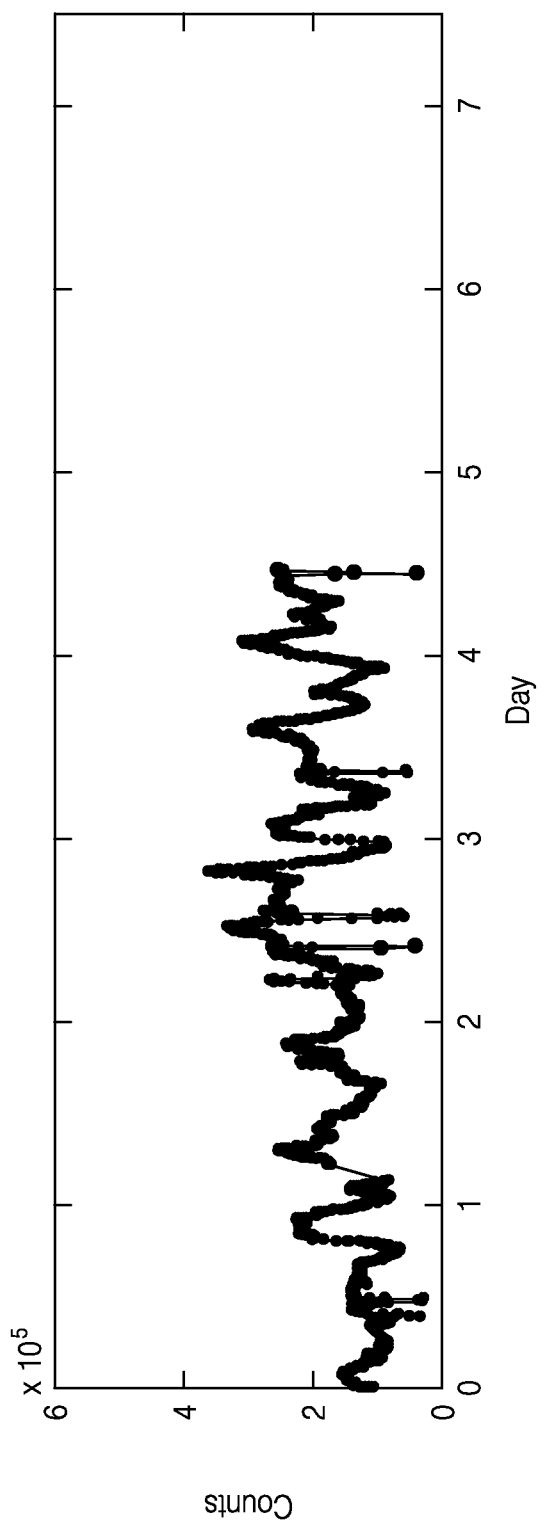
Figure 33D:
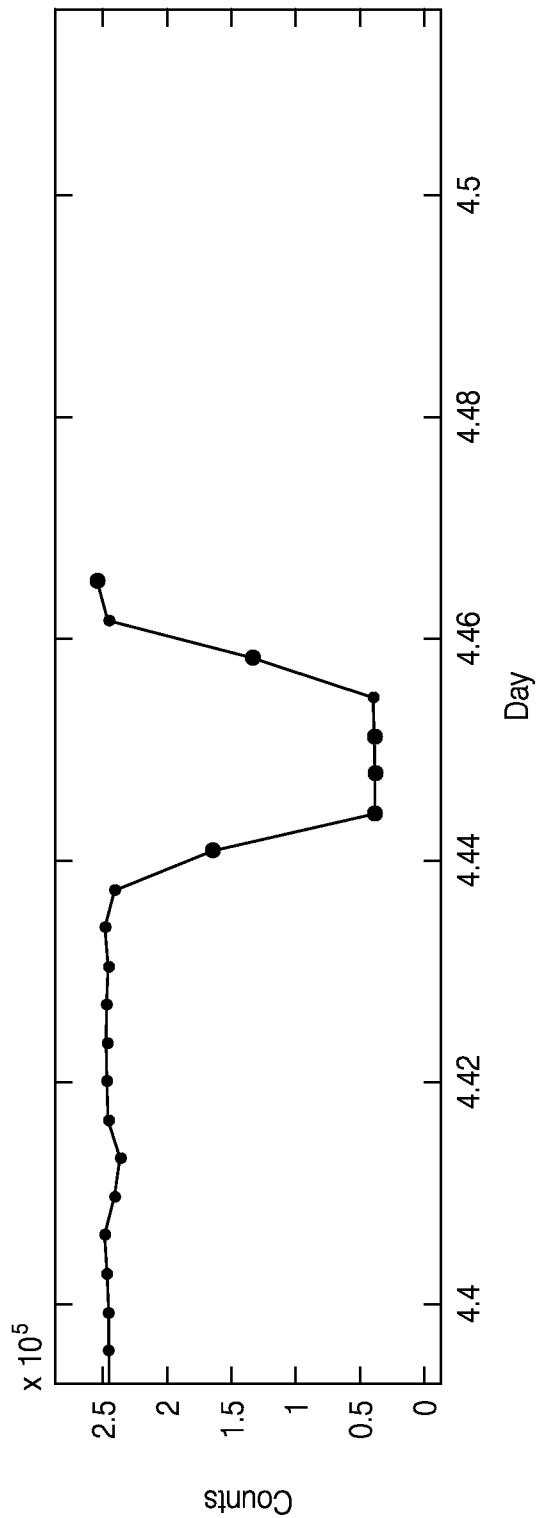

FIGS. 33A-33D illustrate another example of the fault of compression, in this case as evidenced in pediatric patients. A raw signal is shown, measuring counts, where generally 200,000 counts corresponds to a clinical glucose value of 100 mg/dL. FIGS. 33A and 33C show multi-day data for two different patients, while FIGS. 33B and 33D illustrate more detailed views of a particular compression episode within each of FIGS. 33A and 33C, respectively. As may be seen, the sensor signal drops completely to a baseline value during these compression faults. In these cases, the sensor was worn on the lower back/buttocks. FIGS. 33A and 33B further illustrate a rebound effect after compression, where, following relief of the compression, the signal overshoots the equilibrium or prior raw signal value.

In another implementation, faults may be detected by identifying a signal shape with a known signal shape that pertains to a fault. In particular, when a signal under evaluation consists of one or more predictable shapes, it is beneficial to establish an expectation of normal or abnormal signal characteristics, in order to detect artifacts and aberrations. Such an expectation, or a "template", can be compared to every newly arriving signal to assess its correlation to or deviation from the template. This comparison can be made to detect failure modes with characteristic impacts on the sensor signals, e.g., shapes, or damped or unstable responses, in order to discriminate between known fault modes, as well as to assess their severity.

In such systems, one way to achieve accurate blood glucose readings is to identify blood draws with pressure and glucose sensor signals that are consistent with patient blood access and typical enzyme sensor responses. A goal in the process is to discriminate between faulty conditions that the monitoring algorithm can reliably mitigate and faulty conditions that produce glucose measurements that do not meet required accuracy. When the algorithm cannot display accurate results, the decision logic may classify failure modes with known mechanisms and characteristics into actionable alerts. These alerts may identify faults that require user action to resolve, or faults indicating complete sensor failures.

Figures 34A, 34B:
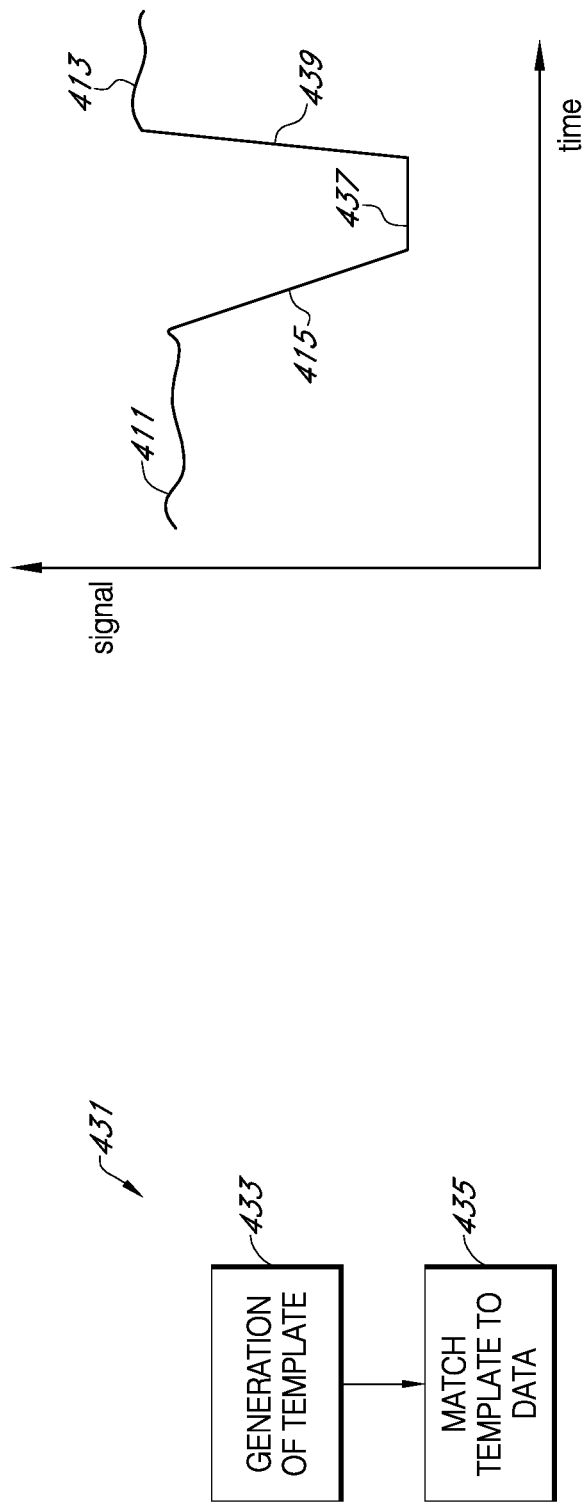
FIGS. 34A-34C illustrate a flowchart and signals for use in fault discrimination by way of template generation and matching.

Referring to the flowchart 431 of FIG. 34A, two steps may be seen in the process. A first step is the generation of templates for signals in the measurement cycle (step 433). A second step is the matching of the templates to the received data (step 435). The steps are now described in greater detail.

In the generation of templates, one approach uses singular value decomposition or a related factor analysis method to determine the sources of variation in a training set. To do this, a training set is compiled using a representative data set for reliable operation that meets the accuracy requirement or that targets a known failure mode. Such a set is arranged in an m×n matrix M, of sensor signals versus time, where m is the number of samples, stored as row vectors, and n is the number of time points in each sample. The signals can be from an electrochemical sensor, e.g., transient signal analysis from a steady state or transient measurement system, which may gain particular benefit from fast sampling of the data, as described in more detail elsewhere herein.

A singular value decomposition is performed using an available subroutine, e.g., Matlab®'s SVD function: $M=USV^t$. V is an n×n matrix that contains the singular vectors in order of decreasing contribution to the overall signal. In other words, the first column of V will include the feature that is most prominent in the training set, the second column will include the next most prominent feature, and so on. In one approach, the most prominent feature, i.e., the first singular vector, is converted into a signal template. In another approach, a signal template is a linear combination of singular vectors. Other approaches will also be understood.

Yet another approach uses a physical or mathematical model of the system to generate templates for the sensor response. An example would be a mathematical model for sensor response based on compression artifacts. Such models may be employed to generate the dynamic response seen in typical compression artifacts. Another example would be a mathematical model for sensor response based on diffusion rates. Such models may be employed to generate the dynamic response for a reliable sensor or to generate the dynamic response for a sensor that was slowed by biological fouling or encapsulation. Other mathematical models may be generated for other such signals derived from, for example, step or cyclic voltage cycles (AC or DC), intermittent exposure to a sample, or the like.

In the second step, i.e., matching template to data, the sensor signals can be the sensor response versus time or may be preprocessed to filter out electronic noise or other data collection artifacts. Each sample of incoming data is then projected onto one or more templates to determine its correlation to (or deviation from) the template in order to detect particular features and failure modes. The result of the projection gives a contribution of that particular template shape to the overall shape of the sensor signal.

In another implementation of the second step of matching template to data, the expected sensor response may be shifted in time to compensate for acceptable manufacturing, operational, and physiological variations that change fluid volumes. For example, time shifts may result from changes in catheter volume or sensor position that affect dead volume. The shifted sensor response can then be matched against templates.

Yet another approach allows for the sensor response to be stretched or compressed in time to again compensate for acceptable manufacturing, operational, and physiological variations that may arise. For example, such signal variations may result from changes in peristaltic pump efficiency or sensor response changes with temperature. An example of the method of FIG. 35A is described below.

Referring to FIG. 34B, a signal schematically illustrating a compression artifact is shown. Typical aspects include a pre-compression "regular" signal portion 411, a post-compression "regular" signal portion 413, a steep downward slope 415, a steep upward slope 439, and a flat section between the slopes 437. The downward slope generally indicates the occurrence of the compression, and the upward slope indicates relief of the compression. The time between the two may vary, but is generally a few minutes to a few tens of minutes.

Figure 34C:
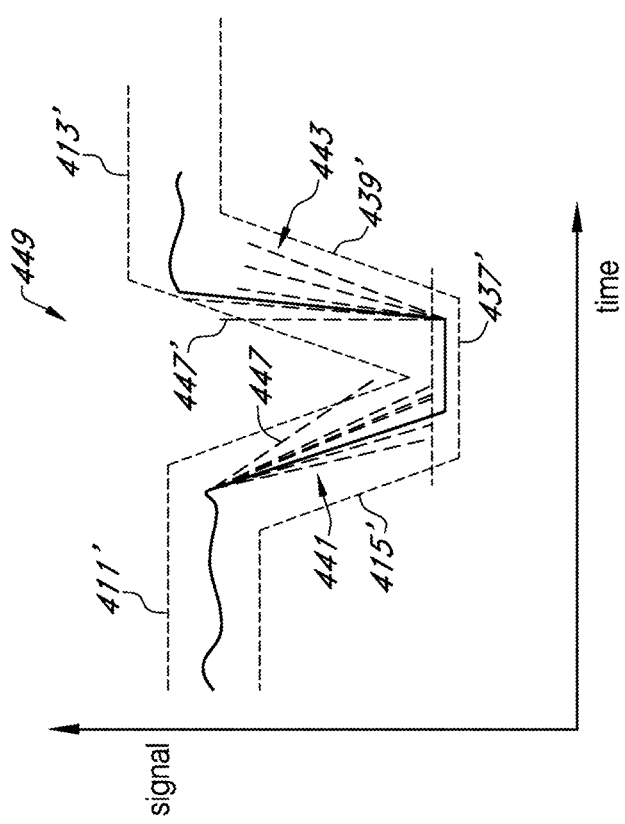

Compression artifacts generally have a shape such as illustrated, and thus a template may accordingly be generated and the same used as criteria against which incoming signals are evaluated. For example, and referring to FIG. 34C, an exemplary signal template 449 is illustrated having horizontal bands 411' and 413', a downward slope band 415', and an upward slope band 439'. A flat portion band 437' is also illustrated, and it will be understood that the length of this band (in time) may vary depending on how long the compression occurs. So long as the incoming signal is within the bands, i.e., so long as the data fits the clinical context criteria, a compression fault, i.e., clinical context information, may be determined. For example, a number of slopes for downward and upward signal waveforms 441 and 443 respectively are illustrated, and such are still within the clinical context criteria as set by the bands. On the other hand, a signal slope 447 is illustrated on the downward side, and a signal slope 447' is illustrated on the upward side, that do not fit within the bands and would thus not meet the clinical context criteria for a compression fault.

It will be understood that numerous variations may occur. For example, the position of the bands 411' and 413' within the template 449 may vary significantly in their vertical (signal value) position. The width of the bands 411' and 413' may be larger than the width of the band 437', or may be the same. Other variations will also be understood, as well as ways of providing templates without using such bands, for example, other mathematical models such as correlation analysis to a curve (template), or the like.

To determine the template, the SVD routine may be run over a large training set of individual compression artifacts collected from a wide variety of different sensor hosts whom experienced the compression artifact. The known compression artifact signature provides a tool against which each possible compression artifact may be evaluated. Multiple such templates may be created, and each time a compression artifact is detected, the measured signal may be projected onto each of the templates to obtain their contributions to the overall shape. While compression artifacts are exemplified herein, the same principles of creating and using templates for comparison against any known signature (e.g., EOL, dip and recover, transient signals obtained during a self-diagnostics cycle, or any other waveform that is produced by the sensor by any known methodology) may be applied, as is appreciated by one skilled in the art.

Figure 35B:
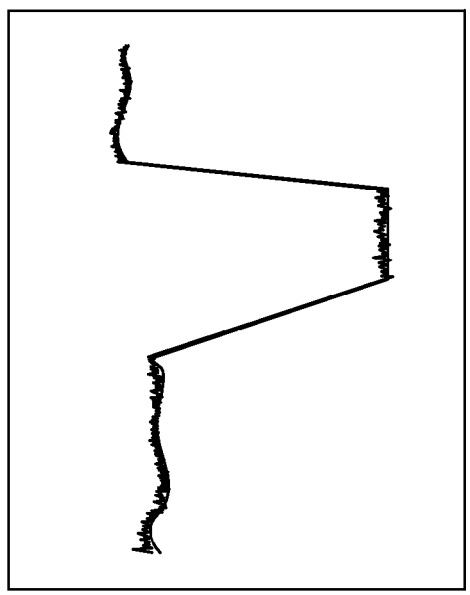
FIGS. 35A-35C illustrate a number of examples of evaluations of signals vis-à-vis templates.
Figure 35A:
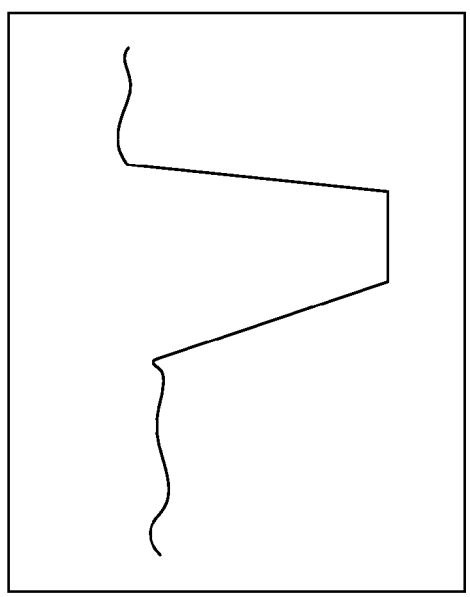
Figure 35C:
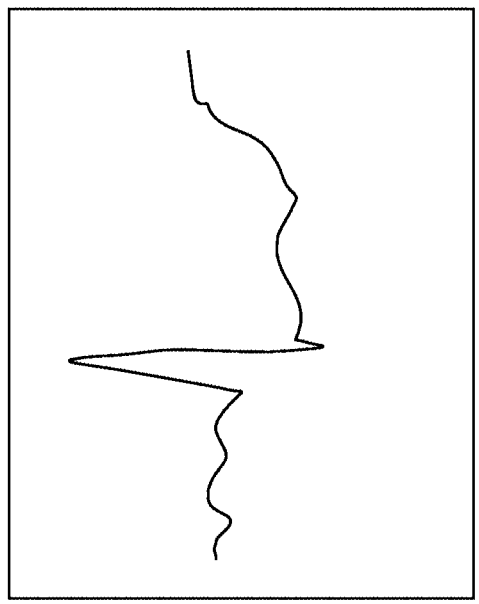

FIGS. 35A-35C illustrate a number of examples of signals which may be compared against templates. FIG. 35A illustrates an exemplary compression artifact. FIG. 35B illustrates an artifact that may be compared to the template. In this plot, the overall shape is somewhat consistent with a compression artifact, but with additional noise, but the same can still be quantified as yes/no and/or determined in terms of a confidence factor. FIG. 35C illustrates some other type of signal artifact, other than compression. The signal is not well explained by either the typical compression waveform or the normal glucose behavior, although the signal correlates more closely with the normal glucose behavior. Accordingly, while the compression artifact may not be discriminated in the particular scenario of FIG. 35C, a prompt could be sent to the user to provide additional information and/or other processing applied.

Thus, using the templates generated from a training set allows the algorithm to detect a particular failure mode that manifests itself as a particular waveform. Given a sufficiently large training data set, more templates can be easily generated for other failure modes that require discrimination. The results from template matching can be combined with clinical context information to discriminate failure modes and thus discriminate faults.

Generally the templates are created over large data sets from different patients in an empirical sense, although in certain implementations other ways of establishing templates may also be employed, including using templates established from a single patient.

What has been disclosed are systems and methods for dynamically and iteratively providing fault discrimination and responsive processing. A variety of methods have been disclosed for performing fault discrimination, as well as for processing subsequent to fault discrimination, including remedial measures.

Variations will be understood to one of ordinary skill in the art given this teaching. For example, while certain clinical context have been described above, where clinical context data is compared against clinical context criteria to develop clinical context information, it will be understood that the above-noted clinical contexts are exemplary and do not constitute an exhaustive list. For example, sensor insertion site may also serve as a clinical context. Certain sensor insertion sites may lead to a greater occurrence of fault such as dip and recover, water ingress, compression, or the like, and thus by consideration of such contexts, the discrimination or determination of a fault can be made with greater accuracy. In another variation, while in vivo sensors and measurements are generally described above, in some implementations ex vivo sensors and measurements may also be employed. In yet another variation, while continuous measurements are generally described above, certain implementations may take advantage of periodic or intermittent measurements. Other variations and types of clinical contexts will also be understood.

As yet another example of variations, techniques have been described for discriminating and responding to compression faults. Compression faults may cause CGM devices to become inaccurate when the tissue surrounding the sensor is compressed. It is believed that the compression of the tissue causes the reduced perfusion of glucose to and/or oxygen around the sensor (and resulting compressed signal). The effect typically occurs for short periods of time, such as 5 or 20 minutes to 60 minutes up to several hours. The accuracy returns when the patient adjusts positions and no longer compresses the sensor. In addition to (or alternative to) the other methods for detecting compression artifacts, a compression sensor can be placed in the transmitter or disposable sensor. The compression sensor can indicate directly if the tissue is being compressed in the region. If activated, several actions can be taken, e.g., an alarm can sound, data can be blanked by the receiver, or the patient may be alerted via a small shock, vibration, or the like. If the system is hooked up to a pump, a specific action or inaction can be taken, such as suspending insulin. In addition, the sensor can be designed so as to give the patient discomfort if the patient is compressing the sensor, discouraging lying on the sensor.

Figure 36:
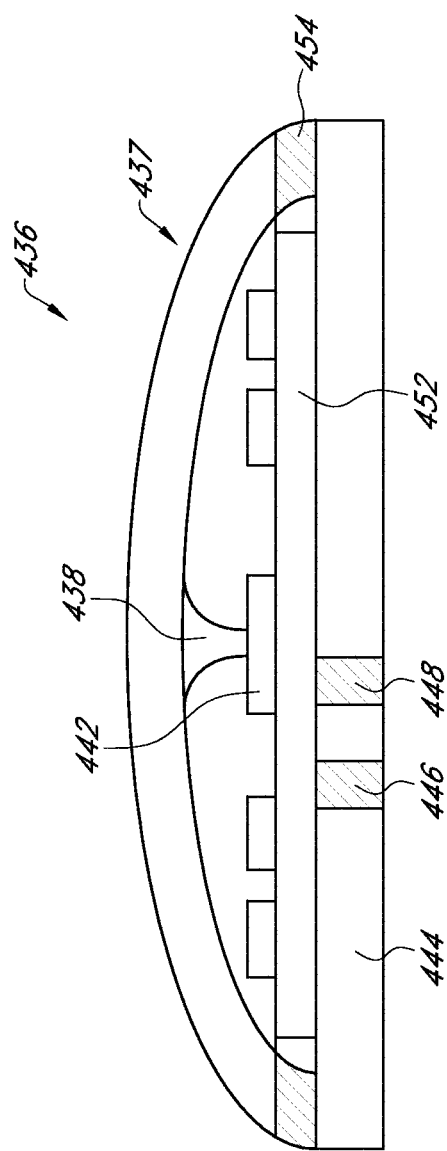
FIG. 36 illustrates a transmitter with an integrated force sensor.

For example, referring to FIG. 36, a transmitter with integrated force sensor 436 is illustrated. In this implementation, a miniature pressure transducer is disposed immediately under the sensor transmitter. In particular, a transmitter 436 formed by combining two parts, a rigid base 444 carrying the printed circuit board and a rigid cover 437. A compressible gasket 454 is provided allowing the cover to move to and from the base depending on externally applied forces. On the printed circuit board, a pressure sensing element 442 is provided which is coupled to the cover 437 by, e.g., a contacting pin 438. If force is applied to the transmitter, the cover is pushed downwards and a pressure can be sensed using the pressure sensor. In an alternative embodiment, the compressible gasket is omitted, and the cover may be provided in this case with a thin flexible section which deflects upon the application of force.

The pressure transducer measurements may be used to assist identification of spurious hypoglycemic values associated with compression applied directly to the sensor and transmitter pad. Exemplary pressure transducers include those using miniature piezoelectric pressure transducers, strain gauges, springs, capacitance measurements, and the like. Spuriously low glycemic measurements associated with compression would not as a consequence result in alarms or in other uncalled-for therapeutic action. A special algorithm could combine the pressure transducer data with the previous 60 to 90 minutes glucose trend data to further assist in differentiating actual hypoglycemic events from spurious readings induced by compression at the site of the transmitter and sensor. In this way, the phenomenon of "alarm fatigue" is minimized, increasing the likelihood that a user will respond to other alerts.

In addition, CGM systems may be employed as part of an automated insulin infusion system or artificial pancreas system. Such systems would generally include automatic suspension of insulin infusion in response to detected actual or impending hypoglycemia. As above, if the detection of hypoglycemia is correct, such an insulin pump suspension is warranted. However, if the hypoglycemia detected by the sensors is erroneous, there is the risk that an automatic pump suspension could lead to severe hyperglycemia, possibly culminating in diabetic ketoacidosis. Using the system of FIG. 36, an independent method may be employed of determining whether sensor readings are anomalous by using data from a real-time pressure transducer, significantly improving accuracy of readings and thus treatment to a patient.

In another variation, while various types of sophisticated responsive processing techniques have been disclosed, another way to handle faults or failures is to notify the patient of the problem, and to configure the system to enter a failsafe mode or to shut the sensor off.

In yet another variation, in implementations above in which a predicted or forecasted value is suggested, any method of forecasting or prediction using historic and current data values may be applied, including methods relating to pattern analysis, use of clinical context, and the like. However, a simple linear regression may also be applied. In this instance, a certain amount of data is used in a linear regression, and the same used to calculate a latest value using the regression-determined line. For example, data may be taken every 30 seconds over a five-minute period, and the same may be used in the regression analysis. This technique may also serve to smooth the data and to remove the time lag. Residuals around the line may be used as an estimate of noise level. In enhanced techniques, limits may be placed on the slope of the line computed, so as to reflect proper physiological limits. Limits may also be placed on how much the slope of the line can change between each five-minute interval. In a particular implementation, a linear regression is taken over 10 samples, and a predicted value is computed for the endpoint of the line, reducing the amount of noise and filter time delay significantly.

Figure 37:
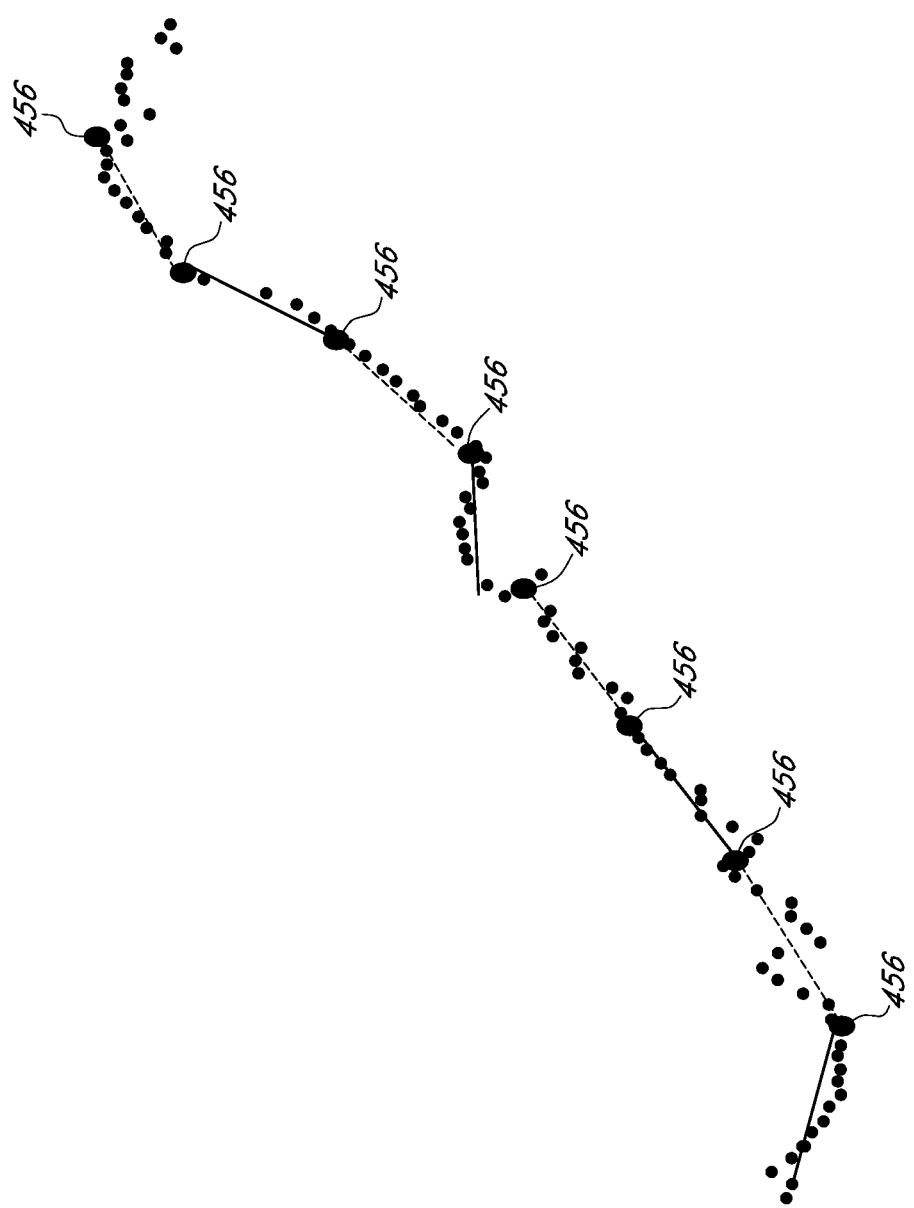
FIG. 37 illustrates the use of linear regression in prediction or forecasting.

This idea is illustrated in FIG. 37, in which points 456 delineate beginnings and endings of different 5 minutes sampling periods. 10 samples are taken in each five-minute period, corresponding to 30 second intervals. Using linear regression, the estimated glucose value for the endpoint of the line is calculated in a particularly rapid fashion. This provides a more rapid or adaptive method for performing responsive processing.

The connections between the elements shown in the figures illustrate exemplary communication paths. Additional communication paths, either direct or via an intermediary, may be included to further facilitate the exchange of information between the elements. The communication paths may be bi-directional communication paths allowing the elements to exchange information.

The various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure (such as the blocks of FIGS. 2 and 4) may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise various types of RAM, ROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. Thus, in some aspects a computer readable medium may comprise non-transitory computer readable medium (e.g., tangible media). In addition, in some aspects a computer readable medium may comprise transitory computer readable medium (e.g., a signal). Combinations of the above should also be included within the scope of computer-readable media.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

Certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for performing responsive processing in response to a fault in a continuous in vivo analyte monitoring system, comprising:
   receiving a signal from an analyte monitor;
   receiving clinical context data;

evaluating the received clinical context data against clinical context criteria to determine clinical context information; and
performing responsive processing based on at least the received signal and the determined clinical context information, wherein the responsive processing includes controlling a medicament delivery device, the controlling including adjusting a basal value or, where medicament is being delivered, suspending medicament delivery.

2. The method of claim 1 wherein the performing responsive processing includes categorizing the fault based on the received signal, the clinical context information, or both.

3. The method of claim 2, wherein the categorizing the fault includes categorizing the fault as a sensor environment fault or as a system error/artifact fault.

4. The method of claim 3, wherein the performing responsive processing includes categorizing the fault as a sensor environment fault, and further comprising subcategorizing the fault as a compression fault or an early wound response fault.

5. The method of claim 1, wherein the performing responsive processing includes slow versus fast sampling.

6. The method of claim 1, wherein the received clinical context data is selected from the group consisting of age, anthropometric data, drugs currently operating on the patient, temperature as compared to a criteria, a fault history of the patient, activity level of the patient, exercise level of the patient, a patient level of interaction with a glucose monitor, patterns of glucose signal values, clinical glucose value and its derivatives, a range of patient glucose levels over a time period, a duration over which patient glucose levels are maintained in a range, a patient glucose state, a glycemic urgency index, time of day, and pressure.

7. The method of claim 1, further comprising receiving an additional signal.

8. The method of claim 1, further comprising receiving an additional signal, wherein the additional signal is a sensor temperature signal, an impedance signal, an oxygen signal, a pressure signal, or a background signal.

9. The method of claim 1, wherein the clinical context information corresponds to data about the patient excluding a signal value measured at a sensor associated with the analyte monitor.

10. The method of claim 1, wherein the clinical context criteria includes predefined values or ranges of parameters selected from the group consisting of drugs currently operating on the patient, temperature, a fault history of the patient, activity level of the patient, exercise level of the patient, a patient level of interaction with a glucose monitor, patterns of glucose signal values, clinical glucose value and its derivatives, a range of patient glucose levels over a time period, a duration over which patient glucose levels are maintained in a range, a patient glucose state, a glycemic urgency index, time of day, and pressure.

11. The method of claim 1, wherein the clinical context data includes temperature, the clinical context criteria includes a pattern of temperatures, the evaluating determines the clinical context information to be that the user is in contact with water at the sensor site, and the performing responsive processing includes discriminating a fault type as water ingress.

12. The method of claim 1, wherein the clinical context data includes patient activity level or time of day, the clinical context criteria includes a pattern of patient activity levels, the evaluating determines the clinical context information to be that the user is compressing the sensor site, and the performing responsive processing includes discriminating a fault type as compression.

13. The method of claim 1, wherein the clinical context data includes time since implant, the clinical context criteria includes a range of times since implant in which dip and recover faults are likely, the evaluating determines the clinical context information to be that the sensor is recently implanted, and the performing responsive processing includes discriminating a fault type as a dip and recover fault.

14. The method of claim 1, wherein the clinical context data includes a clinical glucose value and a datum selected from the group consisting of age, anthropometric data, activity, exercise, clinical use of data, and patient interaction with monitor.

15. The method of claim 1, wherein the responsive processing includes providing a display to a user, the display including a warning, an alert, an alarm, a confidence indicator, a range of values, a predicted value, or a blank screen.

16. The method of claim 1, wherein the performing responsive processing includes adjusting a level of filtering of the received signal.

17. The method of claim 1, wherein the performing responsive processing includes performing a self diagnostics routine.

18. The method of claim 1, wherein the performing responsive processing includes switching from a first therapeutic mode to a second therapeutic mode.

19. An electronic device for monitoring data associated with a physiological condition, comprising:
a continuous glucose sensor, wherein the continuous glucose sensor is configured to substantially continuously measure the concentration of glucose in the host, and to provide continuous sensor data associated with the glucose concentration in the host; and
a processor module configured to perform the method of claim 1.

20. An electronic device for delivering insulin to a host, the device comprising:
a medicament delivery device configured to deliver insulin to the host, wherein the insulin delivery device is operably connected to a continuous glucose sensor, wherein the continuous glucose sensor is configured to substantially continuously measure the concentration of glucose in the host, and to provide continuous sensor data associated with the glucose concentration in the host; and
a processor module configured to perform the method of claim 1.

* * * * *

UNITED STATES PATENT AND TRADEMARK OFFICE
CERTIFICATE OF CORRECTION

PATENT NO. : 10,231,659 B2
APPLICATION NO. : 14/717965
DATED : March 19, 2019
INVENTOR(S) : Stephen J. Vanslyke It is certified that error appears in the above-identified patent and that said Letters Patent is hereby corrected as shown below:

On the Title Page

In Column 2 (Item (56)) at Line 9, Under Other Publications, change "ration" to --ratio--.

In the Specification

In Column 5 at Line 19, Change "adipanectin," to --adiponectin,--.

In Column 7 at Line 13, Change "andrenostenedione;" to --androstenedione;--.

In Column 7 at Line 29, Change "diptheria/" to --diphtheria/--.

In Column 7 at Line 36, Change "perioxidase;" to --peroxidase;--.

In Column 7 at Line 45, Change "sissomicin;" to --sisomicin;--.

In Column 7 at Line 49, Change "duodenalisa," to --duodenalis,--.

In Column 7 at Line 57, Change "Trepenoma pallidium," to --Treponema pallidum,--.

In Column 7 at Line 58, Change "stomatis" to --stomatitis--.

In Column 8 at Line 11 (Approx.), Change "Sandrex," to --Sandtex,--.

In Column 8 at Lines 11-12 (Approx.), Change "(barbituates," to --(barbiturates,--.

In Column 37 at Line 8 (Approx.), Change "µ0.75" to --µ=0.75--.

In Column 42 at Line 51, Change "adipanectin," to --adiponectin,--.

Signed and Sealed this
Eighteenth Day of June, 2019

Andrei Iancu
*Director of the United States Patent and Trademark Office*

In Column 66 at Line 36, Change "0.5 mg/dL/min" to --0.5 mg/dL/min.--.

In the Claims

In Column 83 at Line 11, In Claim 2, change "claim 1" to --claim 1,--.